(12) United States Patent
Kido et al.

(10) Patent No.: US 8,989,474 B2
(45) Date of Patent: Mar. 24, 2015

(54) X-RAY IMAGE CAPTURING SYSTEM

(75) Inventors: Kazuhiro Kido, Hino (JP); Chiho Makifuchi, Hino (JP); Junko Kiyohara, Hino (JP)

(73) Assignee: Konica Minolta Medical & Graphic, Inc. (JP)

( * ) Notice: Subject to any disclaimer, the term of this patent is extended or adjusted under 35 U.S.C. 154(b) by 193 days.

(21) Appl. No.: 13/635,189

(22) PCT Filed: Feb. 23, 2011

(86) PCT No.: PCT/JP2011/053904
§ 371 (c)(1),
(2), (4) Date: Sep. 14, 2012

(87) PCT Pub. No.: WO2011/114845
PCT Pub. Date: Sep. 22, 2011

(65) Prior Publication Data
US 2013/0011040 A1    Jan. 10, 2013

(30) Foreign Application Priority Data

Mar. 18, 2010  (JP) .................................. 2010-061973
Mar. 18, 2010  (JP) .................................. 2010-061983
Mar. 18, 2010  (JP) .................................. 2010-061993

(51) Int. Cl.
| | | |
|---|---|---|
| *G06K 9/00* | (2006.01) | |
| *G01N 23/04* | (2006.01) | |
| *A61B 6/00* | (2006.01) | |

(52) U.S. Cl.
CPC .............. *G01N 23/04* (2013.01); *A61B 6/4291* (2013.01); *A61B 6/484* (2013.01); *A61B 6/548* (2013.01);
(Continued)

(58) Field of Classification Search
None
See application file for complete search history.

(56) References Cited

U.S. PATENT DOCUMENTS 5,812,629 A *  9/1998  Clauser ........................... 378/62
7,180,979 B2 *  2/2007  Momose ......................... 378/62
(Continued)

FOREIGN PATENT DOCUMENTS

JP     58-16216 A    1/1983
JP     7-209212 A    8/1995
(Continued)

OTHER PUBLICATIONS

Momose et al. "High-speed X-ray phase imaging and X-ray phase tomography with Talbot interferometer and white synchrotron radiation" 2009 OSA, 20 Jul. 2009 / vol. 17, No. 15 / Optics Express 12540, hereinafter Momose.*
(Continued)

*Primary Examiner* — Jon Chang
*Assistant Examiner* — Oneal R Mistry
(74) *Attorney, Agent, or Firm* — Cantor Colburn LLP

(57) ABSTRACT

Disclosed in an x-ray imaging device, which uses a Talbot-Lau interferometer, eliminates the effects on image quality of a reconstructed image that arises in such cases as when the direction of a multi-slit or each lattice slit is altered and imaging is performed, and provides reconstructed images favorable for diagnosis. When a plurality of moire images imaged with an imaging subject loaded onto a imaging subject stand (13) and a plurality of moire images imaged without the imaging subject are input, a control unit (51) of a controller (5) corrects signal value differences arising from variations in x-ray strength during imaging respectively between the plurality of moire images with the imaging subject and between the plurality of moire images without the imaging subject, and respectively creates a reconstructed image with the imaging subject and a reconstructed image without the imaging subject. Then, the control unit (51) creates a reconstructed image of the imaging subject for diagnosis by correcting, on the basis of the reconstructed image without the imaging subject, image unevenness in the reconstructed image with the imaging subject caused by heterogeneity in light distribution caused by the angle of rotation of the multi-slit.

5 Claims, 38 Drawing Sheets

(52) U.S. Cl.
CPC .......... *A61B 6/4283* (2013.01); *A61B 6/50* (2013.01); *G01N 2223/406* (2013.01); *G01N 2223/612* (2013.01); *G21K 2207/005* (2013.01); *A61B 6/4423* (2013.01)
USPC ........................................ 382/132

(56) References Cited

U.S. PATENT DOCUMENTS

| | | | |
|---|---|---|---|
| 7,532,704 B2* | 5/2009 | Hempel | 378/19 |
| 2009/0238324 A1* | 9/2009 | Oikawa | 378/7 |
| 2010/0080436 A1* | 4/2010 | Ohara | 382/132 |

FOREIGN PATENT DOCUMENTS

| | | |
|---|---|---|
| JP | 2002-139459 A | 5/2002 |
| JP | 2007-203063 A | 8/2007 |
| JP | 2007-268033 A | 10/2007 |
| JP | 2008-18060 A | 1/2008 |
| JP | 2009-150875 A | 7/2009 |
| WO | 2004/058070 A1 | 7/2004 |
| WO | 2008/102685 A1 | 8/2008 |
| WO | 2008/102898 A1 | 8/2008 |
| WO | WO 2008102685 A1 * | 8/2008 |
| WO | 2009/069040 A1 | 6/2009 |

OTHER PUBLICATIONS

Weitkamp. "X-ray wavefront analysis and optics characterization with a grating interferometer" Applied Physics Letters 86, 054101 s2005d, hereinafter Weitkamp2.*

Bech. "Soft-tissue phase-contrast tomography with an x-ray tube source" Phys. Med. Biol. 54 (2009) 2747-2753, hereinafter Bech.*

International Search Report for International Application No. PCT/JP2011/053904, date of mailed May 24, 2011, with English translation.

Yamada, Asaharu et al. "Moire fringes, interference fringes applied measurement method", Corona Publishing Co., Ltd., Dec. 10, 2006 (Japanese text only).

International Preliminary Report on Patentability for International Application No. PCT/JP2011/053904, dated Sep. 18, 2012, with English translation.

* cited by examiner

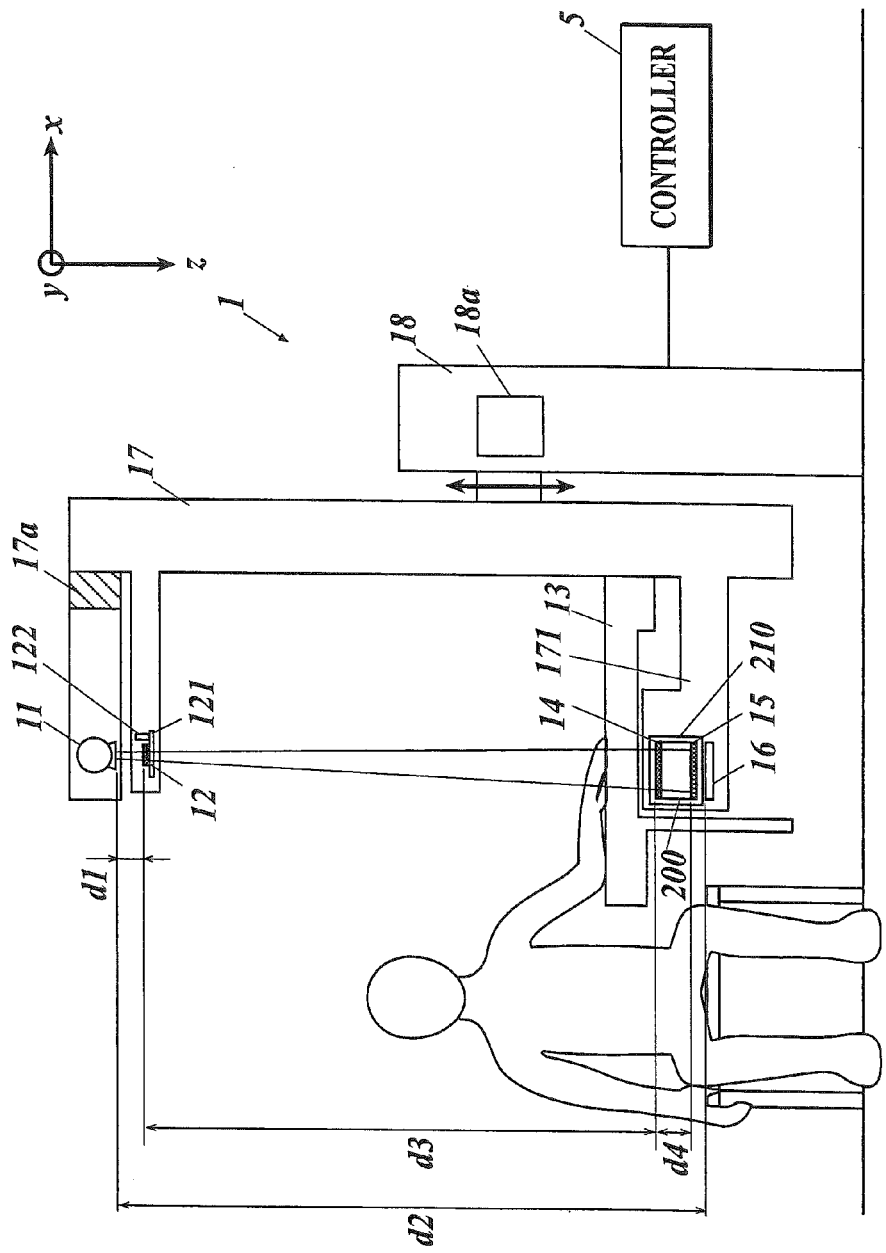

FIG.6
+0.035deg 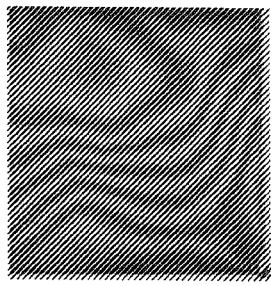
+0.03deg 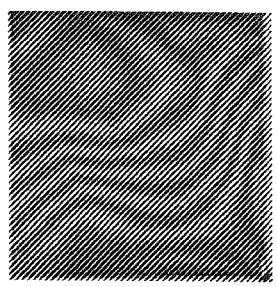
DESIGNED VALUE 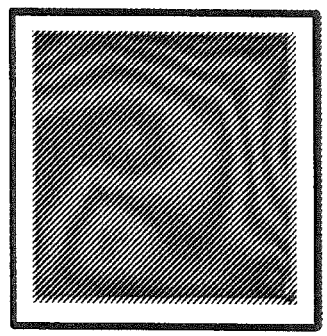
-0.015deg 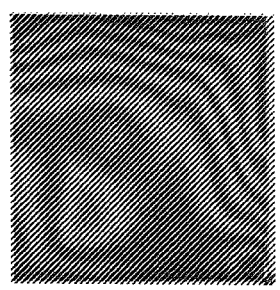
-0.025deg 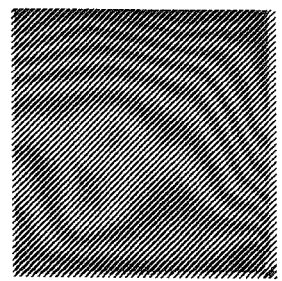

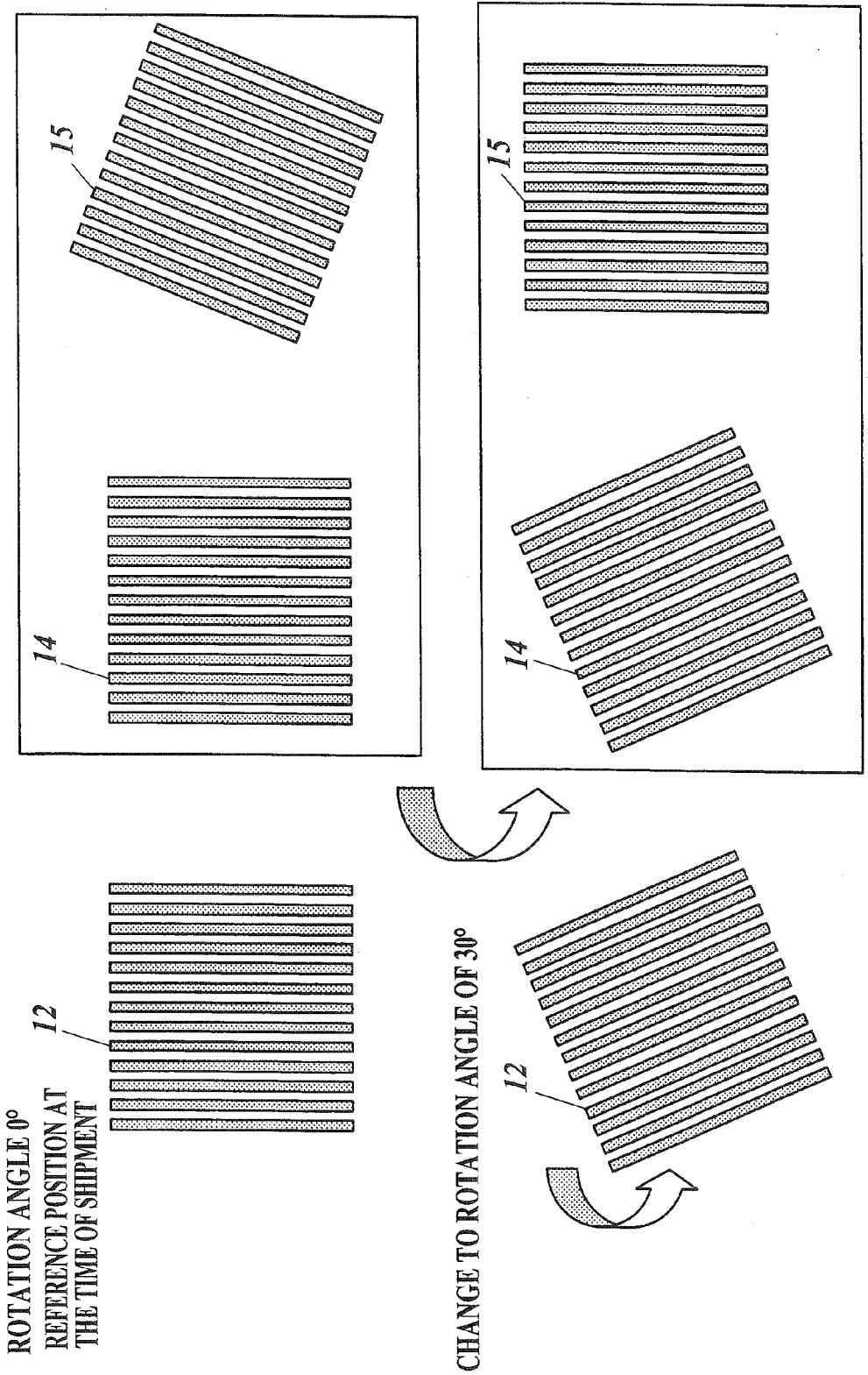

FIG.16
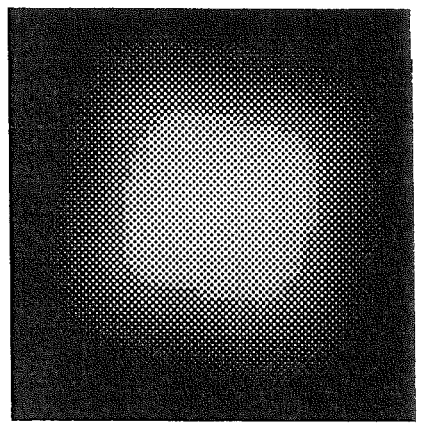
10°
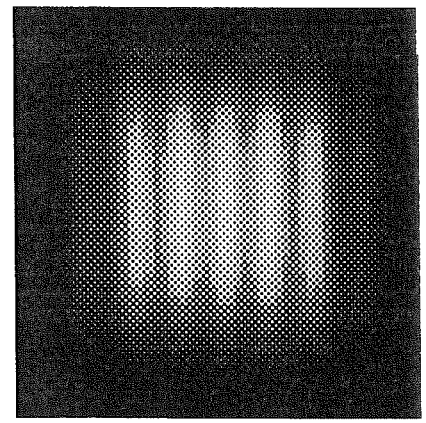
2°
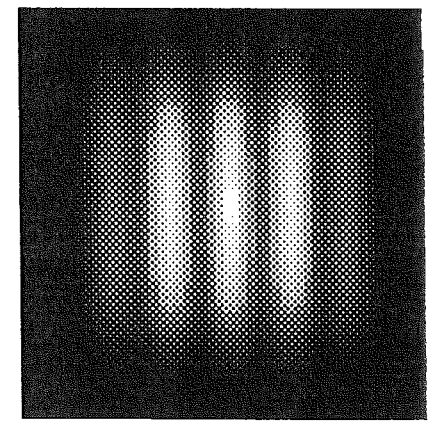
0°

X-RAY IMAGE CAPTURING SYSTEM

CROSS REFERENCE TO RELATED APPLICATIONS

This is a U.S. national stage of application No. PCT/JP2011/053904, filed on 23 Feb. 2011. Priority under 35 U.S.C. §119(a) and 35 U.S.C. §365(b) is claimed from Japanese Application Nos. 2010-061973, filed 18 Mar. 2010; 2010-061983, filed 18 Mar. 2010; and 2010-061993, filed 18 Mar. 2010, the disclosures of which are also incorporated herein by reference.

TECHNICAL FIELD

The present invention relates to a X-ray image capturing system using a Talbot-Lau interferometer.

BACKGROUND ART

Nearly all of medical X-ray images used for diagnosis are images obtained by absorption contrast method. In absorption contrast method, contrast is created by attenuation differences in X-ray intensity when X-rays pass through a subject. On the other hand, there is suggested phase contrast method in which contrast is created by phase differences in X-rays and not by absorption of X-rays. For example, phase contrast imaging by which highly visible X-ray image can be obtained by emphasizing edges using X-ray refractions at the time of magnification image capturing is being carried out (for example, see patent documents 1 and 2).

Absorption contrast method is effective in image capturing of subjects which exhibit great X-ray absorption, such as bones. In contrast, phase contrast method can form images of tissues such as breasts, articular cartilages and soft tissues around articulars which are difficult to be captured as images by absorption contrast method because differences in X-ray absorption is small, and is expected to be utilized in X-ray image diagnosis.

As one type of phase contrast imaging, Talbot interferometer using Talbot effect has been considered (for example, patent documents 3 to 5). Tabot effect is a phenomenon in which when coherent light passes through the first grating having slits in constant cycles, grating images are repeated at constant intervals in the traveling direction of the light. These grating images are called self images. In Talbot interferometer, the second grating is disposed at the position where a self image is formed and measures the interference fringes (moire) that occur due to slightly displacing the second grating. Because moire is disturbed when an object is placed in front of the second grating, when X-ray image capturing is to be carried out by using Talbot interferometer, reconstruction image of a subject can be obtained by placing the subject in front of the first grating and emitting coherent X-rays onto the subject, and then, by performing arithmetic calculation of the obtained moire image.

Further, there is suggested a Talbot-Lau interferometer in which a multi-slit is disposed between the X-ray source and the first grating to increase the amount of X-ray emission (for example, see patent document 6). In a conventional Talbot-Lau interferometer, a plurality of moire images are captured in constant cycles while moving the first grating or the second grating (while relatively displacing both gratings). The multi slit is provided in order to increase the amount of X-ray emission.

The inventors of the present invention found out that an image equivalent to reconstruction image obtained by the conventional method can also be obtained by moving the multi-slit with respect to the first grating and the second grating in the Talbot-Lau interferometer, and this technique has been filed as Japanese Patent Application No. 2009-214483 (PCT/JP2010/53978).

In the above Talbot apparatus and Talbot-Lau apparatus, it is known that interference fringes in each moire image used in generation of reconstruction image need to be sharp and that the number of interference fringes needs to be small in order to obtain a sharp reconstruction image (for example, see non-patent document 1 (page 15)).

PRIOR ART DOCUMENTS

Patent Documents

Patent Document 1: Japanese Unexamined Patent Application Publication No. 2007-268033
Patent Document 2: Japanese Unexamined Patent Application Publication No. 2008-18060
Patent Document 3: Japanese Unexamined Patent Application Publication No. Shou58-16216
Patent Document 4: WO2004/058070
Patent Document 5: Japanese Unexamined Patent Application Publication No. 2007-203063
Patent Document 6: WO2008/102898

Non-Patent Documents

Non-Patent Document: "Moire fringes, interference fringes applied measurement method", Asaharu YAMADA, Shunsuke YOKOZEKI, CORONA PUBLISHING CO., LTD, Dec. 10, 1996

SUMMARY OF THE INVENTION

Problem to be solved by the Invention

In Talbot interferometer and Talbot-Lau interferometer, because the first grating and the second grating intervene between a subject and the X-ray detector, the first grating and the second grating need to be arranged so that the longitudinal directions of slits (called slit direction) of the first grating and the second grating be in the optimal state with respect to the structural to be focused in the subject. Further, the slit direction of the multi-slit also needs to be adjusted along with the slit directions of the first grating and the second grating.

However, if the slit directions of the first grating and the second grating are fixed, a patient is to be required to stay in a stressful posture and this is not preferable. It is possible to change the slit directions of multi-slit, the first grating and the second grating while the subject is being fixed. However, due to the X-ray source not being an ideal positional light source, size errors caused by manufacturing variation in multi-slit and gratings and interrelating effects of the above, unevenness in X-ray distribution occurs according to the slit directions of the multi-slit and the gratings during image capturing and a high definition reconstruction image cannot be generated. This needs to be solved.

Further, differently from a simple X-ray image capturing system in which the procedure completes in a second, a patient needs to be refrained from moving his/her body while number of moire images are being captured (normally, about few minutes) causing the patient great stress. Patients who suffer from rheumatism cannot entirely fit their hands and fingers on a flat subject platform, and it is expected that re-capturing of images will be needed due to the positions of fingers and the like moving unconsciously. To deal with this, a holder or the like for controlling such moving of a patient during image capturing can be provided on the subject platform. However, in such case, the amount of X-ray that reaches the X-ray detectors will be uneven and this causes image nonuniformity (artifact) in reconstruction image for diagnosis.

Moreover, even when it is configured so that the slit directions of the first grating and the second grating are changeable, the relative positional relation of the first grating and the second grating and the slit direction of the multi-slit with respect to the first grating and the second grating need to be adjusted in order to optimize the number of interference fringes and sharpness of interference fringes in moire images. However, it is not easy to adjust both the number of interference fringes and sharpness of interference fringes in moire images and such adjustment requires a fair amount of time. Thus, such adjustment is not preferable because a patient has to be restrained for a long period of time.

Further, in a case where the relative positional relation between the multislit, the first grating and the second grating is maintained and the slit directions thereof with respect to a patient can be adjusted, the adjustment mechanism of slit directions becomes large and the apparatus configuration will be complicated. Thus, this is not preferable.

An object of the present invention is to provide a reconstruction image good for diagnosis by removing an influence on image quality of a reconstruction image caused by performing image capturing by changing slit directions of the multi-silt and the gratings in a X-ray image capturing apparatus utilizing Talbot-Lau interferometer.

Means for Solving the Problem

In order to solve the above problem, according to one aspect of the present invention a X-ray image capturing system includes a X-ray source which emits X-rays,
a multi-slit having a plurality of slits aligned in a direction orthogonal to X-ray emission axis direction,
a first grating and a second grating each having a plurality of slits aligned in the direction orthogonal to the X-ray emission axis direction,
a subject platform,
a X-ray detector in which conversion elements which generate electric signals according to the emitted X-rays are two dimensionally arranged and which reads the electric signals generated by the conversion elements as image signals and
a diagnosis image forming unit which (1) corrects signal value differences caused by X-ray intensity variations during image capturing among a plurality of moire images with subject which are captured by placing the subject on the subject platform, (2) corrects signal value differences caused by X-ray intensity variations during image capturing among a plurality of moire images without subject which are captured by not placing the subject on the subject platform in a state same as when the plurality of moire images with subject are captured and (3) forms a subject reconstruction image for diagnosis on the basis of the plurality of moire images with subject which are corrected and the plurality of moire images without subject which are corrected, and every time the multi-slit moves in a slit aligning direction at a constant cycle interval or every time the first grating and the second grating relatively move in a slit aligning direction at a constant cycle interval, the X-ray image capturing system forms a subject reconstruction image on the basis of the plurality of moire images which are obtained by performing a plurality of times of image capturing by the X-ray detector repeating read processing of the image signals in response to the X-rays emitted by the X-ray source.

Preferably, the diagnosis image forming unit includes a reconstruction image with subject forming unit which corrects the signal value differences caused by the X-ray intensity variations during image capturing among the plurality of moire images with subject which are capturing with the subject being placed on the subject platform and which forms a reconstruction image with subject on the basis of the plurality of mire images which are corrected and a reconstruction image without subject forming unit which corrects the signal value differences caused by the X-ray intensity variations during image capturing among the plurality of moire images without subject which are captured by not placing the subject on the subject platform in the state same as when the plurality of moire images with subject are captured and which forms a reconstruction image without subject on the basis of the plurality of moire images which are corrected, and the diagnosis image forming unit forms a subject reconstruction image for diagnosis on the basis of the reconstruction image with subject and the reconstruction image without subject.

Preferably, the X-ray image capturing system further includes a detection unit which detects a X-ray exposure dose during each of a plurality of times of image capturing with subject and without subject, and the reconstruction image with subject forming unit corrects the signal value differences caused by the X-ray intensity variations during image capturing among the plurality of moire images with subject on the basis of the X-ray exposure dose during image capturing with subject detected by the detection unit, and the reconstruction image without subject forming unit corrects the signal value differences caused by the X-ray intensity variations during image capturing among the plurality of moire images without subject on the basis of the X-ray exposure dose during image capturing without subject detected by the detector.

Preferably, the X-ray image capturing system further includes a grating assembly in which a relative positional relation of the first grating and the second grating is adjusted and fixed in advance, a grating assembly rotation unit which rotates the grating assembly around a X-ray emission axis to adjust a slit direction of the grating assembly with respect the subject and a multi-slit rotation unit which rotates the multi-slit around the X-ray emission axis according to rotation of the grating assembly.

Preferably, in the grating assembly, the relative positional relation of the first grating and the second grating is adjusted and fixed in advance so that either of sharpness of interference fringes and the number of interference fringes in the moire images fulfill a pre-set standard.

Preferably, the X-ray image capturing system further includes a control unit which adjusts the other of the sharpness of interference fringes and the number of interference fringes in the moire images that is not adjusted in advance in the grating assembly by rotating the multi-slit around the X-ray emission axis by the multi-slit rotation unit according to rotation of the grating assembly.

Preferably, the X-ray image capturing system further includes a refractive index adjusting unit which reduces a difference in X-ray refractive index between a subject surface in the X-ray emission direction corresponding to a region of interest in the subject and a surrounding of the subject surface so as to be smaller than a difference in X-ray refractive index between the region of interest and a surrounding of the region of interest.

Advantageous Effect of the Invention

According to the present invention, when image capturing is performed by changing slit directions of the multi-slit and the gratings in the grating assembly in the X-ray image capturing apparatus utilizing Talbot Lau interferometer, an influence on image quality that is easily caused by manufacturing variations and the like can be removed and a reconstruction image good for diagnosis can be provided regardless of manufacturing variations and the like of the slits.

BRIEF DESCRIPTION OF THE DRAWINGS

[FIG. 1] This is a diagram showing a X-ray image capturing system (including a side view of a X-ray image capturing apparatus) according to the first and the second embodiments.

[FIG. 6] This is a diagram showing changes in a moire image when relative angle of the first grating and the second grating is changed.

[FIG. 15] This is a diagram schematically showing a relation of slit directions of a multi-slit, the first grating and the second grating.

[FIG. 16] This is a diagram showing moire images which are captured by setting the relative angle of the multi-slit and the grating assembly (the first grating and the second grating) at 0 degree, 2 degrees and 10 degrees.

BEST MODE FOR CARRYING OUT THE INVENTION

Figure 2A:
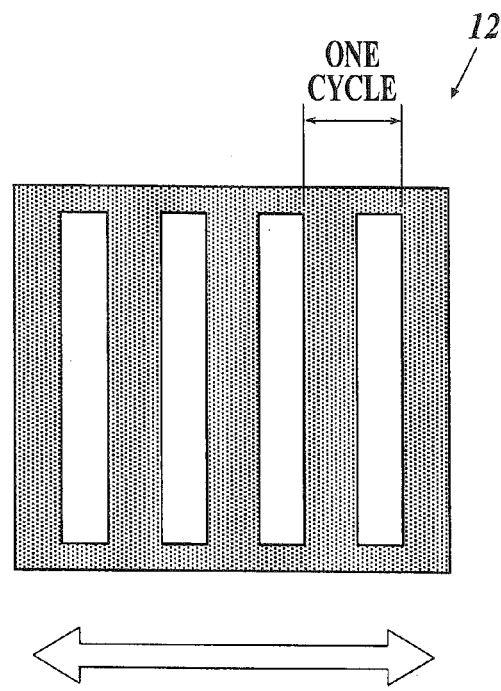
[FIG. 2A] This is a plane view of a multi-slit.

Hereinafter, embodiments of the present invention will be described with reference to the drawings.

[First Embodiment]

In FIG. 1, a X-ray image capturing system according to the embodiment is shown. The X-ray image capturing system includes a X-ray image capturing apparatus 1 and a controller 5. The X-ray image capturing apparatus 1 performs X-ray image capturing by Talbot-Lau interferometer and the controller 5 forms a reconstruction image of a subject using moire images obtained by the X-ray image capturing. In the embodiment, the X-ray image capturing apparatus 1 is described as an apparatus for performing image capturing of a hand and fingers as a subject. However, the present invention is not limited to such apparatus.

As shown in FIG. 1, the X-ray image capturing apparatus 1 includes a X-ray source 11, a multi-slit 12, a subject platform 13, the first grating 14, the second grating 15, a X-ray detector 16, a holding unit 17, a main body 18 and such like. The X-ray image capturing apparatus 1 is vertical type, and the X-ray source 11, the multi-slit 12, the subject platform 13, the first grating 14, the second grating 15 and the X-ray detector 16 are arranged along z direction which is the direction of gravity in this order. Distance between the focus point of the X-ray source 11 and the multi-slit 12 is expressed as d1 (mm), distance between the focus point of the X-ray source 11 and the X-ray detector 16 is expressed as d2 (mm), distance between the multi-slit 12 and the first grating 14 is expressed as d3 (mm) and distance between the first grating 14 and the second grating 15 is expressed as d4 (mm).

Preferably, distance d1 is 5 to 500 (mm), and more preferably, 5 to 300 (mm).

It is preferred that distance d2 is at least 3000 (mm) or shorter because the height of the imaging room of radiology department is normally about 3 (m) or less. In particular, it is preferred that distance d2 is 400 to 5000 (m), and more preferably, 500 to 2000 (mm).

Distance (d1+d3) between the focus point of X-ray source 11 and the first grating 14 is preferably 300 to 5000 (mm), and more preferably, 400 to 1800 (mm).

Distance (d1+d3+d4) between the focus point of X-ray source 11 and the second grating 15 is preferably 400 to 5000 (mm), and more preferably, 500 to 2000 (mm).

Each distance can be set by calculating the optimum distance where the grating image (self image) of the first grating 14 overlaps the second grating 15 from the wavelength of X-ray which is emitted from the X-ray source 11.

The X-ray source 11, the multi-slit 12, the subject platform 13, the first grating 14, the second grating 15 and the X-ray detector 16 are temporarily held by the same holding unit 17 and the positional relation between the above in z direction is fixed. The holding unit 17 is formed in a C-shape arm figure and is attached to the main body 18 so as to move (rise/fall) in z direction by the drive unit 18a provided in the main body 18.

The X-ray source 11 is held via a cushion member 17a. Any material can be used for the cushion member 17a as long as it is a material which can absorb shock and shaking and elastomer is suggested as such material, for example. Because the X-ray source 11 heats up by X-ray emission, it is preferable that the cushion member 17a in the X-ray source 11 side is also formed of a heat insulation member.

The X-ray source 11 includes a X-ray tube and emits X-rays in z direction (the direction of gravity) by generating X-rays by the X-ray tube. As the X-ray tube, a Coolidge X-ray tube or a rotation anode X-ray tube which are widely and generally used in medical field can be used, for example. As an anode, tungsten or molybdenum can be used.

Focus diameter of X-rays is preferably 0.03 to 3 (mm), and more preferably, 0.1 to 1 (mm).

The multi-slit 12 (grating unit) is a diffraction grating and a plurality of slits are arranged at predetermined intervals as shown in FIG. 2A. The plurality of slits are aligned in the direction (shown by white arrow in FIG. 2A) orthogonal to the X-ray emitting direction (z direction FIG. 1). The multi-slit 12 is formed with a material having a great X-ray blocking power, that is, having high X-ray absorption rate such as tungsten, lead and gold on a substrate of a material having low X-ray absorption rate such as silicon and glass. For example, by photolithography, a resist layer is masked in a slit-pattern and the slit-pattern is transferred onto the resist layer by being irradiated by UV rays. A slit structure having the same pattern is obtained by exposure and the multi-slit 12 is formed by metal being embedded between the slit structures by electroforming.

The multi-slit 12 has slit cycle of 1 to 60 (μm). One slit cycle is the distance between slits that are adjacent to each other as shown in FIG. 2A. Width of each slit (length of each slit in slit aligning direction) is 1 to 60(%) of slit cycle, and more preferably, is 10 to 40(%). Height of each slit (height in z direction) is 1 to 500 (μm), and more preferably, 1 to 150 (μm).

When the slit cycles of the multi-slit 12 is set to $w_0$ (μm) and the slit cycles of the first grating 14 is set to $x_1$ (μm), the slit cycle $x_0$ can be obtained by the following formula.

$$W_0 = w_1 \cdot (d3+d4)/d4$$

By deciding the cycle $w_0$ so as to fulfill the above formula, self images which are formed by X-rays passed through the slits of multi-slit 12 and the slits of the first grating 14 overlap on the second grating 15 to create a so-called focused state.

Figure 2B:
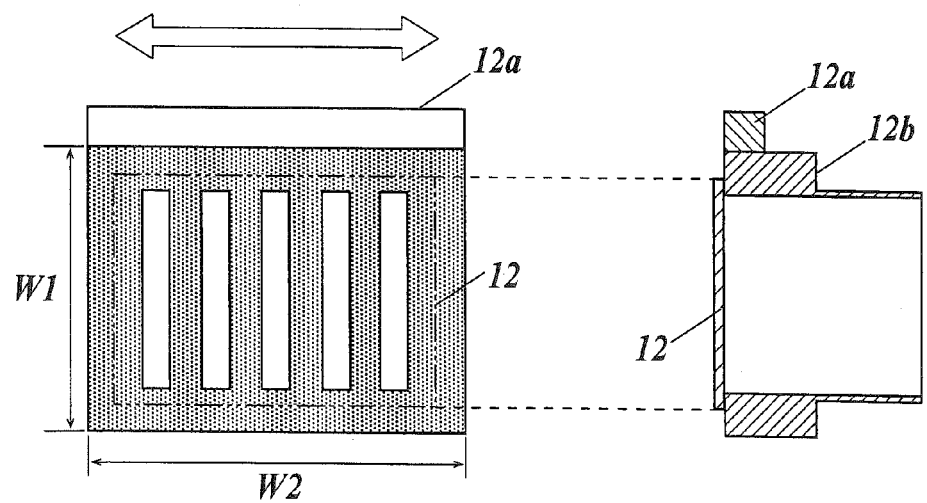
[FIG. 2B] This is a plane view and a side view when the multi-slit is held in a holder.

As shown in FIG. 2B, the multi-slit 12 is held in a holder 12b including a rack 12a. The rack 12a is provided in the slit aligning direction of the multi-slit 12. The rack 12a is engaged with a pinion 122c of the after-mentioned drive unit 122, and the rack 12a is for moving the multi-slit 12 which is held in the holder 12b in the slit aligning direction according to the rotation (phase angle) of the pinion 122c.

In the embodiment, the X-ray image capturing apparatus 1 includes the multi-slit rotation unit 121 and the drive unit 122. The multi-slit rotation unit 121 is a mechanism for rotating the multi-slit 12 which is held in the holder 12b around the X-ray emission axis according to the rotation (phase angle) of the first grating 14 and the second grating 15 around the X-ray emission axis. The drive unit 122 is a mechanism for moving the multi-slit 12 in the slit aligning direction to capture a plurality of moire images.

Figure 3:
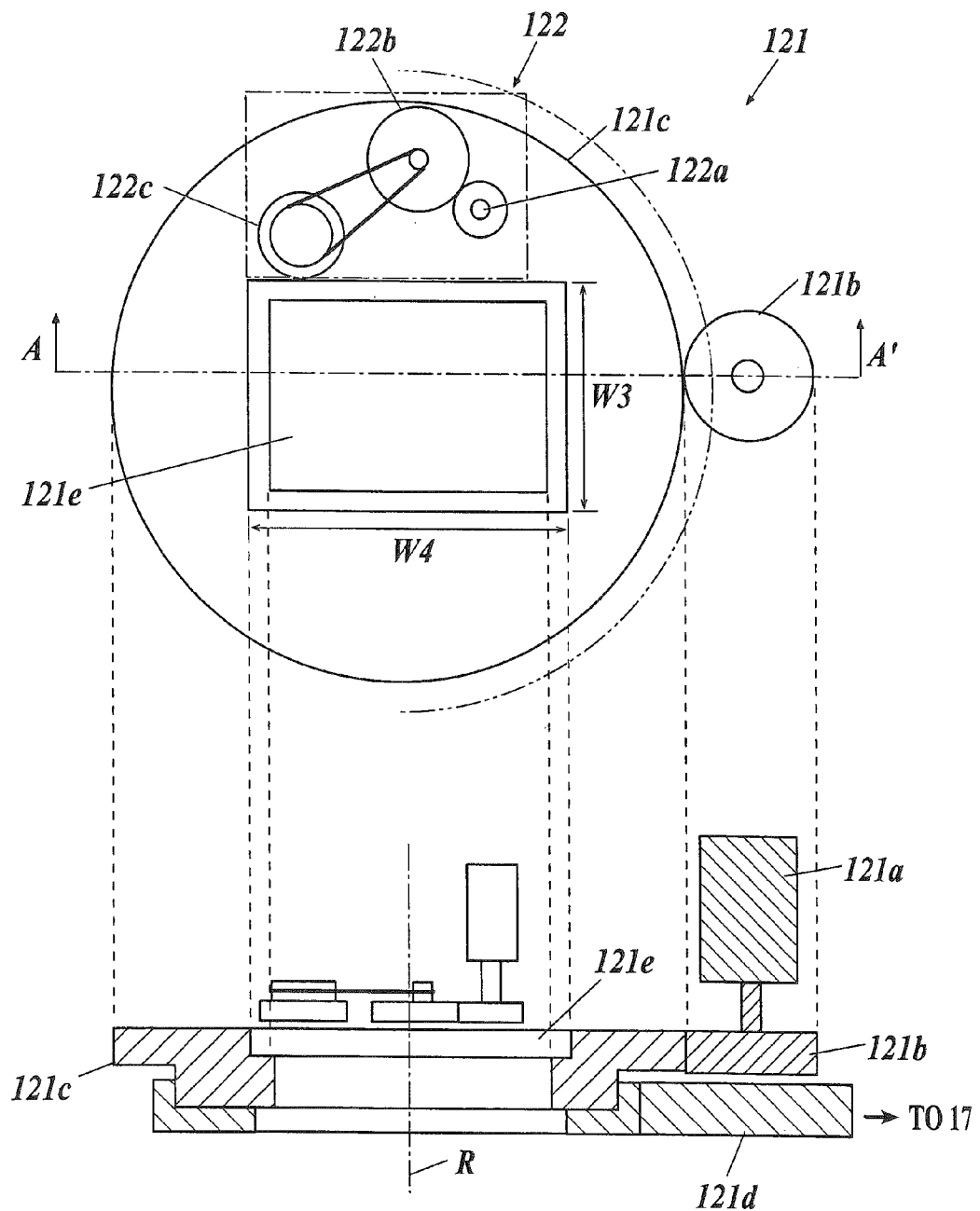
[FIG. 3] This is a plane view and a side view of a multi-slit rotation unit.

FIG. 3 shows a plane view of the multi-slit rotation unit 121 and the drive unit 122 and a sectional view cut along the line A-A'. As shown in FIG. 3, the multi-slit rotation unit 121 includes a motor unit 121a, a gear unit 121b, a gear unit 121c, a support unit 121d and such like. The motor unit 121a, the gear unit 121b and the gear unit 121c are held by the holding unit 17 via the support unit 121d.

Figure 11:
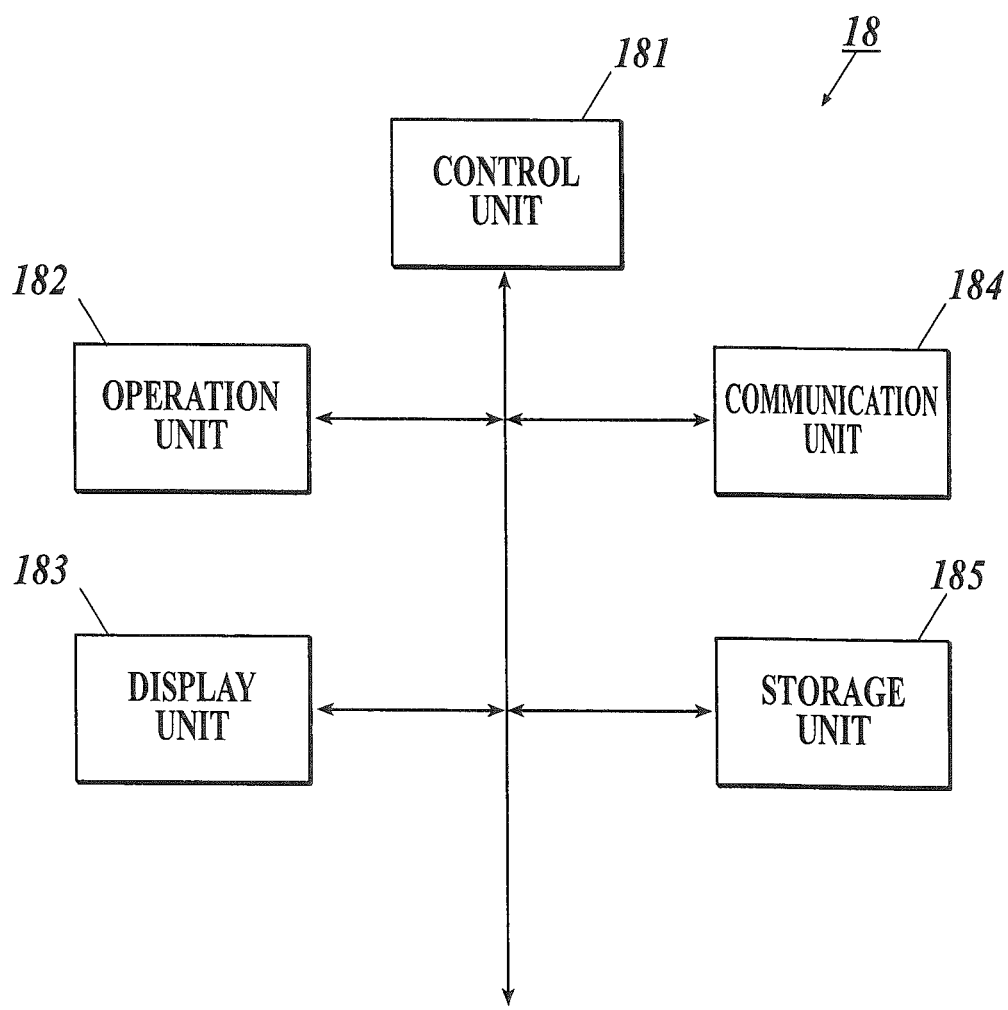
[FIG. 11] This is a block diagram showing a functional structure of a main body.

The motor unit 121a is a pulse motor that can be switched to a micro step drive, and the motor unit 121a is driven according to the control of the control unit 181 (see FIG. 11)

to rotate the gear unit 121c in the X-ray emission axis (shown by dashed line R in FIG. 3) via the gear unit 121b. The gear unit 121c includes an opening 121e for installing the multi-slit 12 which is held in the holder 12b. By rotating the gear unit 121c, the multi-slit 12 which is installed in the opening 121e rotates around the X-ray emission axis and the slit aligning direction of the multi-slit 12 can be changed. Here, it is sufficient that the multi-slit 12 can rotate for about 0° to 90° during image capturing, and therefore, the gear unit 121c does not need to be provided around the entire circumference and it is sufficient that the multi-slit 12 can rotate within the range (90° each in forward rotation direction and reverse rotation direction) shown by the two-dot chain line in FIG. 3.

The opening 121e is formed in a shape and size so that the multi-slit 12 which is held in the holder 12b can be fitted from the above. Here, size W4 in the opening 121e in the slit aligning direction is slightly larger than size W2 of the holder 12b in the slit aligning direction, and the multi-slit 12 can slide in the slit aligning direction. Size W3 in the opening 121e which is in the direction orthogonal to the slit aligning direction is in a size which allows close fitting with size W1 of the holder 12b in the direction orthogonal to the slit aligning direction. When the holder 12b is installed in the opening 121e, the rack 12a provided at the holder 12b is to be disposed outside of the opening 121e so as to engage with the after-mentioned pinion 122c.

The drive unit 122 is configured by including an precise decelerator or the like for moving the multi-slit 12 in the slit aligning direction in units of a few µm. For example, as shown in FIG. 3, the drive unit 122 includes the motor unit 122a, the gear unit 122b, the pinion 122c and the like, and the drive unit 122 is fixed on the gear 121c of the multi-slit rotation unit 121 by a L-shape metal plate or the like which is omitted in the drawing. In such way, the multi-slit 12 and the drive unit 122 are to rotate integrally.

The motor unit 122a is, for example, driven according to the control of the control unit 181 to rotate the pinion 122c via the gear unit 122b. By the pinion 122c engaging with the rack 12a of the multi-slit 12 and rotating, the multi-slit 12 moves in the slit aligning direction.

Going back to FIG. 1, the subject platform 13 is a platform for placing a hand and fingers which are subject. It is preferable that the subject platform 13 is provided to have a height so that a patient can put his/her elbow thereon. In such way, by configuring so that all the way to the elbow of a patient can be placed thereon, the patient can be in a comfortable posture and moving of image capturing parts in finger tips can be reduced during a relatively long image capturing time.

Figure 4A:
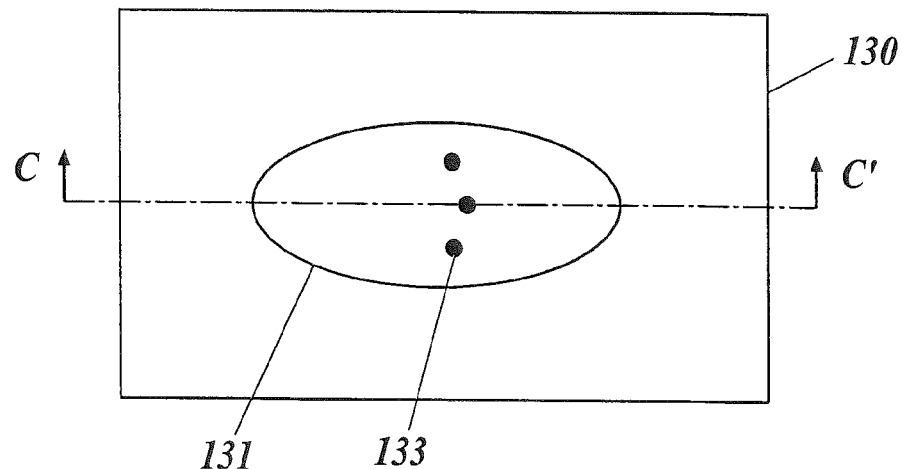
[FIG. 4A] This is a plane view of a subject holder.
Figure 4B:
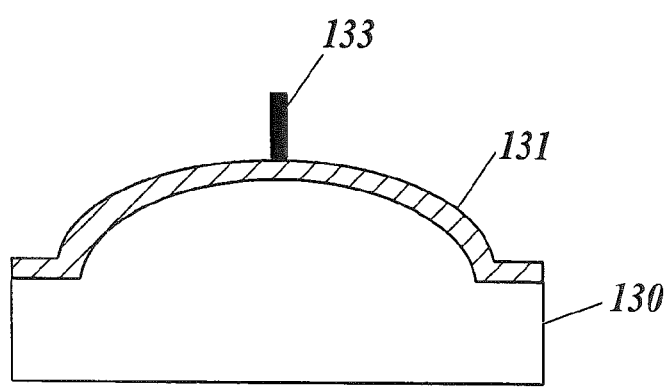
[FIG. 4B] This is a side view of the subject holder.

Further, the subject platform 13 is provided with the subject holder 130 for fixating the subject. As shown in FIG. 4A, the subject holder 130 is a plate-like member with an oval shape 131 like a mouse which is easy to hold with a palm of a hand. When the section (C-C') of the oval shape 131 is observed from a side, as shown in FIG. 4B, the oval shape 131 has a smooth convex curved surface in a size of palm of a hand, and by a patient holding the oval shape 131 with his/her hand, moving of a subject in downward direction can be restricted in a condition where the subject will not be tired easily.

When the subject holder 130 has a shape or thickness that causes X-ray transmission be uneven from place to place, the amount of X-ray that reaches the X-ray detector 16 is non-uniform because X-ray transmissivity of the subject holder 130 is uneven.

It is preferred that finger spacers 133 are provided on the subject holder 130 to further stabilize the subject posture. Further, because size of a hand and spaces between fingers are different for each subject, it is preferred that a subject holder 130 is formed according to hand palm shape of each patient and the subject holder 130 for each patient is to be attached on the subject platform 13 by a magnet or the like during image capturing. Weight from an arm to a wrist is to be supported by the subject platform 13, therefore, the subject holder 130 can be made of resin (plastic) which is cheap and which allows mass-production as long as it can endure weight of finger tip portions and force by a patient that holds down the holder.

Going back to FIG. 1, the first grating 14 is a diffraction grating in which a plurality of slits are provided so as to be aligned in the direction orthogonal to z direction which is the X-ray emission axis similarly to the multi-slit 12. The first grating 14 can be formed by photolithography using UV rays similarly to the multi-slit 12 or the grating configuration can be formed only with silicon by performing deep drill processing in fine lines on a silicon substrate by a so-called ICP method. Slit cycle of the first grating 14 is 1 to 20 (µm). Width of each slit is 20 to 70(%) of the slit cycle, and more preferably, 35 to 60(%). Height of each slit is 1 to 100 (µm).

When a phase type is to be used as the first grating 14, height of each slit (height in z direction) is set to a height that makes the phase difference in two types of materials that form the slit cycle, that is, the phase difference in materials of X-ray transmission unit and X-ray blocking unit be $\pi/8$ to $15\times\pi/8$. More preferably, $\pi/4$ to $3\times\pi/4$. When an absorption type is to be used as the first grating 14, height of each slit is set to a height that X-ray can be sufficiently absorbed by the X-ray blocking unit.

When the first grating is a phase type, distance d4 between the first grating 14 and the second grating 15 needs to nearly fulfill the following condition.

$$d4=(m+\tfrac{1}{2})\cdot w_1^2/\lambda$$

Here, m is an integer and $\lambda$ is a wavelength of X-ray.

Similarly to the multi-slit 12, the second grating 15 is a diffraction grating in which a plurality of slits are aligned in the direction orthogonal to z direction which is the X-ray emission axis. The second grating 15 can also be formed by photolithography. Slit cycle of the second grating 15 is 1 to 20 (µm). Width of each slit is 30 to 70(%) of the slit cycle, and more preferably, 35 to 60(%). Height of each slit is 1 to 100 (µm).

In the embodiment, the grating surfaces of the first grating 14 and the second grating 15 are vertical (parallel in x-y plane) with respect to z direction and although, the slit aligning direction in the first grating 14 and the slit aligning direction in the second grating 15 can be parallel in x-y plane or can be tilted by a predetermined angle within the range between 0° to 5° for the purpose of obtaining reconstruction images for diagnosis, the slit aligning direction in the first grating 14 and the slit aligning direction in the second grating 15 are tilted by a predetermined angle (0.3° to 0.5°) in x-y plane in the embodiment so that adjustment can be carried out easily.

The above described multi-slit 12, the first grating 14 and the second grating 15 can be configured as described bellow, for example.

Focus diameter of X-ray tube of the X-ray source 11; 300 (µm), tube voltage: 40 (kVp), added filter: aluminum 1.6 (mm)

Distance d1 from the focus point of the X-ray source 11 to the multi-slit 12: 240 (mm)

Distance d3 from the multi-slit 12 to the first grating 14: 1110 (mm)

Distance d3+d4 from the multi-slit 12 to the second grating 15: 1370 (mm)

Size of the multi-slit 12: 10 (square mm), slit cycle: 22.8 (μm)

Size of the first grating 14: 50 (square mm), slit cycle: 4.3 (μm)

Size of the second grating 15: 50 (square mm), slit cycle: 5.3 (μm)

Figure 5:
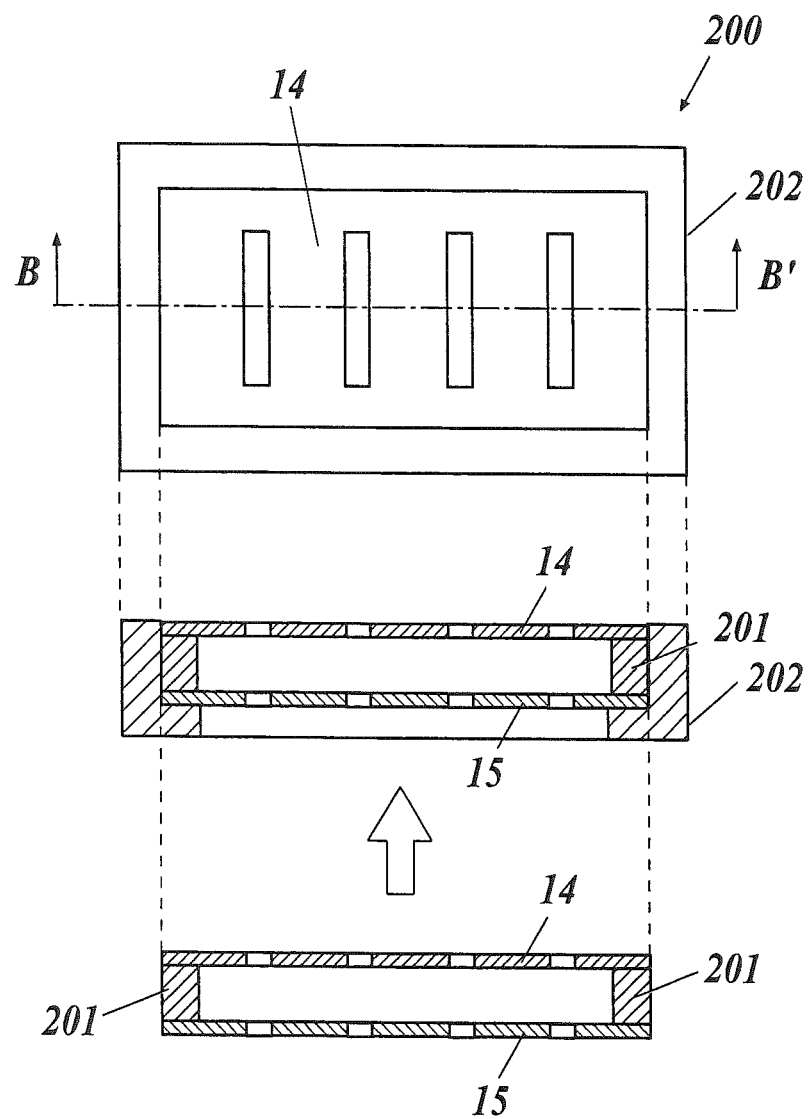
[FIG. 5] This is a diagram schematically showing a configuration of a grating assembly.

In the embodiment, the first grating 14 and the second grating 15 constitute the grating assembly 200 in which relative positional relation of the first grating 14 and the second grating 15 is prefixed by a spacer (fixed member) 201 and the holder 202 as shown in FIG. 5. FIG. 5 shows a plane view of the grating assembly 200 and a sectional view of the grating assembly 200 cut along the line B-B'.

As described above, in Talbot-Lau interferometer, it is known that lesser the number of interference fringes in moire images, sharper the reconstruction image to be formed on the basis of the moire images (see non-patent document 1).

In view of the above, in the grating assembly 200 of the embodiment, the first grating and the second grating are disposed by being tilted by 0.3° to 0.5° as described above. Therefore, the position where the number of interference fringes in moire images be minimum in adjustment processing of relative position be the appropriate position, and such relative positional relation of the first grating 14 and the second grating 15 is adjusted at the time of shipment from a factory.

FIG. 6 shows changes in moire images when the relative angle of the first grating 14 and the second grating 15 is changed from the appropriate position (designed value). At the time of shipment from a factory, relative angle between the first grating 14 and the second grating 15 is adjusted so that a moire image having the least number of interference fringes can be obtained as in the moire image indicated with a frame in FIG. 6.

Figure 7:
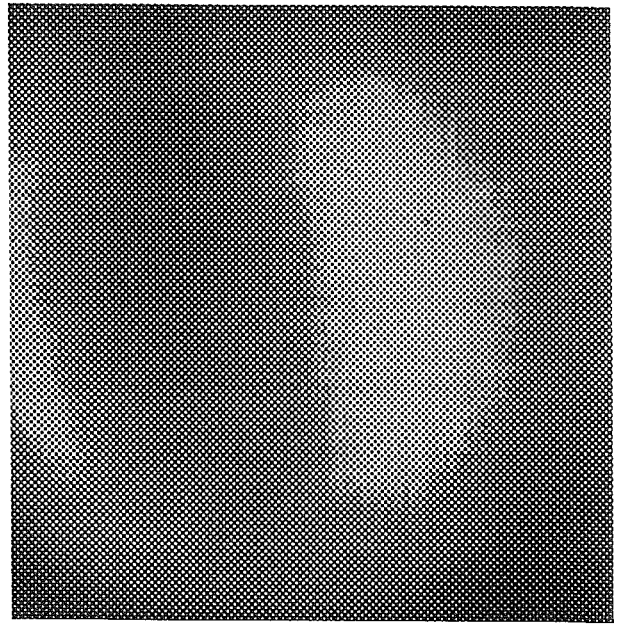
[FIG. 7] This is a diagram showing an image with no interference fringe when the relative angel is set to 0.

On the other hand, when it is set so that the slit directions of the first grating 14 and the second grating 15 are parallel, that is, there is no relative angle set, an operator is to seek for an image position with no moire (zero interference fringe) as shown in FIG. 7 at the time of adjustment. However, when the first grating 14 and the second grating 15 themselves lack uniformity in their cycles (lack of uniformity caused by manufacture variation), moire can occur partially even when the adjusted relative angle is appropriate. Therefore, even though the first grating 14 and the second grating 15 are at their proper positions, an operator needs to adjust their positions again sparing more man hours (time) for adjustment, and at the worst, it will be determined as mal-adjustment.

In contrary, the number of interference fringes can be confirmed easily by an operator, and considering man hour for adjustment, it is preferred to have a configuration where the first grating and the second grating are arranged by being slightly tilted.

Figure 8:
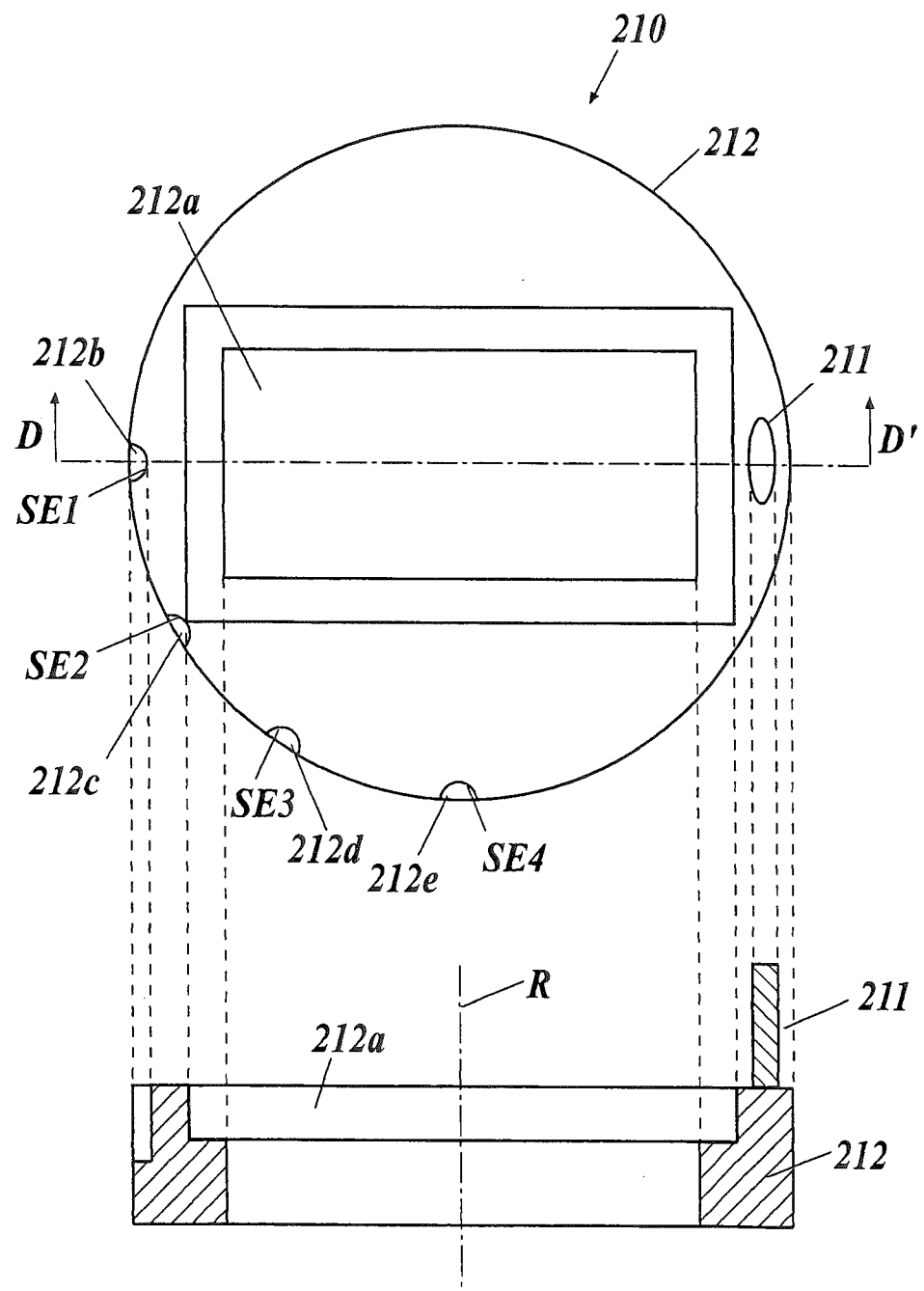
[FIG. 8] This is a plane view and a side view of a grating assembly rotation unit.

Moreover, the X-ray image capturing apparatus 1 is provided with a grating assembly rotation unit 210 (see FIG. 8). Talbot interferometer and Talbot-Lau interferometer have a characteristic that an image of a structure that extends like a line parallel to the slit directions of the first grating 14 and the second gratin 15 cannot be captured clearly. Therefore, angles of the slit directions of the first grating 14 and the second grating 15 need to be adjusted according to the arrangement direction of the structure to be focused in a subject. The grating assembly rotation unit 210 is for rotating the grating assembly 200 around the X-ray emission axis and adjusting the angle of slit direction of the grating assembly 200 with respect to the arrangement direction of the structure to be focused in a subject.

FIG. 8 shows a plane view of the grating assembly rotation unit 210 and a sectional view cut along the line D-D'. As shown in FIG. 8, the grating assembly rotation unit 210 includes a handle 211 and a rotation tray 212. The handle 211 is a protrusion for an operator such as a radiologist to manually rotate the rotation tray 212 by setting the X-ray emission axis (shown by dashed line R in FIG. 8) as the axis. The rotation tray 212 includes an opening 212a for mounting the grating assembly 200 and concave sections 212b to 212e for fixating the rotation angle of the rotation tray 212 by engaging with a ball (see FIGS. 9A and 9B) which is biased by a spring of the after-mentioned tray fixing member 171b. The opening 212a is in a shape and a size the grating assembly 200 can fit from above, and the grating assembly 200 which is mounted in the opening 212a can be rotated around the X-ray emission axis by rotating the rotation tray 212. The concave sections 212b to 212e are provided at relative positions at predetermined rotation angles (here, 0°, 30°, 60°, 90°) from the position preset as being 0° (here, the position where the concave section 212b faces the ball of the tray fixing member 171b is set as the position of) 0°. The concave sections 121b to 212e are provided with angle detection sensors SE1 to SE4, respectively, and an angle detection sensor detects that the corresponding concave section engaged with the tray fixing member 171b and outputs a detection signal to the control unit 181.

In such way, because the grating assembly 200 can be rotated manually, there is no need to have an electric code or such like for rotating the grating assembly 200 within the range a patient can touch and safety can be assured.

Here, in the embodiment, the home position of the grating assembly 200 is set to the position (angle) of the grating assembly 200 when the rotation tray 212 is set at 0°. Further, the home position of the multi-slit 12 is set to the position (angle) where the slit direction of the first grating 14 and the slit direction of the multi-slit 12 are parallel when the grating assembly 200 is at its home position.

Figure 9A:
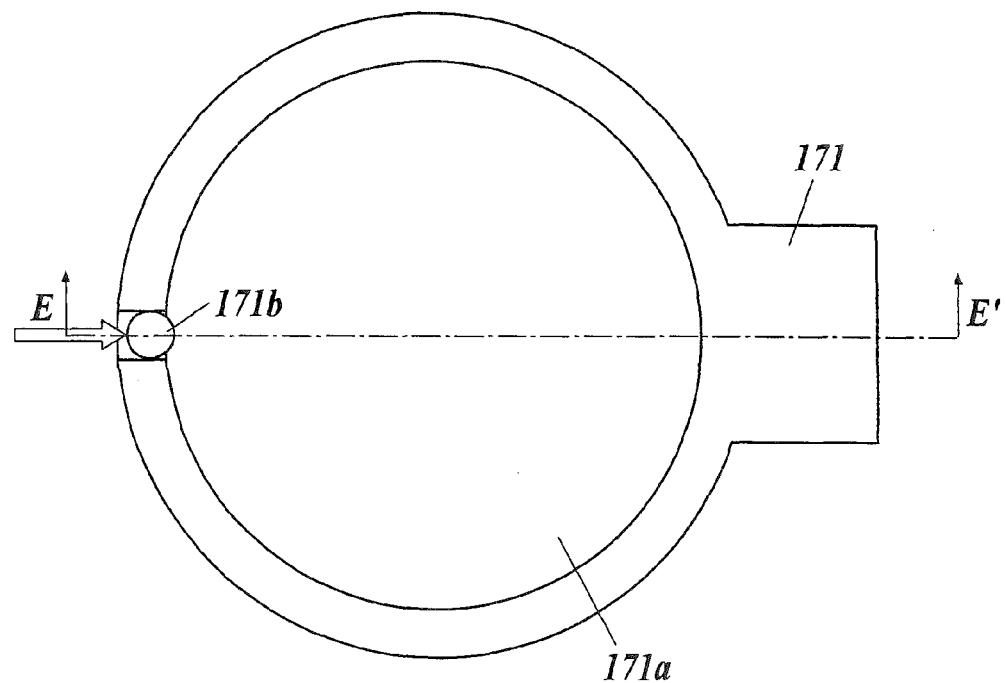
[FIG. 9A] This is a plane view where the holding section of the grating assembly rotation unit in the holding unit shown in FIG. 1, the holding section being enlarged.
Figure 9B:
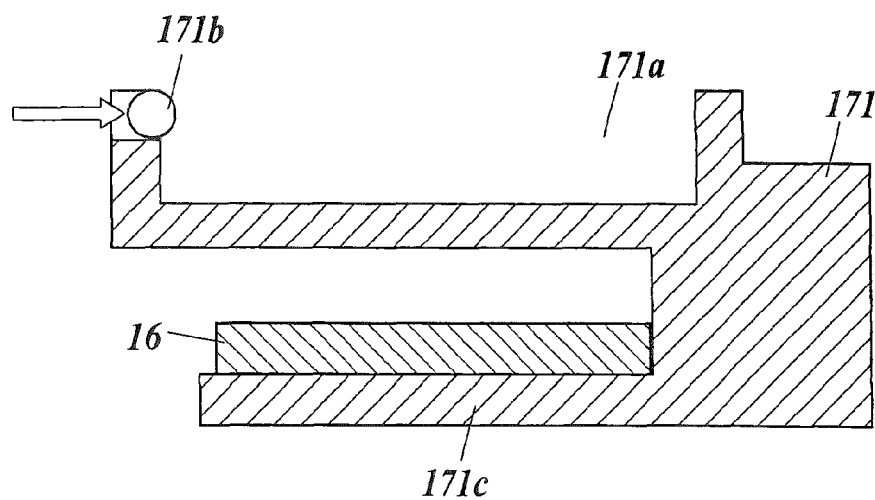
[FIG. 9B] This is a sectional view when cut along E-E' in FIG. 9A.
Figure 9C:
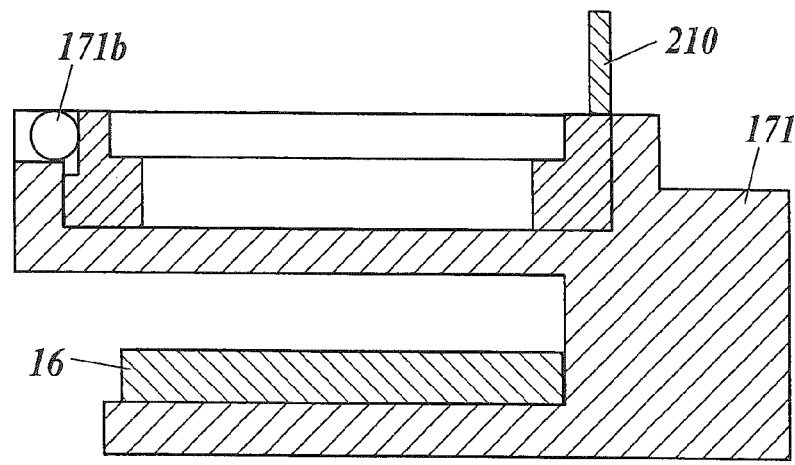
[FIG. 9C] This is a diagram showing a state where the grating assembly rotation unit is held in the holding unit.

FIG. 9A shows a plane view where the holding section 171 of the grating assembly rotation unit 210 in the holding unit 17, the holding section 171 being enlarged, and FIG. 9B shows a sectional view cut along the line E-E' of FIG. 9A. FIG. 9C is a diagram showing a state where the grating assembly rotation unit 210 is held by the holding unit 17.

As shown in FIGS. 9A and 9B, the holding section 171 includes an opening 171a for holding the rotation tray 212 so as to rotate, the opening 171a being formed in a size to be closely engaged with the rotation tray 212, and a tray fixing member 171b for fixating the rotation angle of the rotation tray 212. It is preferred that the portion between the bottom of the opening 171a and the placing section of the X-ray detector 16 is hollow or is formed of aluminum, carbon or the like having high X-ray transmissivity so as not to prevent X-ray transmission. The tray fixing member 171b is configured by including a ball which engages with a concave section that faces the call when one of the concave sections 212b to 212e is positioned so as to face the tray fixing member 171b and a slide guide (a guide of compression spring) for guiding the ball in the direction shown by the arrow in FIGS. 9A and 9B, the slide guide not shown in the drawing. When rotation of the rotation tray 212 stops at the position where any one of the concave sections 212b to 212e faces the tray fixing member 171b, the ball engages with the facing concave section by the slide guide of the tray fixing member 171b and the engaging of the ball is detected by the angle detection sensor (any one of SE1 to SE4) provided in the concave section and a detection signal is to be output to the control unit 181. Thereby, the control unit 181 can detect the rotation angle of the grating assembly 200 from its home position.

Figure 10:
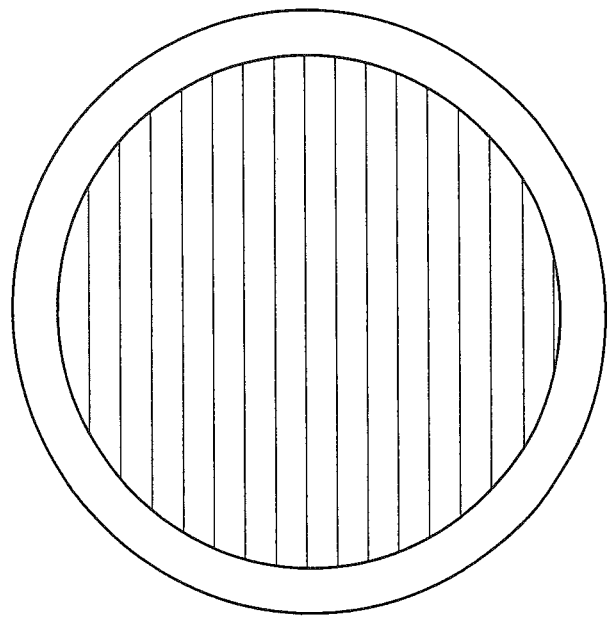
[FIG. 10] This is a diagram showing an example where the first grating and the second grating are in round shape.

Here, the first grating 14 and the second grating 15 may be formed in a round shape as shown in FIG. 10. When the first grating 14 and the second grating 15 are formed in a rectangular shape, the region in which an image of a subject can be captured changes according to the arrangement angle of the gratings with respect to the subject. However, when the gratings are formed in a round shape, the region in which an image of a subject can be captured can be constant regardless of the angel of arrangement of the gratings.

Figure 9D:
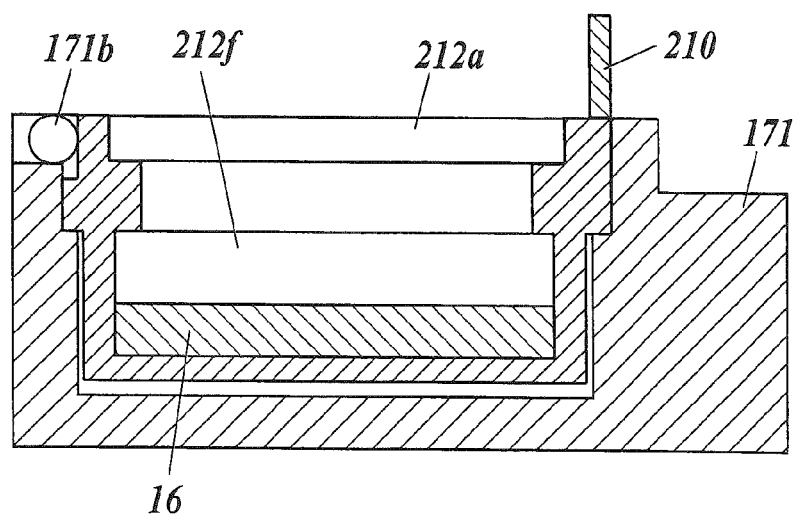
[FIG. 9D] This is a sectional diagram showing a rotation tray which is rotatable integrally with the grating assembly and a X-ray detector.

Further, as shown in FIG. 9D, the mounting unit 212f of the X-ray detector 16 may be provided below the opening 212a of the rotation tray 212 so that the grating assembly 200 and the X-ray detector 16 can rotate integrally. By having such configuration, there is no anisotropic influence on sharpness in horizontal and vertical directions of the X-ray detector 16 (influence of pixel size and opening rate). Therefore, sharpness of reconstruction image in its vertical and horizontal directions can be nearly constant regardless of the rotation angle of the grating assembly 200.

In the X-ray detector 16, conversion elements which generate electric signals according to the X-ray irradiation are two-dimensionally arranged, and the X-ray detector 16 reads electric signals generated by the conversion elements as image signals. Pixel size in the X-ray detector 16 is 10 to 300 (μm), and more preferably, 50 to 200 (μm).

It is preferable that the X-ray detector 16 is fixed at a position in the holding unit 17 so as to abut the second grating 15. This is because as the distance between the second grating 15 and the X-ray detector 16 becomes longer, moire image obtained by the X-ray detector 16 becomes fuzzier.

As for the X-ray detector 16, a FPD (flat panel detector) can be used. There are indirect conversion type FPD which converts X-rays to electric signals by photoelectric conversion via a scintillator and direct conversion type FPD which converts X-rays directly to electric signals. Either of the both types can be used.

In the indirect conversion type, pixels are two dimensionally arranged along with photoelectric elements (thin film transistors) below a scintillator plate such as CsI and $Gd_2O_2$. When the X-rays entered the X-ray detector 16 are absorbed by the scintillator plate, the scintillarot plate emits light. By the emitted light, electric charges are accumulated in each photoelectric conversion element and the accumulated electric charges are read out as an image signal.

In the direct conversion type, an amorphous selenium film of 100 to 1000 (μm) film thickness is formed on a glass by thermal deposition of amorphous selenium and an amorphous selenium film and electrodes are deposited on the two dimensionally arranged TFT array. When the amorphous selenium film absorbs X-rays, voltage is liberated into an object in a form of electron-hole pair and the voltage signals between the electrodes are read by TFTs.

Here, image capturing device such as a CCD (Charged Coupled Device) and a X-ray cameral can be used as the X-ray detector 16.

A series of processing performed by FPD at the time of X-ray image capturing will be described.

First, FPD carries out reset to remove unnecessary electric charges that remain after the previous image capturing (reading). Thereafter, accumulation of electric charges is carried out at the timing when X-ray emission is started and the accumulated electric changes are read as image signals at the timing when X-ray emission is stopped. Here, right after the rest or after reading of the image signals, dark reading by which voltage values of the accumulated electric charges are detected is carried out.

As shown in FIG. 11, the main body 18 includes a control unit 181, an operation unit 182, a display unit 183, a communication unit 184 and a storage unit 185.

The control unit 181 includes a CPU (Central Processing Unit), a RAM (Random Access Memory) and the like, and the control unit 181 executes various types of processing in cooperation with the programs stored in the storage unit 185. For example, the control unit 181 executes various types of processing including the after-mentioned image capturing control processing A.

In addition to a radiation switch and a group of keys used for input operations of image capturing conditions and the like, the operation unit 182 includes a touch panel which is integrally formed with a display of the display unit 183, and the operation unit 182 generates operation signals according to operations of the above and outputs the operation signals to the control unit 181.

In compliance with the display control of the control unit 181, the display unit 183 displays an operation screen, operation condition of the X-ray image capturing apparatus 1 and the like on the display.

The communication unit 184 includes a communication interface and communicates with the controller 5 on a network. For example, the communication unit 184 sends a moire image which is read by the X-ray detector 16 and stored in the storage unit 185 to the controller 5.

In the storage unit 185, programs to be executed by the control unit 181 and data needed for execution of the programs are stored. Further, a moire image obtained by the X-ray detector 16 is stored in the storage unit 185.

The controller 5 controls image capturing operation of the X-ray image capturing apparatus 1 in accordance with operation performed by an operator and forms a reconstruction image of a subject for diagnosis by using a plurality of moire images obtained by the X-ray image capturing apparatus 1. In the embodiment, an example using the controller 5 as the image processing apparatus which forms a reconstruction image of subject is described. However, an image processing apparatus which is dedicated for performing various types of image processing on X-ray image can be connected with the X-ray image capturing apparatus 1 to form a reconstruction image by such image processing apparatus.

Figure 12:
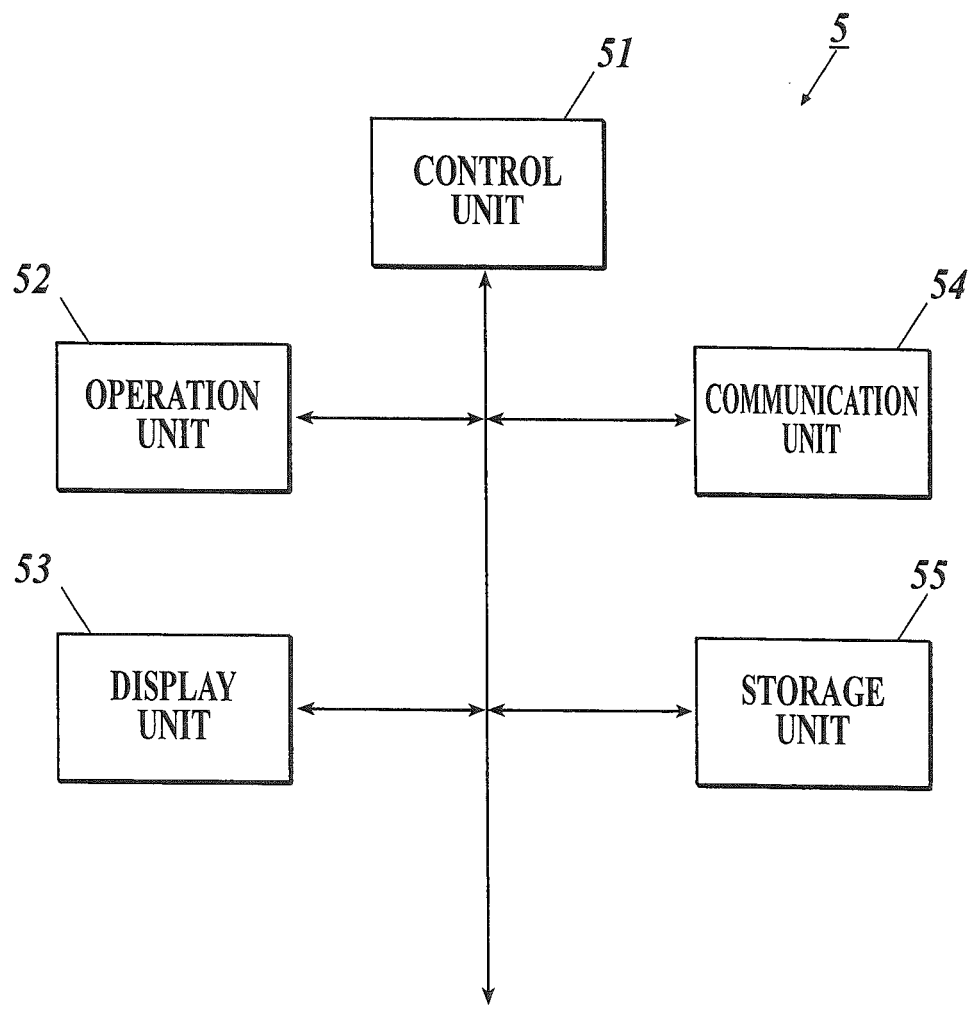
[FIG. 12] This is a block diagram showing a functional structure of a controller.

As shown in FIG. 12, the controller 5 includes a control unit 51, an operation unit 52, a display unit 53, a communication unit 54 and a storage unit 55.

The control unit 51 includes a CPU (Central Processing Unit), a RAM (Random Access Memory) and the like, and the control unit 51 executes various types of processing including the after-mentioned diagnosis image forming processing A in cooperation with the programs stored in the storage unit 55.

The operation unit 52 includes a key board including a cursor key, number input keys, various types of function keys and the like and a pointing device such as a mouse, and the operation unit 52 outputs pressed signals of keys pressed on the key board and operation signals of the mouse to the control unit 51 as input signals. The display unit 53 may include a touch panel which is integrally formed with a display and may generate operation signals corresponding to the operations of the touch panel and output the signals to the control unit 51.

For example, the display unit 53 includes a monitor such as CRT (Cathode Ray Tube) or LCD (Liquid Crystal Display), and the display unit 53 displays operational screens, operation conditions of the X-ray image capturing apparatus 1, formed subject reconstruction images and the like in accordance with display control of the control unit 51.

The communication unit 54 includes a communication interface and communicates with the X-ray image capturing apparatus 1 and the X-ray detector 16 on a network through wired communication or wireless communication. For example, the communication unit 54 sends image capturing conditions and control signals to the X-ray image capturing apparatus 1 and receives moire images from the X-ray image capturing apparatus 1 or the X-ray detector 16.

In the storage unit 55, programs to be executed by the control unit 51 and data needed for executing the programs are stored. Fore example, image capturing order information indicating orders reserved by RIS, HIS and reservation devices which are not shown in the drawing is stored in the storage unit 55. The image capturing order information is information such as patient name, imaging parts, image capturing methods and the like. In the storage unit 55, moire images obtained by the X-ray detector 16 and a subject reconstruction image for diagnosis formed on the basis of the moire images are stored by being associated with respective image capturing order information.

Moreover, gain correction data, defective pixel map and the like corresponding to the X-ray detector 16 are stored in the storage unit 55 in advance.

In the controller 5, when a list display of image capturing order information is instructed by an operation of the operation unit 52, the control unit 51 reads out the image capturing order information from the storage unit 55 and displays the image capturing order information in the display unit 53. When image capturing order information is specified by the operation unit 52 (in the case of cassette type X-ray detector 16, when a cassette ID which is identification information of the cassette to be used for image capturing is further specified), setting information regarding image capturing conditions corresponding to the specified image capturing order information, warm-up instruction of X-ray source 11 and the like are sent to the X-ray image capturing apparatus 1 by the communication unit 54. Further, when the X-ray detector is a cable-less cassette type FPD apparatus, it is activated to be in an image capturing state from a sleep state which is a state for preventing consumption of inner battery.

In the X-ray image capturing apparatus 1, preparation of X-ray image capturing is to be executed when the setting information of image capturing conditions and the like are received by the communication unit 184 from the controller 5.

X-ray image capturing method using Talbot-Lau interferometer of the above described X-ray image capturing apparatus 1 will be described.

Figure 13:
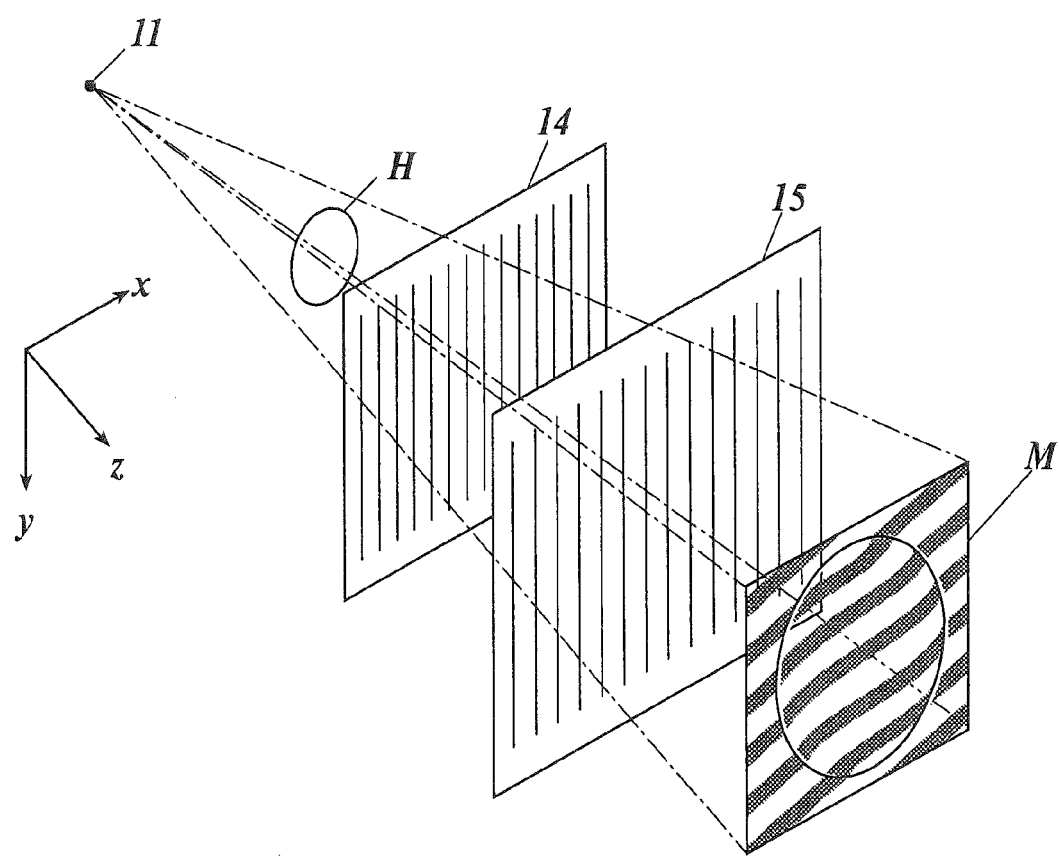
[FIG. 13] This is a diagram which explains the principle of Talbot interferometer.

As shown in FIG. 13, when the X-rays emitted from the X-ray source 11 pass through the first grating 14, the passed X-rays form images at constant intervals in z direction. These images are called self images, and this phenomenon where self images are formed is called Talbot effect. The second grating 15 is disposed at the position where a self image is formed in parallel and the grating direction of the second grating 15 is slightly tilted from the position parallel with the grating direction of the first grating 14. Therefore, a moire image M is obtained by the X-rays passed through the second grating 15. When a subject H exists between the X-ray source 11 and the first grating 14, phases of X-rays deviate due to the subject H, and therefore, the interference fringes in the moire image M are disturbed bordering the margin of the subject H as shown in FIG. 13. This disturbance in interference fringes can be detected by processing the moire image M and an image of the subject can be formed. This is the principle of Talbot interferometer and Talbot-Lau interferometer.

In the X-ray image capturing apparatus 1, the multi-slit 12 is disposed between the X-ray source 11 and the first grating 14 at a position near the X-ray source 11 and image capturing by Talbot Lau interferometer is performed. Although it is assumed that the X-ray source 11 is an ideal point source in Talbot interferometer, focus point having focus diameter that is large to a certain extent is used in the actual image capturing. Therefore, by the multi-slit 12, it becomes like a multiple light source where X-rays are emitted by a plurality of point sources being connected. This is the X-ray image capturing method using Talbot-Lau interferometer, and the same Talbot effect as in Talbot interferometer can be obtained even when focus diameter is large to a certain extent.

In a conventional Talbot-Lau interferometer, the multi-slit 12 is used to make the point source be multi light source as described above and to increase exposure dose, and the first grating 14 or the second grating 15 has been subjected to relative displacement in order to obtain a moire image by fringe-scanning. However, in the embodiment, instead of the first grating 14 or the second grating 15 being subjected to relative displacement, the multi-slit is moved with respect to the first grating 14 and the second grating 15 to obtain a plurality of moire images at constant cycle intervals while the positions of the first grating 14 and the second grating 15 being fixed.

Figure 14A:
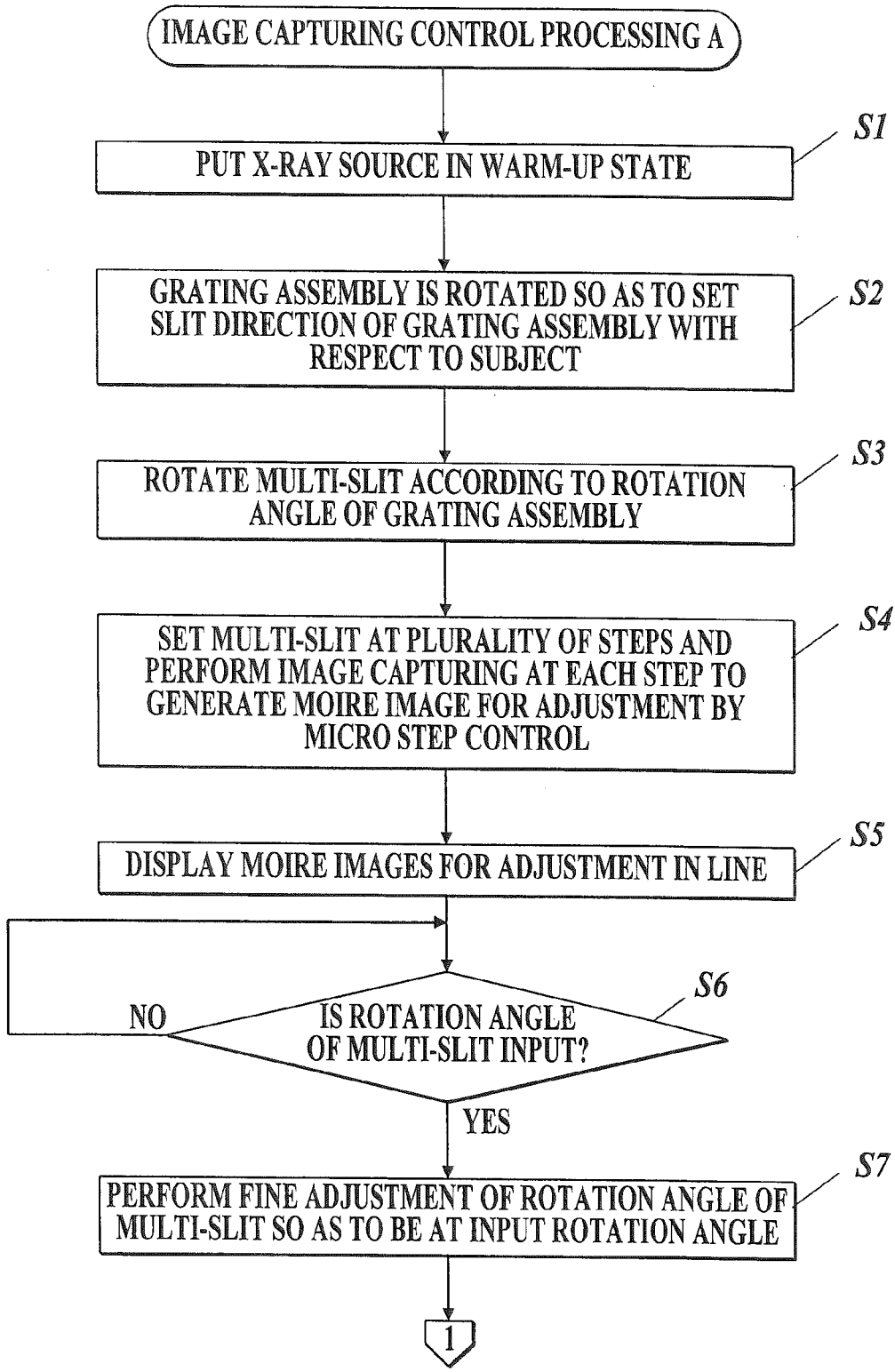
[FIG. 14A] This is a flowchart showing image capturing control processing A executed by the control unit of the X-ray image capturing apparatus.
Figure 14B:
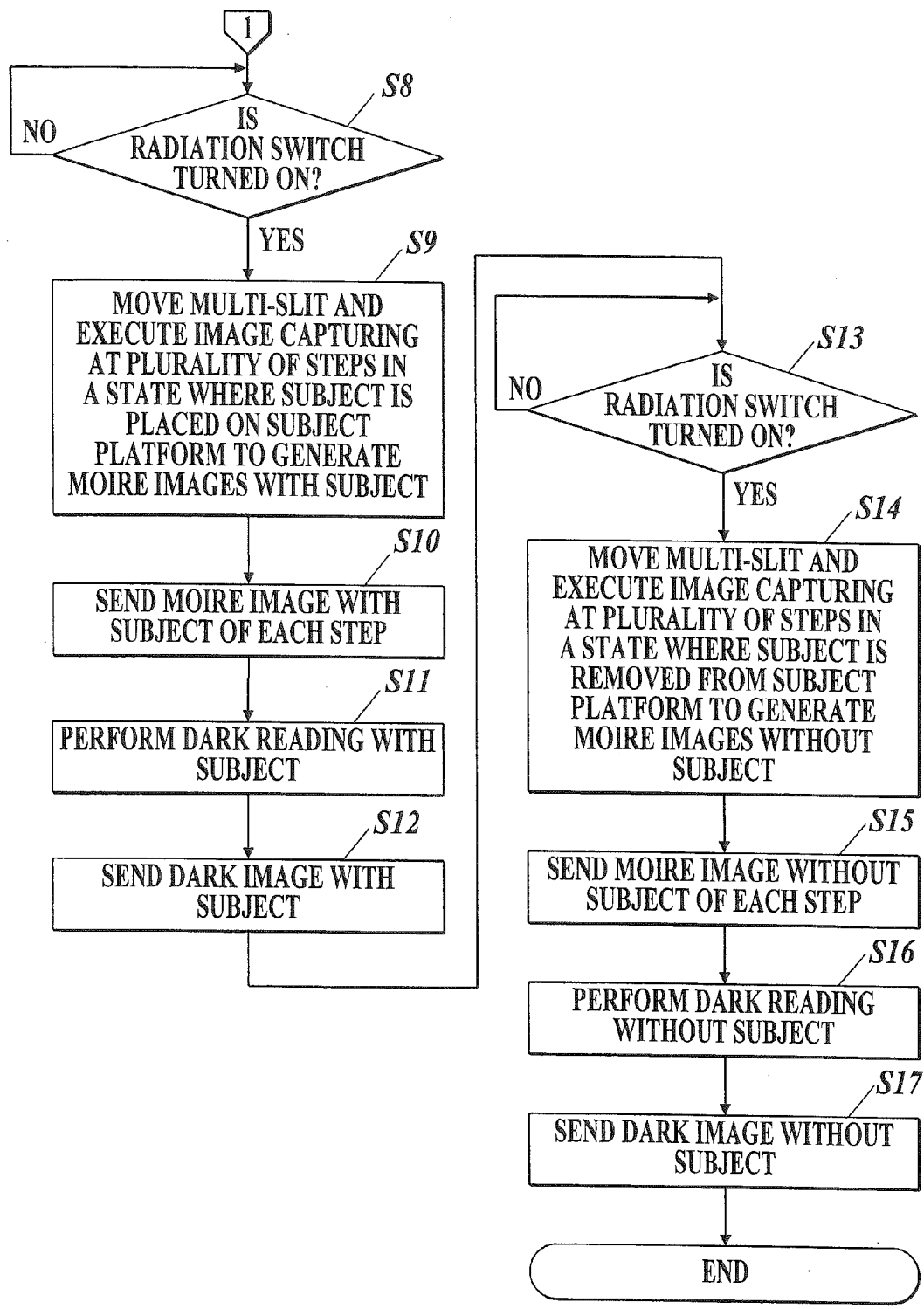
[FIG. 14B] This is a flowchart showing image capturing control processing A executed by the control unit of the X-ray image capturing apparatus.

FIGS. 14A to 14B are flowcharts showing the image capturing control processing A which is executed by the control unit 181 of the X-ray image capturing apparatus 1. The image capturing control processing A is executed by the control unit 181 and the programs stored in the storage unit 185 cooperating with each other.

Here, the above described X-ray image capturing method using Talbot-Lau interferometer is used for X-ray image capturing and the fringe-scanning is used for reconstruction of subject image. In the X-ray image apparatus 1, the multi-slit 12 is moved in step-wise manner wherein a plurality of steps are provided equally apart from each other, and image capturing is performed at each step to obtain a moire image for each step.

The number of steps is set to 2 to 20, and more preferably, 3 to 10. In terms of obtaining a reconstruction image having high visibility, it is preferred to have 5 steps (reference document (1) K. Hibino, B. F. Oreb and D. I. Farrant, Phase shifting for nonsinusoidal wave forms with phase-shift errors, J. Opt. Soc. Am. A, Vol. 12, 761-768 (1995), reference document (2) A. Momose, W. Yashiro, Y. Takeda, Y. Suzuki and T. Hattori, Phase Tomography by X-ray Talbot Interferometetry for biological imaging, Jpn. J. Appl. Phys., Vol. 45, 5254-5262 (2006)).

As shown in FIG. 14A, first, the X-ray source 11 is switched to a warm-up state by the control unit 181 (step S1).

Next, the grating assembly 200 is rotated according to an operation by an operator and the slit direction of the grating assembly 200 with respect to a subject is set (step S2). That is, an operator such as a radiologist rotates the handle 211 of the grating assembly rotation unit 210 and sets the slit direction of the grating assembly 200 according to the arrangement direction of the structure to be focused in the subject placed on the subject platform 13. When the rotation of the handle 211 is stopped and the position is fixed by the engagement of a ball of the tray fixing member 171b which is biased by a spring, a detection signal is output to the control unit 181 from any one of the angle detection sensors SE1 to SE4 and rotation angle of the grating assembly 200 from the home position corresponding to the set slit direction is obtained in the control unit 181.

Next, according to the rotation angle of the grating assembly 200, the motor unit 121a of the multi-slit rotation unit 121 is controlled by pulse to rotate the multi-slit 12 according to the rotation angle of the grating assembly 200 (step S3). For example, the pulse motor of the motor unit 121a is controlled and the multi-slit 12 is moved from its home position for rotation angle which is close to the rotation angle of the grating assembly 200 at once (for example, to about 29° when the grating assembly 200 is set to 30°).

Next, the motor unit 121a is switched to a micro-step precise control and image capturing is performed are a plurality of rotation angles while gradually rotating the multi-slit 12 to generate a plurality of moire images for adjustment (step S4). For example, the multi-slit 12 is set at three rotation angles which are 29.5°, 30° and 30.5° and low X-ray is emitted from the X-ray source 11 to carry out image capturing. In such way, three moire images for adjustment are obtained. Here, in step S4, image capturing is carried out in a state where a subject is not placed on the subject platform 13.

The moire images for adjustment are aligned and displayed in the display unit 183 being associated with the rotation angles of the multi-slit 12, respectively (step S5).

Here, as described above, the relative angle of the first grating 14 and the second grating 15 is adjusted at the time of shipment from a factory so that the number of interference fringes be minimum. Therefore, in step S2, the grating assembly 200 is rotated while maintaining the relative angle as shown in FIG. 15. However, when the grating assembly 200 is rotated and the relative angle of the multi-slit 12 and the grating assembly 200 changes, sharpness of interference fringes (that is, moire) changes as shown in FIG. 16. Therefore, the relative angle of the multi-slit 12 and the grating assembly 200 needs to be adjusted.

Generally, as shown in FIG. 16, smaller the relative angle of the multi-slit 12 and the grating assembly 200, moire images having sharper interference fringes can be obtained. FIG. 16 shows moire images when relative angle of the grating assembly 200 and the multi-slit 12 is 0°, 2° and 10°. That is, when the grating assembly 200 rotates for 30° as shown in FIG. 15, it is preferred that the multi-slit 12 is rotated for 30°. However, the multi-slit 12 is easily affected by heat because it is disposed near the X-ray source 11 which is a heating unit. Therefore, considering deformation and such like of the multi-slit 12, it is effective that the motor unit 121a is mucrostep driven to carry out fine adjustment of steps S4 to S7 and not merely rotating the multi-slit 12 for the same angle as the grating assembly 200.

An operator observes them moire image displayed in the display unit 183 in step S5 and selects the rotation angle which gives the sharpest interference fringes as the rotating angle used for image capturing. Here, sharpness of interference fringes is visually observed by an operator. However, definition which indicates the degree of sharpness of interference fringes can be expressed by the following formula when the maximum value in the after-mentioned sine-curve (see FIG. 22) is MAX and the minimum value thereof is MIN.

Definition of interference fringes=(MAX−MIN)/(MAX+MIN)=amplitude/average value

When the rotation angle of the multi-slit 12 is input by the operation unit 182 (step S6; YES), the motor unit 121a is driven again and the position of the multi-slit 12 is adjusted finely so that the rotating angle of the multi-slit 12 from its home position be the input rotation angle (step S7).

After adjusting rotation angle of the multi-slit 12, a subject is placed on the subject platform 13 and the radiation switch is operated to be turned ON by an operator (step S8; YES), the multi-slit 12 is moved in the slit aligning direction by the drive unit 122 to executed image capturing at a plurality of steps and a plurality of moire images with subject are generated (step S9).

First, emission of X-rays by the X-ray source 11 is started in a state where the multi-slit 12 is stopped. After reset, electric charges are accumulated at the timing of X-ray emission in the X-ray detector 16, and the accumulated electric charges are read as image signals at the timing when X-ray emission is stopped. This is image capturing of one step. At the timing when image forming of one step is completed, the multi-slit 12 starts to move and stops after moving for a predetermined amount, and image capturing of next step is to be performed. In such way, moving and stopping of the multi-slit 12 is repeated for a predetermined number of steps, and X-rays are emitted and image signals are read when the multi-slit 12 stops. The read image signals are output to the main body 18 as moire images.

For example, image capturing of five steps is to be performed in 10 seconds wherein the slit cycle of the multi-slit 12 is 22.8 (μm). Image capturing is performed every time after the multi-slit 12 moves for 4.56 (μm) corresponding to ⅕ of its slit cycle and stops.

When the second grating 15 (or the first grating) is to move as in a conventional manner, slit cycle of the second grating 15 is to be relatively small and moving amount in each step is also to be small. However, slit cycle of the multi-slit 12 is relatively larger than that of the second grating 15 and moving amount in each step is also larger. For example, as oppose to moving amount in each step of the second grating 15 having slit cycle of 5.3 (μm) being 1.06 (μm), moving amount of the multi-slit 12 having slit cycle of 22.8 (μm) is 4.56 (μm), which is about four times the moving mount of the second grating. When the same drive transmission system (including a drive source and a deceleration transmission system) is used and image capturing is performed by repeating activation and termination of the drive unit 122 when performing image capturing of each step, ratio of moving amount error due to the influence of backlash of the drive unit 122 at the time of activation and termination in the actual moving amount corresponding to the controlled variable (number of drive pulses) of the pulse motor (drive source) for moving becomes smaller in the method where the multi-slit 12 is moved as in the embodiment. This indicates that a moire image which follows the after-mentioned sine-curve can be easily obtained and that a high resolution reconstruction image can be obtained even when activation and termination are repeated. Alternatively, this indicates that when an image of conventional format is sufficiently suited for diagnosis, accuracy (especially, activation characteristic and termination characteristic) in the entire drive transmission system including a motor (drive source) can be alleviated to reduce the cost of components constituting the drive transmission system.

When image capturing of each step is completed, moire image of each step is sent to the controller 5 from the communication unit 184 of the main body 18 (step S10). Moire image with subject is sent one by one to the controller 5 from the main body 18 every time image capturing of a step is completed.

Next, dark reading is performed in the X-ray detector 16 and a dark image for correcting image data with subject is obtained (step S11). Dark reading is performed at least once. Alternatively, dark reading may be performed for number of times to obtain the average value thereof as a dark image. The dark image is sent to the controller 5 from the communication unit 18 (step S12). Off-set correction data based on the dark reading is commonly used for correction of each moire image signal.

Here, as for obtaining a dark image, dark reading of each step can be performed after a moire image is obtained at each step and off-set correction data dedicated to each step can be generated. When an interval between image capturing of each step is short and there is no time for off-set correction, dark reading may be performed only at the image capturing of the first step to obtain off-set correction value and the correction value can be sued for image capturing of steps thereafter.

Next, the processing is to be in a waiting state for an operator to turn ON the radiation switch (step S13). Here, an operator removes a subject from the subject platform 13 and evacuates the patient so that moire images without subject can be formed. When it is ready for image capturing without subject, the radiation switch is pressed.

When the radiation switch is pressed (step S13; YES), the multi-slit 12 is moved in its slit aligning direction by the drive unit 122 and image capturing is executed at a plurality of steps without subject and a plurality of moire images without subject are generated (step S14). When image capturing of each step is finished, moire image of each step is sent to the controller 5 from the communication unit 184 of the main body 18 (step S15). The moire images without subject are transmitted one by one to the controller 5 form the main body 18 by the communication unit 184 every time image capturing of each step is finished.

Next, dark reading is performed in the X-ray detector 16 to obtain a dark image without subject (step S16). Dark reading is performed at least once. Alternatively, dark reading may be performed for number of times to obtain the average value thereof as a dark image. The dark image is sent to the controller 5 from the communication unit 184 (step S17), and a series of image capturing with respect to one image capturing order is completed.

Here, as for obtaining of a dark image, dark reading of each step may be performed after a moire image is obtained for each step and off-set correction data dedicated for each step may be generated.

In the controller 5, when the moire images are received by the communication unit 54, the received moire images are stored in the storage unit 55 by being associated with the image capturing order information specified at the start og image capturing.

Figure 17:
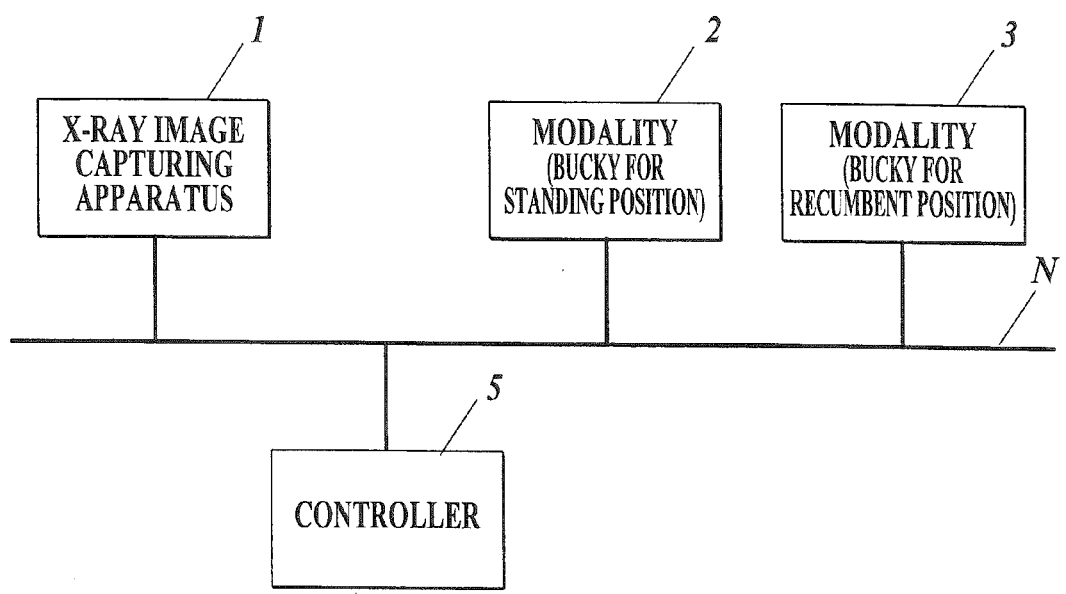
[FIG. 17] This is a diagram showing a system configuration when the controller is commonly used with other modalities.

Here, when the controller 5 is not exclusively for the X-ray image capturing apparatus 1 using Talbot interferometer and commonly used by other modalities such as a bucky for standing position, a bucky for recumbent position and the like that can be used by loading a cassette type FPD as shown in FIG. 17, there is a possibility that an error such as there is no image capturing order information to be associated with when the second moire image and thereafter are sent when a plurality of moire images are sent to the controller 5 one at a time every time a moire image is captured by the X-ray image capturing apparatus 1 because one image is to be associated with one image capturing order information (one image is to be associated with one or a plurality of dark reading data for off-set correction depending on the circumstances) at the time of image capturing by other modalities. Therefore, in the case of such system configuration, it is preferable that a plurality of moire images (including a dark image depending on the circumstances) are combined as a series of related image set and sent to the controller 5. This is to say, for example, if a memory which can temporarily store a plurality of read data is provided in a cassette type FPD apparatus, read data can be sequentially stored in the memory in each image capturing and the read image can be sent all together after the last data is read. Alternatively, configuration may be such that when the controller 5 recognizes that modality information for using Talbot image capturing apparatus is included in image capturing order information, the controller 5 temporarily stores the read data transmitted from the cassette type FPD apparatus for every image capturing by associating with the image capturing order information. Further, configuration may be such that when a reconstruction image is generated on the basis of the read data, the reconstruction image is stored by being associated with the image capturing order information and the temporarily stored read data is deleted.

Moreover, in a case where the X-ray detector 16 is a cassette type FPD apparatus and the X-ray detector 16 sends the read images directly to the controller 5 through wireless communication, when the X-ray detector 16 is once loaded in a modality including the X-ray image capturing apparatus 1, the control unit of such apparatus cannot control the sending method of images. Therefore, when configuration is such that (1) a send button for an operator to instruct sending is provided in a cassette, (2) in the controller 5, image capturing order information is specified by the operation unit 52 and input of the modality and the cassette ID used for image capturing is received, and an operation mode (general mode, Talbot mode) according to the modality to be used in image capturing with respect to the specified cassette is set by the control unit 51 and (3) in Talbot mode, a series of relating image set stored in the cassette is sent by the send button of the cassette being the trigger after image capturing, images can be transmitted to the controller 5 in a sending method according to the modality.

Figure 18:
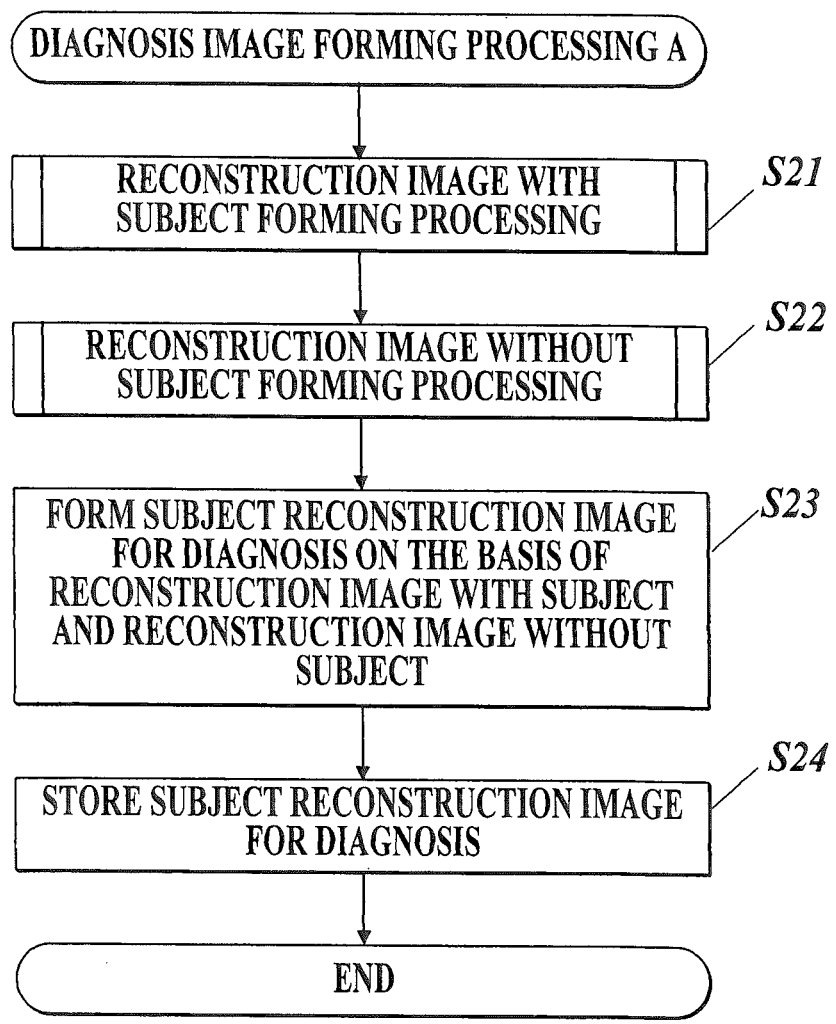
[FIG. 18] This is a flowchart showing diagnosis image forming processing A executed by a control unit of the controller.

FIG. 18 is a flowchart showing the diagnosis image forming processing A which is executed by the control unit 51 of the controller 5 after the moire images are received. The diagnosis image forming processing A is executed by the control unit 51 and the programs stored in the storage unit 55 cooperating with each other.

First, the reconstruction image with subject forming processing is executed and a reconstruction image with subject is formed from a plurality of moire images with subject (step S21). Next, the reconstruction image without subject forming processing is executed and a reconstruction image without subject is formed from a plurality of moire images without subject (step S22). Then, on the basis of the reconstruction image with subject and the reconstruction image without subject, a subject reconstruction image for diagnosis is formed (step S23). The formed subject reconstruction image is stored in the storage unit 55 by being associated with the specified image capturing order information (step S24).

Figure 19:
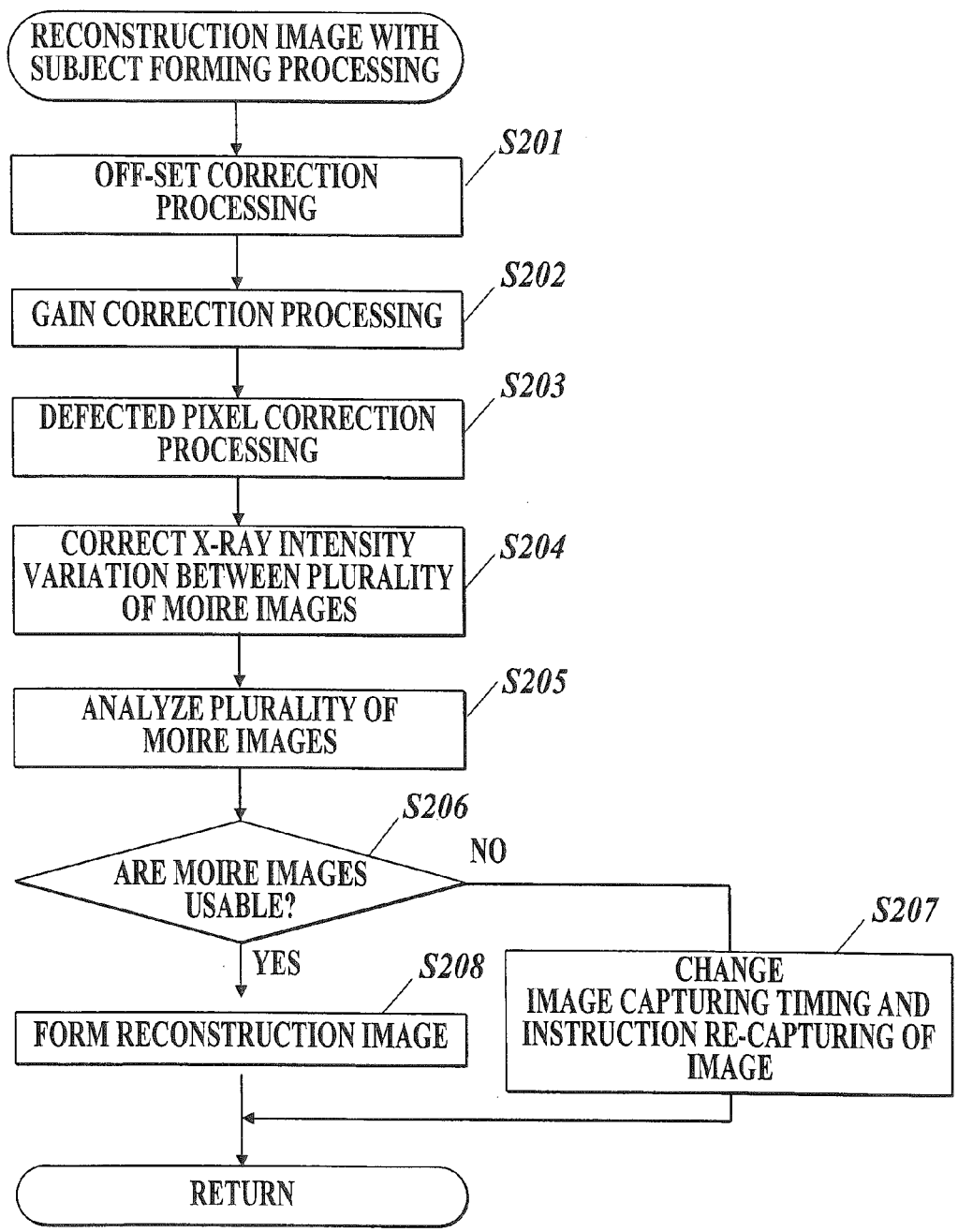
[FIG. 19] This is a flowchart showing reconstruction image with subject forming processing executed by the control unit of the controller.

FIG. 19 is a flowchart showing the flow of the reconstruction image with subject forming processing which is executed in step S21.

First, in steps S201 to S5203, correction processing for correcting variations among pixels of the X-ray detector 16 with respect to the plurality of moire images with subject is executed. In particular, off-set correction processing (step S201), gain correction processing (step S202) and defected pixel correction processing (step S203) are executed.

Here, in the present invention, reconstruction image for diagnosis is generated according to the flow shown in FIG. 18. Therefore, the absolute output value of each pixel itself does not affect the image quality of the reconstruction image. Thus, special adjustment and the like for Talbot image capturing is not needed to be performed on correction data for gain correction processing and the correction data for gain correction processing may be data obtained by a general gain calibration which is performed by using a vessel for the standing position bucky or a vessel for the recumbent position bucky. Cassette type FPD apparatus is generally expensive and therefore, it is preferred that an apparatus for such general simple image capturing can be commonly used when considering introduction cost for using such cassette type FPD apparatus in a facility.

In step S201, off-set correction is performed on each moire image on the basis of the dark image for correcting image data with subject.

In step S202, gain correction data corresponding to the X-ray detector 16 used for the image capturing is read out from the storage unit 55 and gain correction is performed on each moire image on the basis of the read out gain correction data.

In step S203, a defected pixel map (data indicating positions of defected pixels) corresponding to the X-ray detector 16 used for the image capturing is read out from the storage unit 55 and the pixel values (signal values) at the position indicated in the defected pixel position map of each moire image are to be subjected to interpolation calculation by their surrounding pixels.

Next, X-ray intensity variations correction (trend correction) is performed between the plurality of moire images (step S204). In Talbot image capturing, one subject reconstruction image is formed on the basis of a plurality or moire images. Therefore, if there is fluctuation (variations) among X-ray intensity emitted in image capturing of each of the moire images, an accurate subject reconstruction image cannot be obtained, and minute changes in signals can be overlooked. Therefore, instep S204, processing for correcting differences in signal values caused by variations in X-ray intensity during image capturing among the plurality of moire images is carried out.

The specific processing can be any of a correction method using a signal value of a pixel at one point predetermined in each moire image, a correction method (one dimensional correction) of correcting signal value differences in a predetermined direction of the X-ray detector 16 between each of the moire images and a correction method (two dimensional correction) of correction signal value differences in two dimensional directions between each of the moire images.

Figure 20:
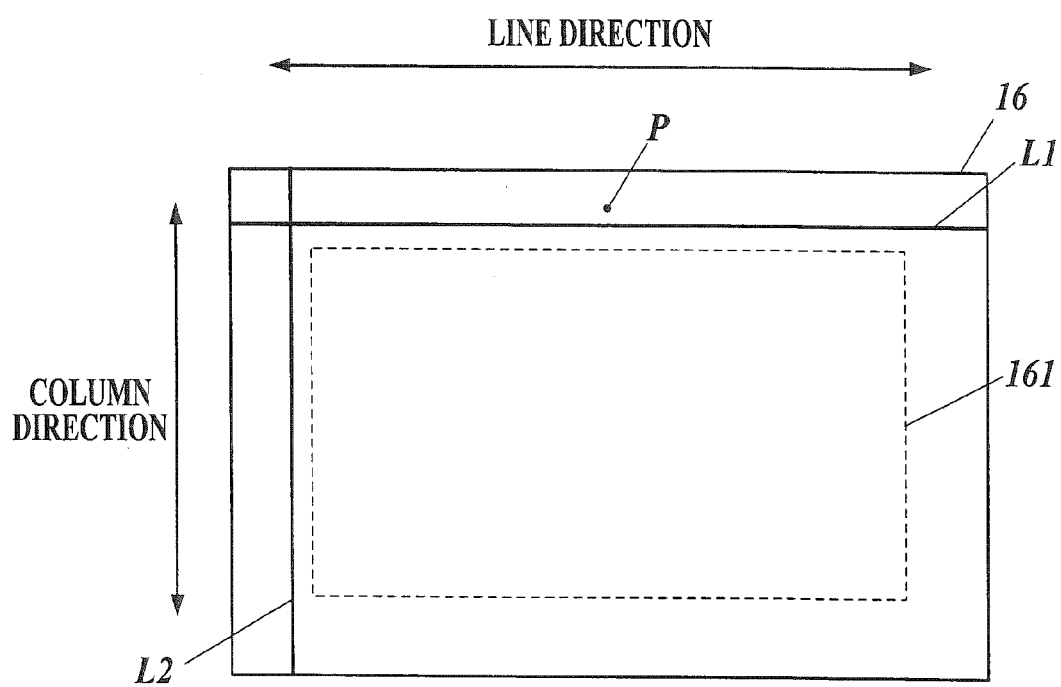
[FIG. 20] This is a diagram for explaining correction of variations in X-ray intensity between a plurality of moire images.

In the correction method using a signal value of a pixel at one point, first, the signal value of a pixel at the preset position P that corresponds to the direct X-ray region outside of the moire fringe region (subject arrangement region) 161 in the X-ray detector 16 is obtained for each of the plurality of moire images as shown in FIG. 20. Next, the first moire image is standardized by the average signal value of the pixels at the position P in the second moire image and thereafter obtained above, and correction coefficient of each of the moire images which are the second moire image and thereafter is calculated on the basis of the value at position P after standardization. Then, by the correction coefficient being multiplied to each or the moire images which are the second moire image and thereafter, X-ray intensity variations are corrected. In such correction method, the overall variations in X-ray intensity between each image capturing can be corrected easily. Here, a detection device such as a sensor for detection X-ray exposure dose can be provided on the back of the X-ray detector 16, and signal value differences caused by variations in X-ray intensity during image capturing among the moire images may be corrected on the basis of the X-ray exposure dose during image capturing of each of the moire image output from the detection device.

In the primary correction, first, in each of the plurality of moire images, average signal value of pixels in the preset line L1 (line means the reading line direction in the X-ray detector 16) is calculated. Next, the first moire image is standardized by the average signal value of pixels in the second moire image and thereafter, and correction coefficient in line direction of each of the moire images which are the second moire image and thereafter is calculated on the basis of signal value of each pixel in the line L1 after standardization and signal value of each pixel in lines L1 of the second moire image and thereafter. Then, by multiplying the correction coefficient corresponding to the position in line direction to each of the moire images which are the second moire image and thereafter, X-ray intensity variations in line direction can be corrected. This correction method can easily correct variations in X-ray intensity in one dimensional direction between each image capturing. For example, in an image capturing, when there is a time rag between the emission timing by the X-ray source 11 and the reading timing of the X-ray detector 16, X-ray intensity variations and the like in reading line direction of the X-ray detector 16 that occurs due to the above time rag can be corrected.

In the two dimensional correction, in each of the plurality of moire images, average signal values of pixels in the predetermined line L1 and column L2 (column means the direction orthogonal to reading line direction in the X-ray detector 16) are calculated, first. Next, the first moire image is standardized by the average signal values of pixels in line L1 of the second moire image and thereafter, and correction coefficient in line direction of each of the moire images which are the second moire image and thereafter is calculated on the basis of the signal values of pixels in line L1 after standardization and signal values of pixels in lines L1 in the second moire images and thereafter. Similarly, the first moire image is standardized by the average signal value of pixels in lines L2 in the second moire image and thereafter, and correction coefficient in column direction for each of the moire images which are the second moire image and thereafter is calculated on the basis of signal values of pixels in column L2 after standardization and signal values of pixels in columns 2 in the second moire image and thereafter. Then, the correction coefficient in line direction is multiplied by the correction coefficient in column direction to calculate correction coefficient of each pixel in each of second moire image and thereafter. Thereafter, by each pixel being multiplied by the correction coefficient in line direction and the correction coefficient in column direction, X-ray intensity variations in two dimensional directions is corrected. In this correction method, X-ray intensity variations in two dimensional directions between each image capturing can be corrected easily.

Figure 21:
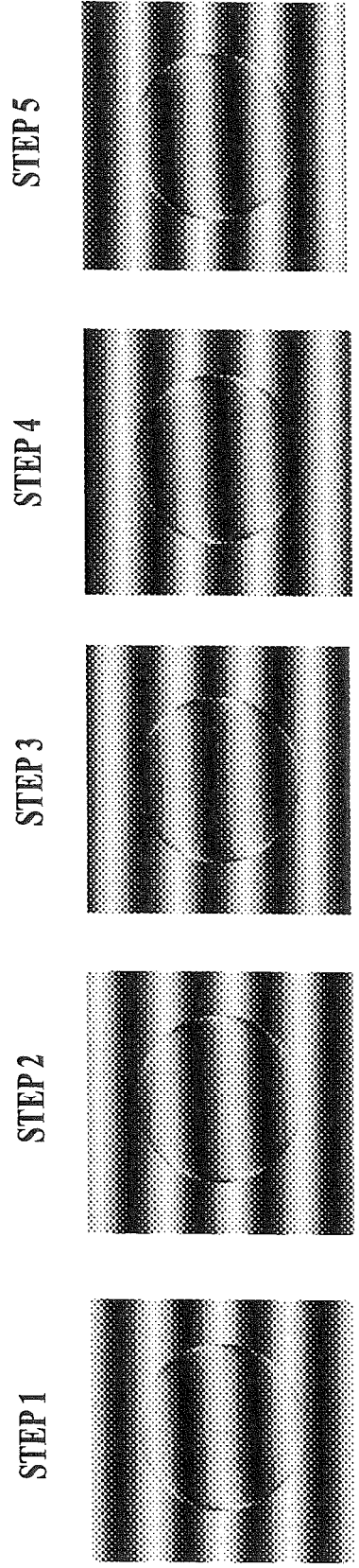
[FIG. 21] This is a diagram showing moire images obtained by performing image capturing in five steps.
Figure 22:
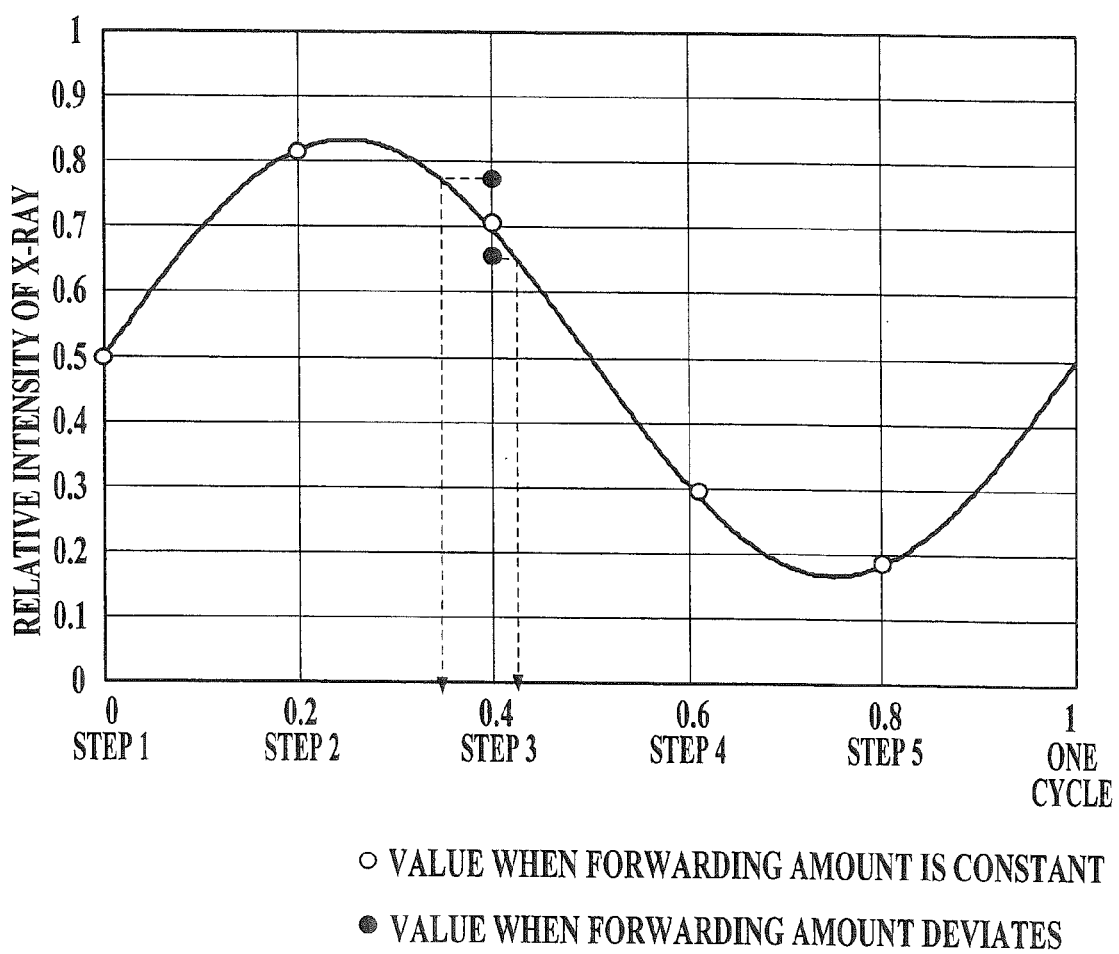
[FIG. 22] This is a graph showing relative intensity of X-ray in focus pixels in moire images of respective steps.

Next, moire images are analyzed (step S205) and are determined whether they can be used to form a reconstruction image (step S206). When the multi-slit 12 is moved at a constant forwarding amount by an ideal forwarding accuracy, five moire images for one slit cycle of the multi-slit 12 can be obtained by performing image capturing at five steps as shown in FIG. 21. Because the moire image of each step is a result of performing fringe scanning at every constant cycle interval which is 0.2 cycle, when focusing on one arbitrary pixel in each moire image, X-ray intensity obtained by normalizing the signal values form a sine-curve as shown in FIG. 22. Therefore, the controller 5 obtains relative intensity of X-ray by focusing on an arbitrary pixel in the obtained moire image of each step. If the relative intensity of X-ray obtained by each of moire images form a sine-curve as shown in FIG. 22, this means that moire images at constant cycle intervals are obtained. Therefore, it is determined that they can be used to form a reconstruction image.

Here, the above sine-curve shape depends on opening width of the multi-slit 12, cycles in the first grating 14 and the second grating 15 and distance between the first grating and the second grating. Further, although the shape will be triangle wave shape in the case of coherent light such as radiation light, the shape is to be in sine-curve shape because X-ray operates as semi-coherent light due to the multi-slit effect.

When there is a moire image which cannot form a sine-curve among the moire images of respective steps, it is determined such moire image cannot be used to form a reconstruction image (step S206; NO) and control information to instruct re-capturing of image by changing the image capturing timing is sent to the X-ray image capturing apparatus 1 from the controller 5 (step S207). For example, as shown in FIG. 22, when a moire image is obtained at 0.35 cycle due to deviation while the third step is set at 0.4 cycle originally, it can be considered that the cause is degradation in forwarding accuracy in the drive unit 122 (for example, noise being superimposed on drive pulse of the pulse motor or such like). Therefore, re-capturing of image is to be instructed to perform image capturing of the third step by setting the timing for image capturing earlier by 0.05 cycle. Alternatively, re-capturing if image can be performed for all five steps wherein only the image capturing timing for the third step may be instructed to be earlier by 0.05 cycles. When all of the moire images of five steps are deviated from the sine-curve by a predetermined amount, it can be instructed so as to increase or decrease the number of drive pulses between activation and termination of the drive unit 122.

In the X-ray image capturing apparatus 1, image capturing timing is adjusted in accordance with the control information and re-capturing of image with a subject being placed is executed.

On the other hand, when it is determined that the moire images can be used to form a reconstruction image (step S206; YES), a reconstruction image with subject is formed by using the plurality or moire images with subject (step S208). For example, change in intensity (change in signal value) is calculated every step for individual pixels in each of the plurality of moire images and differential phase is calculated by the change in intensity. If needed, phase connection (phase unwrap) is carried out and phase of the entire steps is obtained. Optical path difference in z direction is calculated from the phase and a reconstruction image expressing shape of the subject is formed (see the above reference documents (1) and (2)).

Here, analysis of moire images can be performed by using the images not yet been subjected to trend correction.

In the reconstruction image without subject forming processing in step S22 of FIG. 18, processing which is same as the processing performed on the plurality of moire images with subject in the above described reconstruction image with subject forming processing is performed on the moire images without subject and a reconstruction image without subject is formed.

The processing of step S23 of FIG. 18 includes processing for removing image non-uniformity (artifact) from the reconstruction image with subject by using the reconstruction image without subject, image non-uniformity including non-uniformity in X-ray dose distribution caused by change in slit directions of the multi-slit 12 and the grating assembly 200 at the time of image forming, non-uniformity in radiation distribution caused by manufacture variation in the slits and non-uniformity caused by unexpected appearance of the subject holder 130, mainly, in the image.

For example, when the reconstruction image with subject is a differential phase image, a subject reconstruction image for diagnosis is formed by the processing described in the following known document (A) and the known document (B). (Known document (A); Timm Weitkamp, Ana Diazand, Christian David, franz Pfeiffer and Marco Stampanoni, Peter Cloetens and Eric Ziegler, X-ray Phase Imaging with a grating interferometer, OPTICSEXPRESS, Vol. 13, NO. 16, 6296-6004 (2005), Known document (B); Atsushi Momose, Wataru Yoshihiro, Yoshihiro Takeda, Yoshio Suzuki and Tadashi Hattori, Phase Tomography by X-ray Talbot Interferometer for Biological Imaging, Japanese Journal of Applied Physics, Vol. 45, No. 6A, 2006, pp. 5254-5262 (2006)).

When the reconstruction image with subject is an absorption image or a small angle scattering image, as described in the known document (C), signal value of each pixel in the reconstruction image with subject is divided by signal value of its corresponding pixel in the reconstruction image without subject and the result of the above division calculation is obtained as the subject reconstruction image for diagnosis (Known document (C); F. Pfeiffer, M. Beck, O. Bunk, P. Kraft, E. F. Eikenberry, CH. Broennimann, C. Grunzweig, and C. David, Hard-X-ray dark-field imaging using a grating interferometer, nature materials Vol. 7, 134-137 (2008)).

The methods described in the above known documents (A), (B) and (C) also includes processing for correcting image non-uniformity by signal value of each pixel in the reconstruction image with subject obtained in the process of forming the subject reconstruction image for diagnosis being subtracted by signal value of corresponding pixel in the reconstruction image without subject or by dividing the signal value of each pixel in the reconstruction image with subject by the signal value of corresponding pixel in the reconstruction image without subject.

The above processing is preferable because even when there is also variations in characteristics of individual pixels in the X-ray detector 16 used in image capturing and not only in X-ray exposure dose distribution caused by change in slit directions of the multi-slit 12 and each grating in the grating assembly 200 and in characteristics of the subject platform, such influence can be removed. Therefore, even when slit direction can vary according to subject, arrangement direction of the X-ray detector 16 with respect to a subject can be fixed (the position is not changed) and the display direction of a subject in the subject reconstruction image which is to be displayed in the controller 5 is to be always in the same direction in the controller display screen. Thus, there is no need to operate so as to align the direction of the subject reconstruction image in the controller 5 when comparison reading is to be carried out comparing the image with past images in the process of follow-up or the like, and this is even more preferred.

[Second Embodiment]

Next, the second embodiment of the present invention will be described.

In the second embodiment, programs for executing the after-mentioned image capturing control processing B are stored in the storage unit 185 of the main body 18. Further, programs for executing the after-mentioned diagnosis image forming processing B, rotation angles of the multi-slit 12 and the grating assembly 200 from their home positions and gain correction data corresponding to combinations of X-ray detector 16 used for image capturing are stored in the storage unit 55 of the controller 5 in advance. As for other structures of the second embodiment, they are similar to those described in the first embodiment using FIGS. 1 to 12. Operation of the second embodiment will be described hereinafter.

Figure 23:
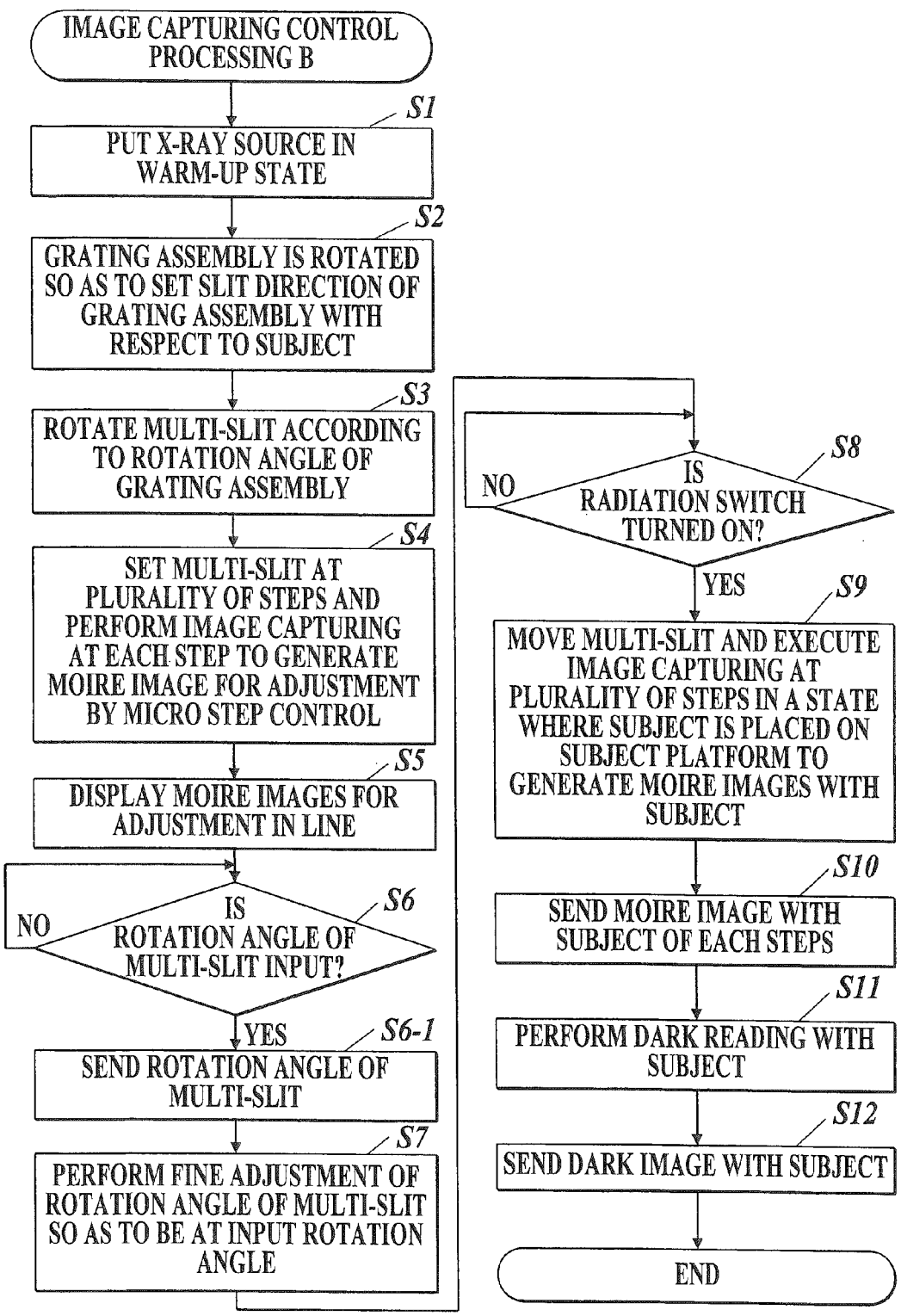
[FIG. 23] This is a flowchart showing image capturing control processing B executed by the control unit of the X-ray image capturing apparatus.

FIG. 23 is a flowchart showing the image capturing control processing B which is to be executed by the control unit 18 of the X-ray image capturing apparatus 1 in the second embodiment. As shown in FIG. 23, the second embodiment is different from the first embodiment in aspects that step S6-1 is executed after step S6 in the flow shown in FIG. 14A and that the processing of steps S13 to S17 shown in FIG. 14B, that is, the processing of image capturing without subject is not carried out. That is to say, in the second embodiment, rotation angle information of the multi-slit 12 is sent to the controller 5 by the communication unit 184 after the rotation angle of the multi-slit 12 is set and a subject is placed on the subject platform 13 to perform image capturing.

Here, the configuration may be such that the rotation angle information of the multi-slit 12 is input by an operator of the controller 5 via the operation unit 52 and not by being sent from the X-ray image capturing apparatus 1. Specifically, as shown in FIG. 17, when the controller 5 is commonly used with other modalities, it is preferred that the configuration is such that the rotation angle of the multi-slit 12 is input by the operation unit 52 of the controller 5 after moire image stored in the X-ray detector 16 is sent by an operator pressing the send button of the X-ray detector 16.

When the rotation angle of the multi-slit 12 and the moire image from the X-ray image capturing apparatus 1 are received by the communication unit 54 in the controller 5, the diagnosis image forming processing B is executed.

Figure 24:
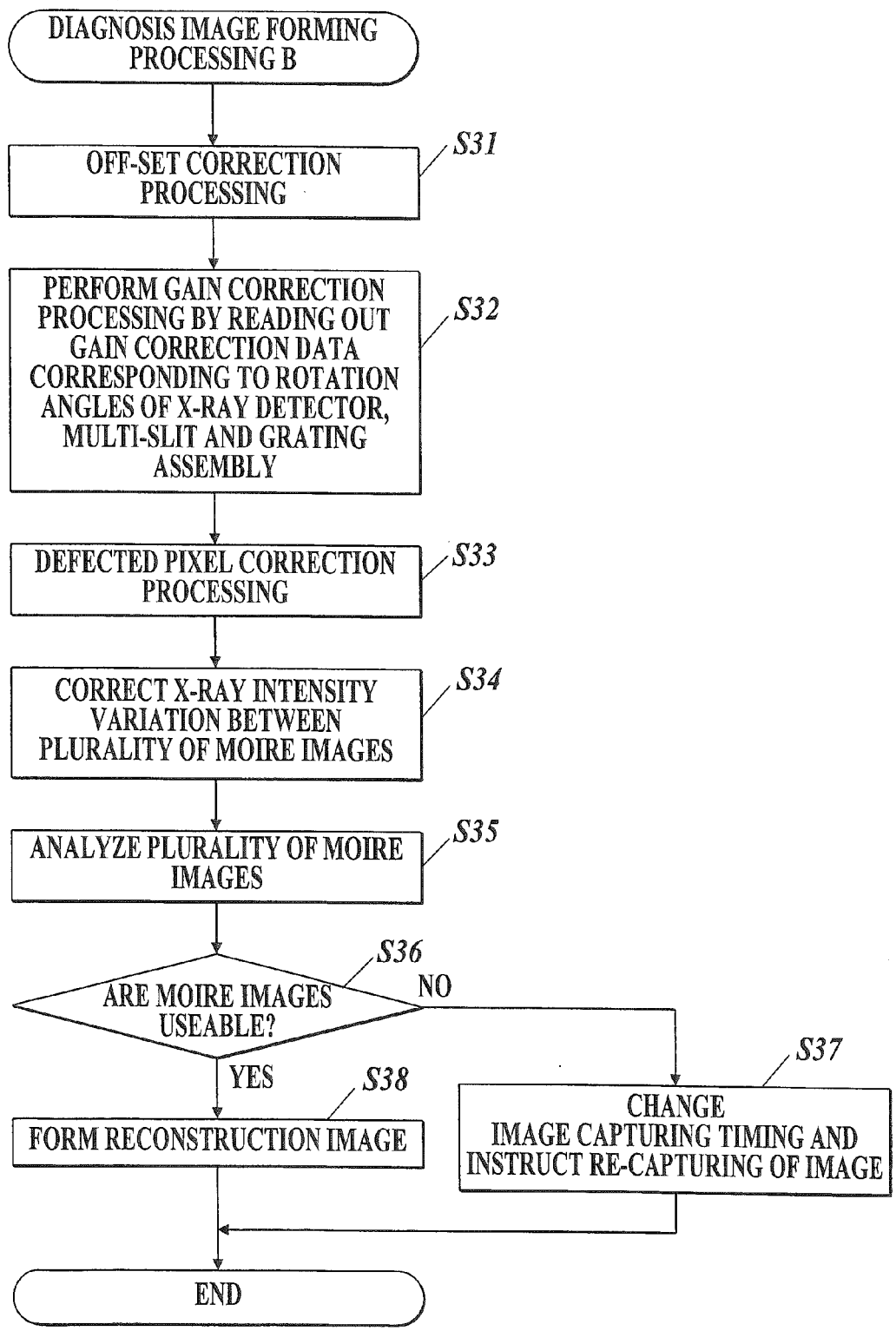
[FIG. 24] This is a flowchart showing diagnosis image forming processing B executed by the control unit of the controller.

FIG. 24 is a flowchart showing the reconstruction image forming processing B which is executed by the control unit 51 of the controller 5 in the second embodiment. This processing is executed by the control unit 51 and the programs stored in the storage unit 55 cooperating with each other.

First, correction processing for correcting variations among individual pixels in the X-ray detector 16 is executed for the plurality of moire images which are received from the X-ray image capturing apparatus 1. Specifically, off-set correction processing (step S31), gain correction processing (step S32) and defected pixel correction processing (step S33) are executed.

In the off-set correction processing of step S31 and the defected pixel correction processing of step S33, processing similar to steps S201 and S202 of FIG. 19 are executed, respectively. In the gain correction processing of step S32, rotation angles of the multi-slit 12 and the grating assembly 200 from their home positions and gain correction data corresponding to the combination of X-ray detector 16 used for the image capturing are read out from the storage unit 55$m$ and gain correction is performed on each moire image on the basis of the read gain correction data. The gain correction data is an image read by the X-ray detector 16 by uniformly emitting X-rays in an amount specified in advance without subject.

Next, X-ray intensity variation correction (trend correction) is performed between the plurality of moire images (step S34). The trend correction is similar to step S204 of FIG. 19, therefore, the description is omitted.

Thereafter, the moire images are analyzed (step S35) and are determined whether they can be used to form a reconstruction image (step S36). The analyzing of step S35 and determining of step S36 are similar to step S205 and step S206 of FIG. 19, respectively, therefore, the descriptions are omitted. Here, analyzing of moire images may be performed by using images not yet been subjected to trend correction.

When there is a moire image which cannot form a sine-curve among the moire images of respective steps, it is determined that the moire image cannot be used for forming a reconstruction image (step S36; NO), and control information instructing to perform re-capturing of image by changing the image capturing timing is sent to the X-ray image capturing apparatus 1 from the controller 5 (step S37). In the X-ray image capturing apparatus 1, image capturing timing is adjusted according to the control information and re-capturing of image is executed with a subject being placed.

On the other hand, when it is determined that the moire images can be used to form a reconstruction image (step S36; YES), a reconstruction image for diagnosis is formed by using the received plurality of moire images (step S37). For example, change in intensity (change in signal value) is calculated every step for individual pixels in the plurality of moire images and differential phase is calculated from the change in intensity. If needed, phase connection (phase unwrap) is carried out and phase of the entire steps is obtained. Optical path difference in z direction is calculated from the phase and a reconstruction image expressing shape of the subject is formed (see the above reference documents (1) and (2)).

In the second embodiment, gain correction data is prepared for each combination of X-ray detector 16 and rotation angle of multi-slit 12 in advance, and image non-uniformity caused by unevenness of X-ray irradiation distribution that occurs with changing in rotation angles of multi-slit 12 and grating assembly 200 can be removed by performing gain correction by reading out the gain correction data according to the combination X-ray detector 16 and rotation angle of multi-slit 12 used in the image forming.

In the processing of the second embodiment, due to the effect of variations in characteristics of individual pixels of the X-ray detector 16, gain correction data needs to be formed for each rotation angle of multi-slit 12 with respect to all of the X-ray detectors 16 which may be used in the X-ray image capturing apparatus 1. Further, because an appropriate correction cannot be carried out unless the arrangement direction of the X-ray detector 16 matches the arrangement direction when the gain correction data was formed, it is preferred that the configuration is such that the direction of the X-ray detector 16 rotates integrally with the multi-slit 12.

[Third Embodiment]

Hereinafter, the third embodiment will be described with reference to drawings.

Figure 25:
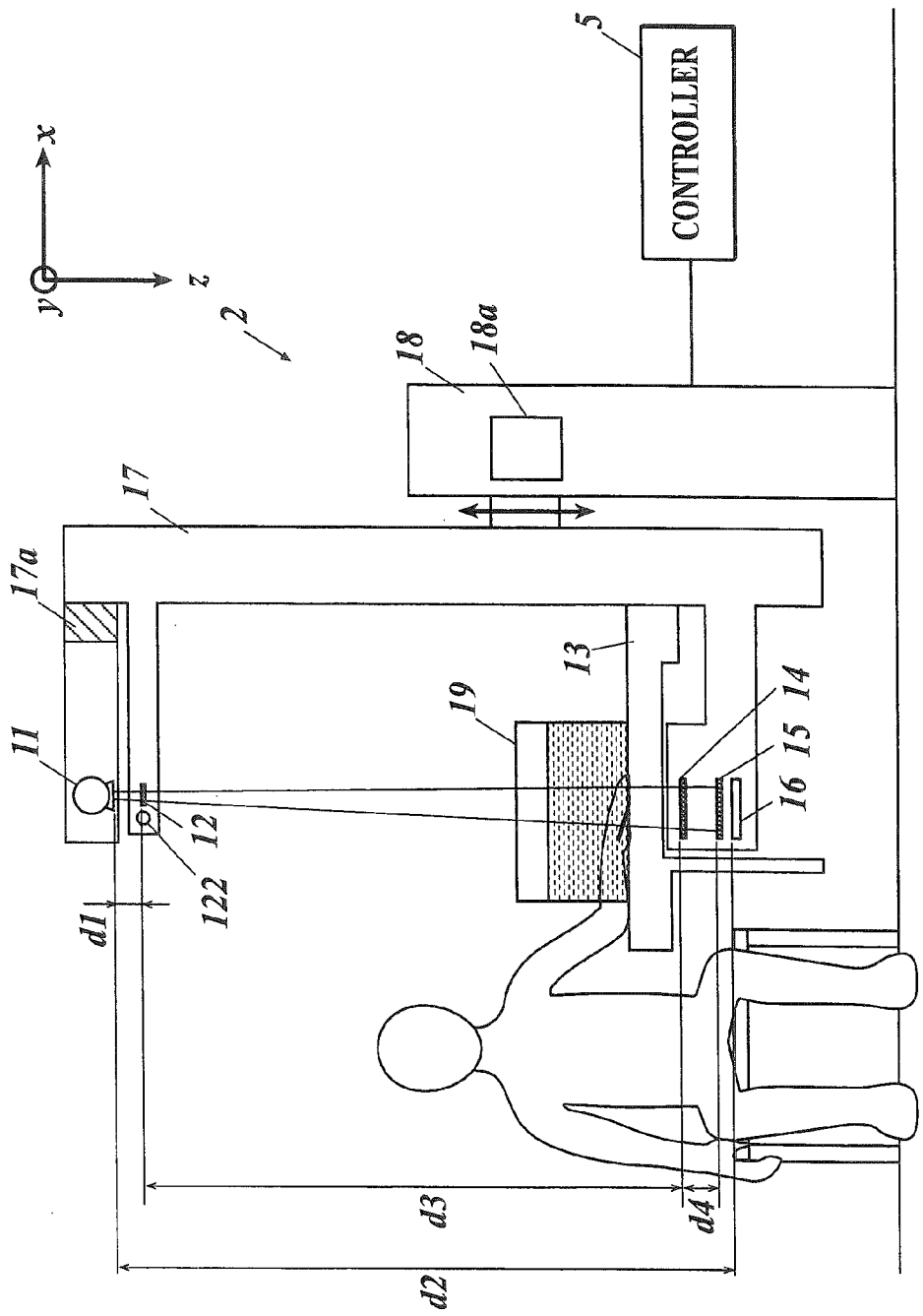
[FIG. 25] This is a diagram showing a X-ray image capturing system (including a side view of a X-ray image capturing apparatus) according to the third embodiment.

FIG. 25 shows the X-ray image capturing system according to the third embodiment. The X-ray image capturing system includes the X-ray image capturing apparatus 2 and the controller 5. The X-ray image capturing apparatus 2 performs X-ray image capturing by Talbot-Lau interferometer, and the controller 5 forms a reconstruction image of a subject by using moire images which are obtained by the X-ray image capturing. Here, the X-ray image capturing apparatus 2 will be described as an apparatus for capturing an image of a hand and fingers as subject, however, the X-ray image capturing apparatus 2 is not limited to such apparatus.

As shown in FIG. 25, the X-ray image capturing apparatus 2 includes the X-ray source 11, the multi-slit 12, the drive unit 122, the subject platform 13, the first grating 14, the second grating 15, the X-ray detector 16, the holding unit 17, the main body 18, the refractive index adjustment tank 19 and the like. That is, this is a configuration in which the refractive index adjustment tank 19 is added to the configuration of X-ray image capturing apparatus 1 described by using FIG. 1 in the first embodiment.

The refractive index adjustment tank 19 is a container placed on the subject platform 13 and water, for example, is filled inside thereof as a liquid substance to reduce X-ray refractive index difference between subject surface and surrounding thereof.

Figure 32:
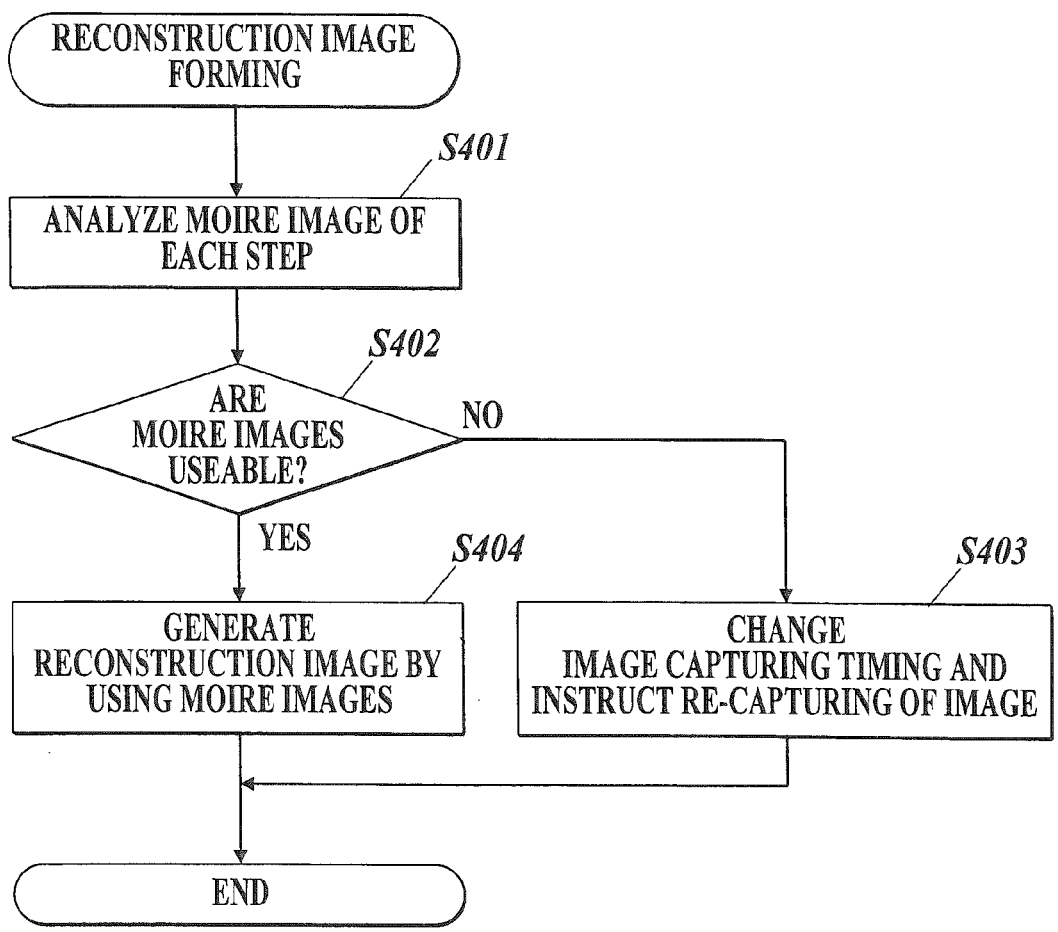
[FIG. 32] This is a flowchart showing a reconstruction image forming processing executed by the control unit of the controller in step S43 of FIG. 28.

Moreover, in the third embodiment, programs for executing the after-mentioned image capturing control processing C are stored in the storage unit 185 of the main body 18. Further, programs for executing the after-mentioned reconstruction image forming processing shown in FIG. 32 are stored in the storage unit 55 of the controller 5.

Other configurations such as the X-ray source 11, the multi-slit 12, the drive unit 122, the subject platform 13, the first grating 14, the second grating 15, the X-ray detector 16, the holding unit 17 and the main body 18 are same as those described in the first embodiment, and therefore, the descriptions in the first embodiment are to be applied. Here, in the embodiment, it does not matter if the multi-slit rotation unit 121 and the grating assembly rotation unit 210 are included or not. Further, it does not matter if the first grating 14 and the second grating 15 constitute the grating assembly or not.

When coherence X-rays are emitted onto a subject in Talbot interferometer and Talbot-Lau interferometer, wave front is distorted due to the subject. This is because transmission speed of X-rays differ due to refractive index of X-rays being different between the subject and the surrounding thereof. Therefore, greater the difference in X-ray refractive index between the subject and the surrounding thereof is, greater the distortion of wave front. In Talbot interferometer and Talbot-Lau interferometer, greater the distortion of wave front is, greater the value of differential phase. That is, in a reconstruction image of subject, the parts in the subject having great difference in X-ray refractive index comparing to that of the surrounding thereof are expressed by great signal values.

Therefore, in a case where image capturing is performed by setting a structure (for example, cartilage or the like) in a subject as the region of interest, when there are form variation (for example, wrinkles in skin at a joint and the like) in the subject surface, signal values indicating such form variation in the subject surface become large because the difference in X-ray refractive index between the subject surface and the air therearound is relatively large. Therefore, such signal values are superimposed on minute differences in signal values indicating the structure of the region of interest causing visibility of the signal values of the region of interest be degraded.

Figure 26A:
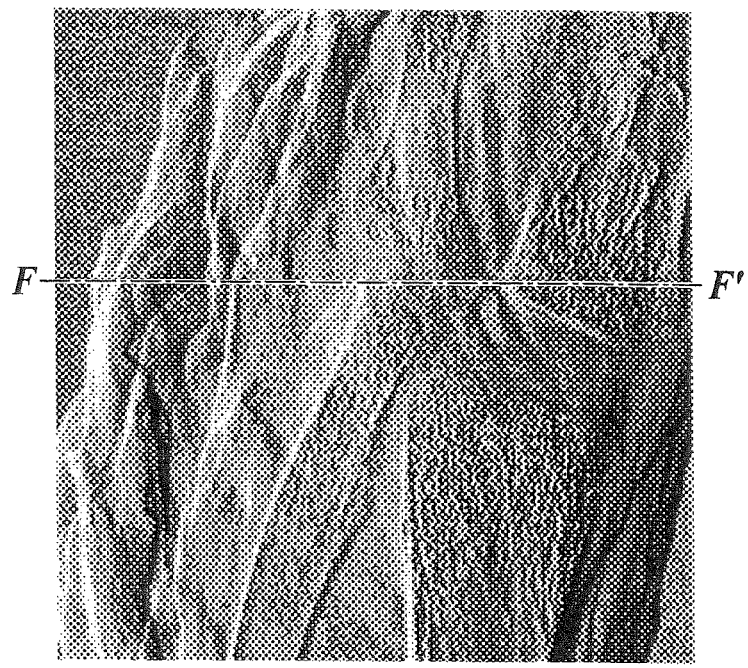
[FIG. 26A] This is a diagram showing a reconstruction image (differential phase image) obtained by performing image capturing of a chicken wing as a subject in the air by using Talbol Lau interferometer.

FIG. 26A shows a reconstruction image (differential phase image) obtained by capturing an image of a chicken wing as subject in the air by using Talbot-Lau interferometer.

Figure 26B:
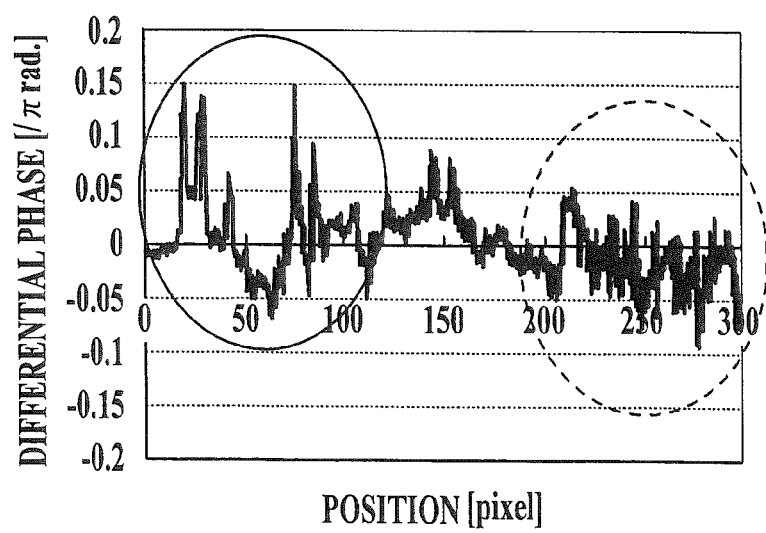
[FIG. 26B] This is a diagram showing a profile of signal values at positions along F-F' of FIG. 26A.

FIG. 26B shows profile of signal values at position along F-F' in FIG. 26A.

The area encircled by solid line in FIG. 26B corresponds to the skin portion (including wrinkles) in the subject surface and the area encircled by dashed line corresponds to the region of interest (surrounding portion of soft tissue) inside the subject.

As shown in FIG. 26B, because difference in refractive index between the skin portion of the subject surface and the surrounding thereof (air) is large, form of the skin portion is shown as large signal values. On the other hand, because difference in refractive index between the region of interest (surrounding portion of soft tissue) inside the subject and the surrounding thereof is small, signal values indicating the region of interest (surrounding portion of soft tissue) are small.

If the skin portion (including wrinkles) in the subject surface and the region of interest (surrounding portion of soft tissue) inside the subject are not superimposed in z direction, the region of interest (surrounding portion of soft tissue) can be visible even in the image captured in the air.

However, it is difficult to know the relative positional relation of the region of interest inside the subject with respect to the subject surface structure before image capturing.

Figure 27:
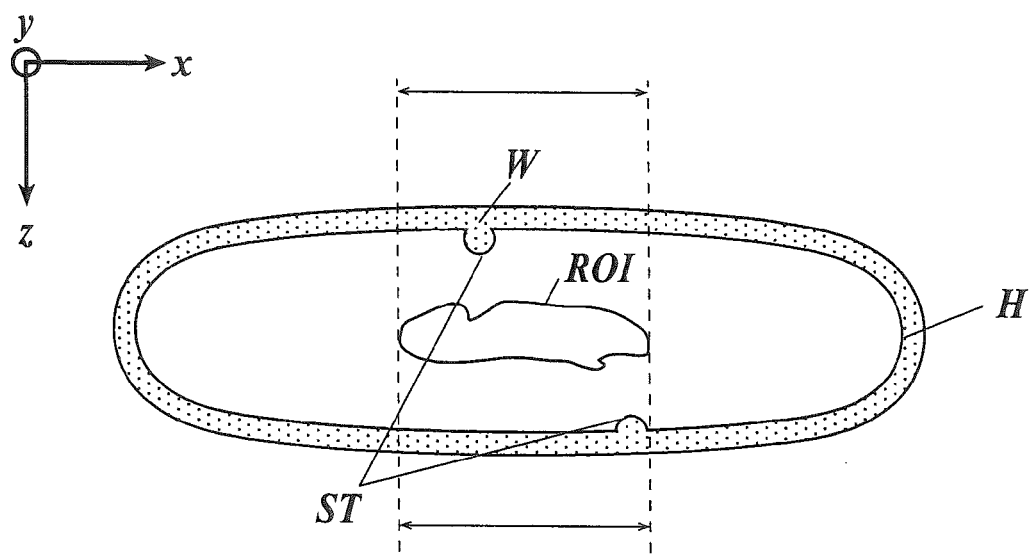
[FIG. 27] This is a diagram showing a relation between form variation in subject surface and a region of interest.

In particular, as shown in FIG. 27, when there are form varied portions (shown by ST in FIG. 27) in the subject surface in X-ray emission direction (the surface of X-ray entering side and the surface of X-ray exiting side) corresponding to the region of interest inside the subject H (shown by ROI in FIG. 27), that is, when there are form varied portions in the subject surface within the range shown by arrows in FIG. 27, signal values indicating the region of interest (ROI) and larger signal values indicating the form varied portions (ST) are superimposed on each other when the reconstruction image is observed and the signal values indicating the region of interest (ROI) cannot be recognized visually.

In view of the above, in the embodiment, by a liquid substance (shown by W in FIG. 27) having high adhesiveness to the subject surface and its X-ray refractive index being approximately same as that of the subject surface covering the subject surface as shown in FIG. 27, a reconstruction image in which the signal values indicating the form varied portions in the subject surface are reduced can be obtained by performing image capturing after reducing the difference in X-ray refractive index between the subject surface and the surrounding thereof to be smaller than the difference in X-ray refractive index between the region of interest and the surrounding thereof. In particular, covering of the region that superimpose on the region of interest in the reconstruction image, that is, the subject surface in X-ray emission direction (upper direction and lower direction) corresponding to the region of interest as shown by the arrows in FIG. 27 with the above mentioned liquid substance and reduction of the difference in X-ray refractive index between the subject surface and the surrounding thereof within the covered range so as to be smaller than the difference in X-ray refractive index between the region of interest and the surrounding thereof are important for improving visibility of the region of interest in the reconstruction image.

Figure 28:
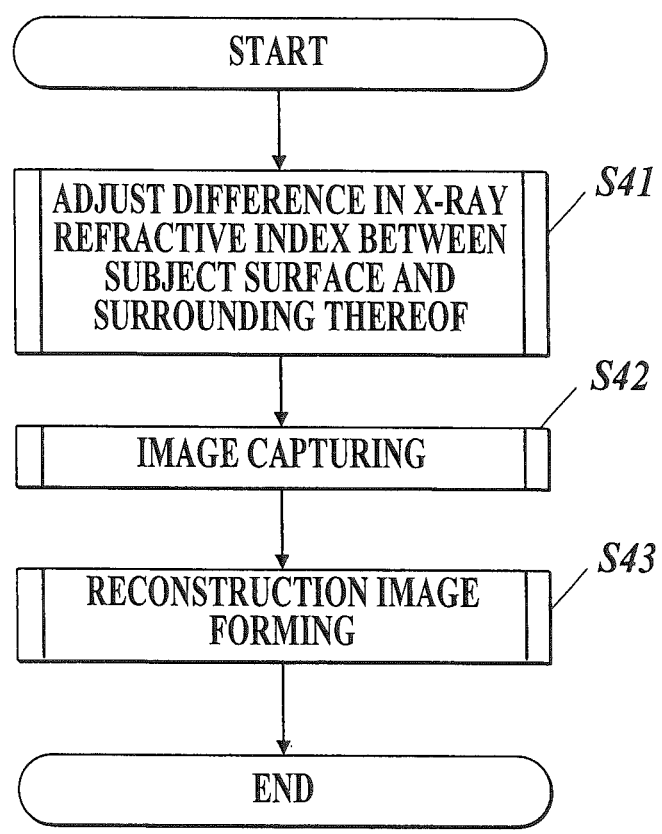
[FIG. 28] This is a flowchart showing image capturing procedure in embodiments of the present invention.

That is, as for the procedure of image capturing in the embodiment, as shown in FIG. 28, adjustment to reduce the difference in X-ray refractive index between the subject surface and the surrounding thereof so as to be smaller than the difference in X-ray refractive index between the region of interest and the surrounding thereof is performed by covering the subject surface with a liquid substance having great adhesiveness to the subject surface and its X-ray refraction index being approximately same as that of the subject surface, first, (step S41). Next, image capturing is performed by emitting X-rays from the X-ray source 11 (step S42) and a reconstruction image is generated (step S43).

In step S41, here, the subject (a hand in this case) is put in the refractive index adjustment tank 19 which is filled with water as shown in FIG. 25. Water has X-ray refractive index that is close to that of the subject surface. Further, when a hand is put into water, the subject surface is covered with water and the water adheres to the subject surface by water pressure. Therefore, the difference in X-ray refractive index between the subject surface and the surrounding thereof is reduced.

Here, water is most preferred as a liquid substance that covers the subject considering its convenience, low cost and safetyness. However, fragrance, disinfectant, color dye and the like can be added to the water so as to improve comfort of a patient. Further, it is preferable to used a liquid substance that is closer to human flesh and body fluid and not water. For example, hyaluronic acid solution, gelatin solution, glycerin solution, mannose solution, water used to wash rice, starch water and the like can be used individually or by being mixed with water.

Figure 29A:
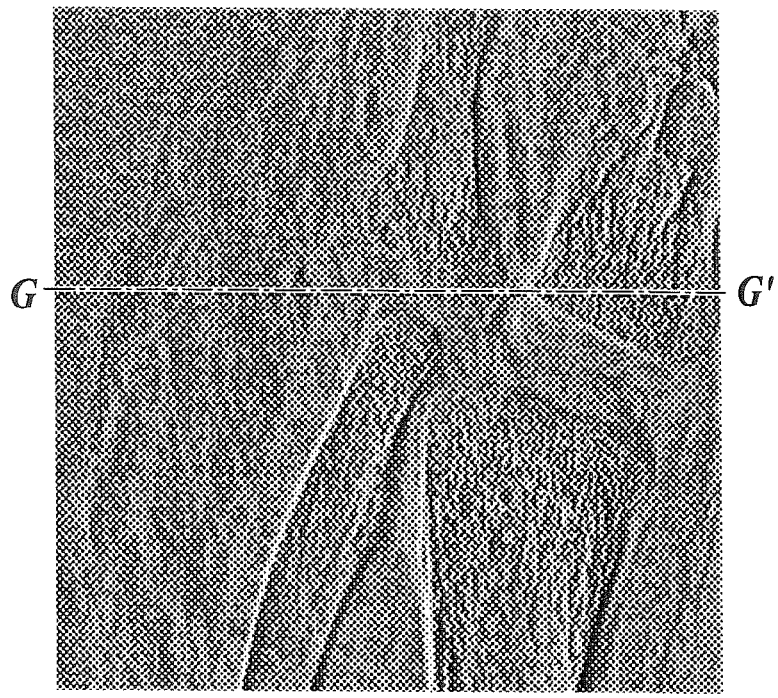
[FIG. 29A] This is a diagram showing a reconstruction image (differential phase image) obtained by performing image capturing of the chicken wing wherein the chicken wing is put in water by using Talbot Lau interferometer.
Figure 29B:
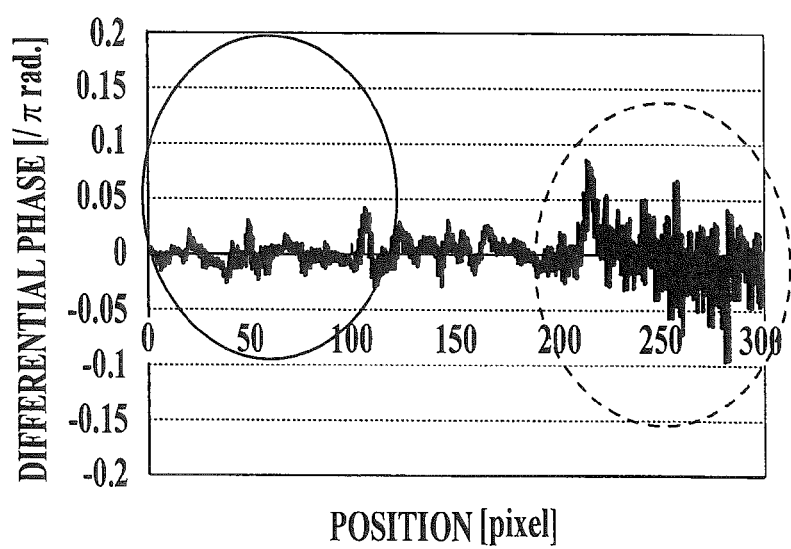
[FIG. 29B] This is a diagram showing a signal profile at positions along G-G' of FIG. 29A.

FIG. 29A shows a reconstruction image (differential phase image) obtained by putting a chicken wing in water and performing image capturing by used Talbot-Lau interferometer, the subject being arranged similarly as in FIG. 29A. FIG. 29B shows signal profile at position along G-G' in FIG. 29A. The part encircled with solid line in FIG. 29B has signal values of pixels corresponding to skin portion of subject surface. The part encircled with dashed line in FIG. 29B has signal values of pixels corresponding to the region of interest (surrounding portion of soft tissue) inside the subject.

As shown in FIG. 29B. by performing image capturing in water which has X-ray refractive index close to that of the subject, signal values indicating form variation in the subject surface can be small comparing to the case when image capturing is performed in the air (see FIG. 26B). Therefore, a reconstruction image in which the structure inside the subject can be easily observed wherein influence of the subject surface being reduced even in the region of interest (surrounding portion of soft tissue) can be obtained.

Figure 30A:
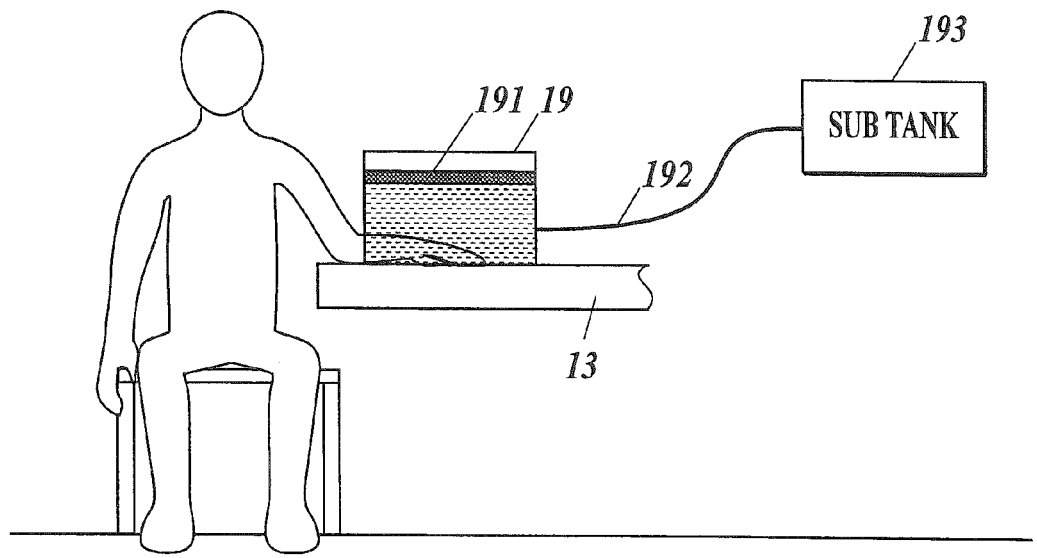
[FIG. 30A] This is a diagram for explaining a refractive index adjustment tank provided with a floating lid as a subject fixation device.
Figure 30B:
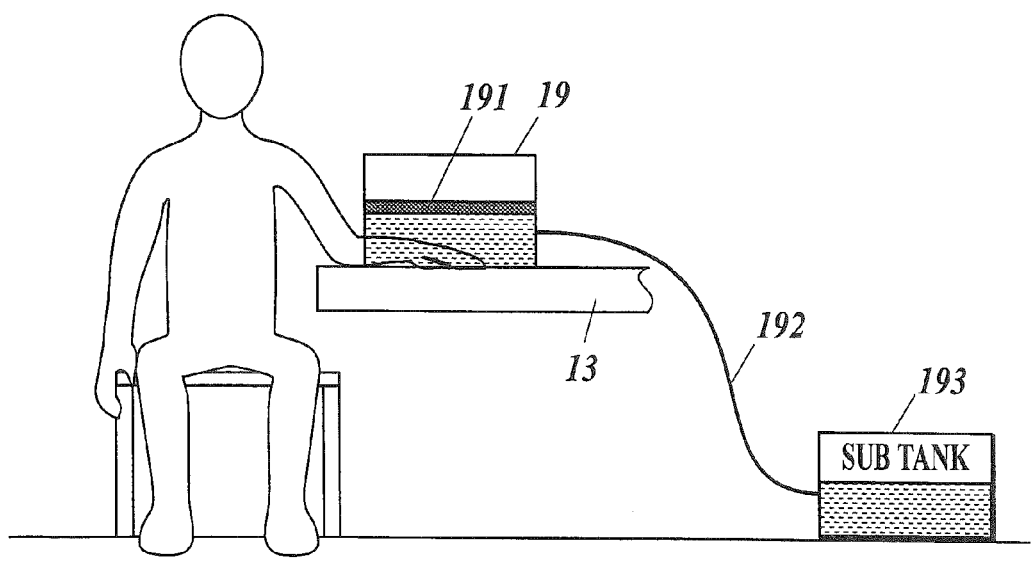
[FIG. 30B] This is a diagram for explaining how a subject is fixated in the refractive index adjustment tank provided with a floating lid as a subject fixation device.

Here, when image capturing is performed by using Talbot interferometer or Talbot-Lau interferometer, it is expected that the image capturing time becomes longer (in terms of few minutes) comparing to the conventional simple X-ray image capturing system because a plurality of moire images are to be captured. There is a possibility that the subject moves during this time. Therefore, it is preferred that the X-ray image capturing apparatus 2 is configured so as to hold and fixate the subject. For example, it is preferred that the refractive index adjustment tank 19 is configured by including a floating lid 191 and so as to be connected to a sub tank 193 via a pipe 192 as shown in FIG. 30A. During image capturing, first, the refractive index adjustment tank 19 is filled with water and a subject is placed in the water in a state where the sub tank 193 is held at a position higher than the refractive adjustment tank 19. Next, the sub tank 193 is moved to a position lower than the refractive index adjustment tank 19 as shown in FIG. 30B and the water level is lowered to the position where the floating lid 192 oppresses the subject. In such way, the subject can be prevented from moving in z direction, especially in X-ray tube direction, during image capturing by oppressing the subject by the floating lid 192 so as to hold the subject, and diagnosis accuracy of reconstruction image can be improved. Here, in order to further stabilize the subject, it is preferred that the subject platform 13 has a length that can support from elbow to finger tips. This enables the patient to put the load (weight) of surrounding portions of the imaging target section on the subject platform and therefore, possibility of unexpectedly moving his/her fingers, which are the region of interest, can be greatly reduced.

Figure 31:
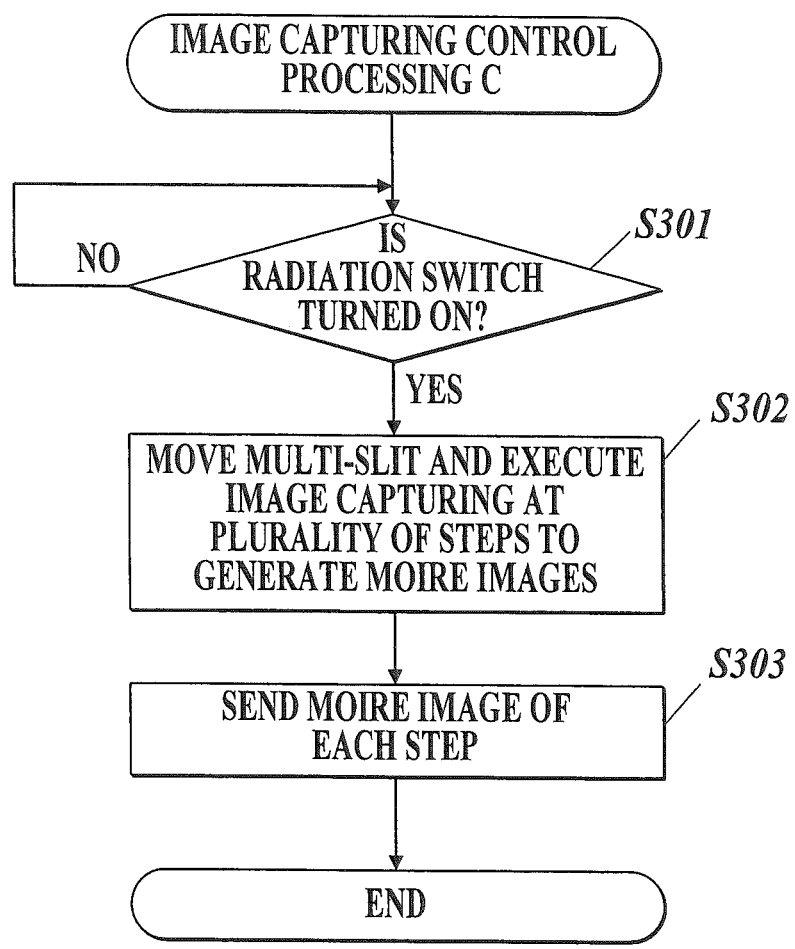
[FIG. 31] This is a flowchart showing image capturing control processing C executed by the control unit of the main body in step S42 of FIG. 28.

In step S42, the image capturing control processing C is executed by the flow shown in FIG. 31 by the control of the control unit 181 of the X-ray image capturing apparatus 2.

Here, the above described X-ray image capturing method by Talbot-Lau interferometer is used for X-ray image capturing and fringe scanning is used for reconstruction of subject image. In the X-ray image capturing apparatus 2, the multi-slit 12 is moved in step wise manner in equal intervals for a plurality of steps and image capturing is performed at each step to obtain a moire image at each step.

The number of steps is 2 to 20 steps, and more preferably, 3 to 10 steps. In view of obtaining a reconstruction image having high visibility in short time, it is preferred that the number of steps is 5.

As shown in FIG. 31, when the radiation switch is operated so as to be turned it ON by an operator (step S301; YES), the multi-slit 12 is moved in x direction by the drive unit 122, and image capturing is executed at a plurality of steps and moire images are generated (step S302). Specific processing of step S302 is similar to the processing described in step S9 of FIG. 14B, therefore, the described will be applied here.

When image capturing of each step is finished, the moire image of each step is sent to the controller 5 from the main body 18 (step S303). A moire image can be transmitted to the controller 5 from the main body 18 every time the image capturing of each step is completed or the moire images can be transmitted as a group after the image capturing of all of the steps is completed and all of the moire images are obtained.

In step S43, a reconstruction image is formed by the flow shown in FIG. 32 by the controller 5.

As shown in FIG. 32, first, the moire images are analyzed (step S401) and are determined whether they can be used to form a reconstruction image (step S402). The processing of steps S401 and S402 are similar to the processing of steps S205 and S206 shown in FIG. 19, therefore, the descriptions are applied here.

When there is a moire image which cannot form a sine-curve among the moire images of individual steps, it is determined that the moire image cannot be used to form a reconstruction images (step S402; NO), and control information instructing to perform re-capturing of image by changing the image capturing timing is sent to the X-ray image capturing apparatus 2 from the controller 5 (step S403). The processing of step S403 is similar to the processing described in step S207 of FIG. 19, therefore, the description is applied there.

On the other hand, when it is determined that the moire images can be used to form a reconstruction image (step S402; YES), the moire images are processed by the controller 5 and a reconstruction image of a subject is to be formed (step S404). The processing of step S404 is similar to the processing described in step S208 in FIG. 19, therefore, the description is applied here.

[Fourth Embodiment]

Hereinafter, the fourth embodiment of the present invention will be described.

The X-ray image capturing apparatus 2 of the fourth embodiment is different from the X-ray image capturing apparatus 2 of the third embodiment showing in FIG. 25 in an aspect that the refractive index adjustment tank 19 is not included. Other configurations are similar to the X-ray image capturing apparatus 2 described in the third embodiment, therefore, the descriptions are applied here. Hereinafter, image capturing method of the fourth embodiment will be described.

In the fourth embodiment, the X-ray refractive index difference adjusting method in step S41 of FIG. 28 is different from the method in the third embodiment.

Here, a liquid substance having great adhesiveness to a subject surface and its X-ray refractive index being approximately same as that of the subject surface, for example, gel such as gelatin solution, starch water or the like is applied on the subject surface (both front and back) so as to cover the subject surface. In particular, it is important that the region in the reconstruction image that superimposes on the region of interest, that is, the subject surface in X-ray emission direction (upward direction and downward direction) corresponding to the region of interest as indicated by the arrows in FIG. 27 is covered with the gel in order to improve the visibility of the region of interest. In such way, by reducing the difference in X-ray refractive index between the subject surface and the surrounding thereof so as be smaller than the difference in X-ray refractive index between the region of interest and the surrounding thereof, a reconstruction image in which the region of interest has a good visibility wherein signal values indicating form variations in the subject surface are reduced can be obtained. Because it is expected that the number of minutes needed for image capturing is to be long, about 5 minutes, for example, it is preferred that the liquid substance is a material having viscosity.

Instead of applying a liquid substance on subject surface, subject surface may be covered with a refractive index adjustment device in a form of a water cushion made by a liquid substance such as water, gel or the like having a great adhesiveness to subject surface and its X-ray refractive index being approximately same as that of subject surface being filled in a bag made of plastic material (for example, a plastic bag).

Here, in the case of image capturing using Talbot interferometer or Talbot-Lau interferometer, the number of minutes for image capturing is expected to be long, about 5 minutes, for example, because a plurality of moire images are to be captured. There is a possibility that the subject moves during this time. Therefore, it is preferred that the X-ray image capturing apparatus 2 includes a configuration for pressing and fixating a hand and fingers which are the region of interest without causing stress on the subject.

Figure 33:
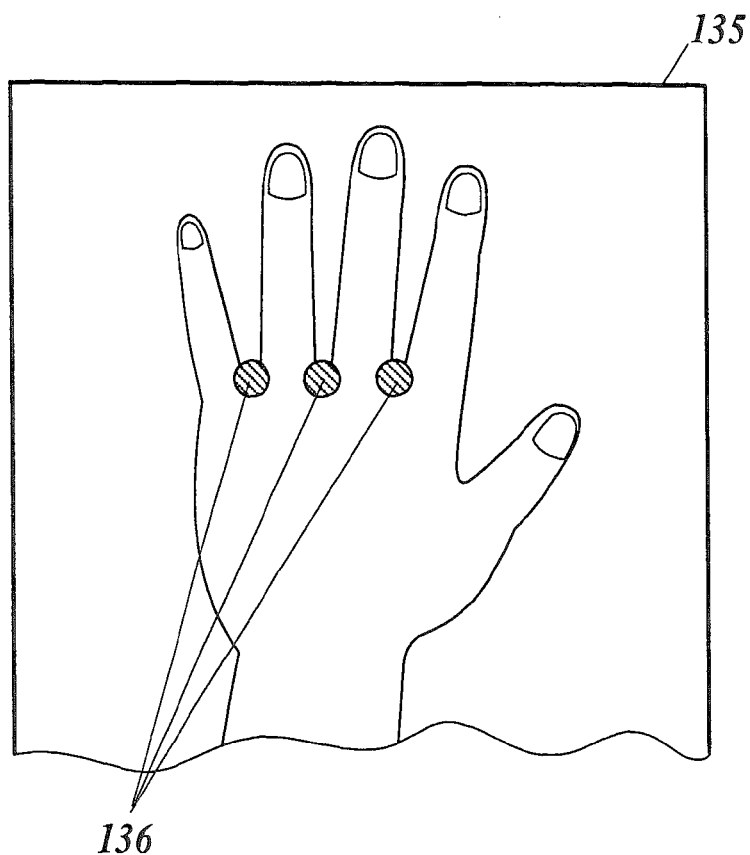
[FIG. 33] This is a diagram showing a holding board provided with finger spacers which fixate a subject.

For example, by providing a holding plate 135 on which finger spacers 136 for fixating the subject on the subject platform 13 as shown in FIG. 33 and performing image capturing by setting a subject thereon, moving of the subject, especially in x-y plan direction, during image capturing can be restricted. Here, because size of a hand and spaces between fingers are different for each subject, it is preferred that the holding plate 135 provided with finger spacers 136 in which convex amount and positions are adjusted are formed for each patient in advance and the holding plate 135 of the patient is to be attached to the subject platform 13 by a magnet or the like during image capturing.

Moreover, the subject holder 130 described by using FIGS. 4A and 4B in the first embodiment can be provided on the subject platform 13. Here, by using the subject holder 130 along with the configuration of covering the subject surface with the above described water cushion object, moving of the subject in upper direction can also be restricted by the weight of the object placed on the subject.

Figure 34:
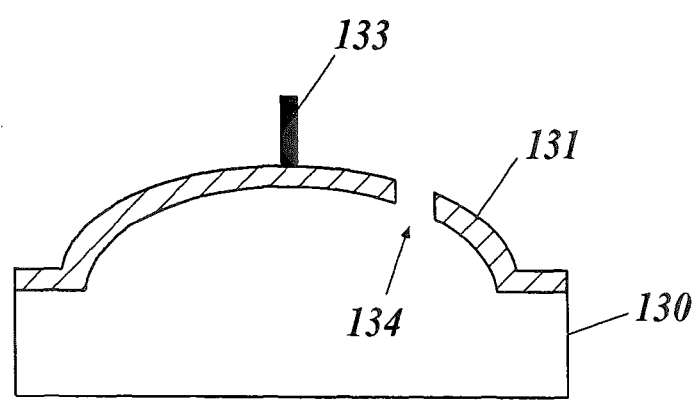
[FIG. 34] This is a side view showing a subject holder having a notch.

In order to prevent unexpected appearance of the subject holder 130 in the reconstruction image, it is preferred that the subject holder 130 has a uniform thickness and even X-ray transmissivity. Further, as shown in FIG. 34, the unexpected appearance of the subject holder 130 in the reconstruction image can be prevented by providing an opening (notch) 134 in the subject holder 130 at the part corresponding to the joint which is the structure (region of interest) to be focused.

It is sufficient that the subject holder 130 endures the weight of the finger tip portions and a small force of a patient pressing the holder from above, and the subject holder 130 can be formed with a resin of low cost and which enables mass production.

[Fifth Embodiment]

Next, the fifth embodiment of the present invention will be described.

In the third embodiment and the fourth embodiment, there is a case where the floating lid 191 or the subject holder 130 as subject fixation device provided to fixate the subject during image capturing has a shape or thickness where X-ray transmissivity is not uniform from place to place. In such case, the floating lid 191 or the subject holder 130 unexpectedly appears in the image due to the non-uniformity of X-ray transmissivity.

In view of the above, in the fifth embodiment, image non-uniformity due to the influence of the floating lid 191 or the subject holder 130 is reduced by forming the subject reconstruction image for diagnosis by using the moire images with subject obtained by the image capturing performed with subject and moire images without subject obtained by image capturing performed without subject.

The x-ray image capturing system of the fifth embodiment may have the configuration described in the third embodiment (see FIG. 25) or may have the configuration described in the fourth embodiment (the configuration not including the refractive index adjustment tank 19).

The procedure of image capturing is similar to that shown in FIG. 28. However, the image capturing of step S42 and the reconstruction image forming processing of step S43 are different, therefore, they will be described hereinafter.

Figure 35:
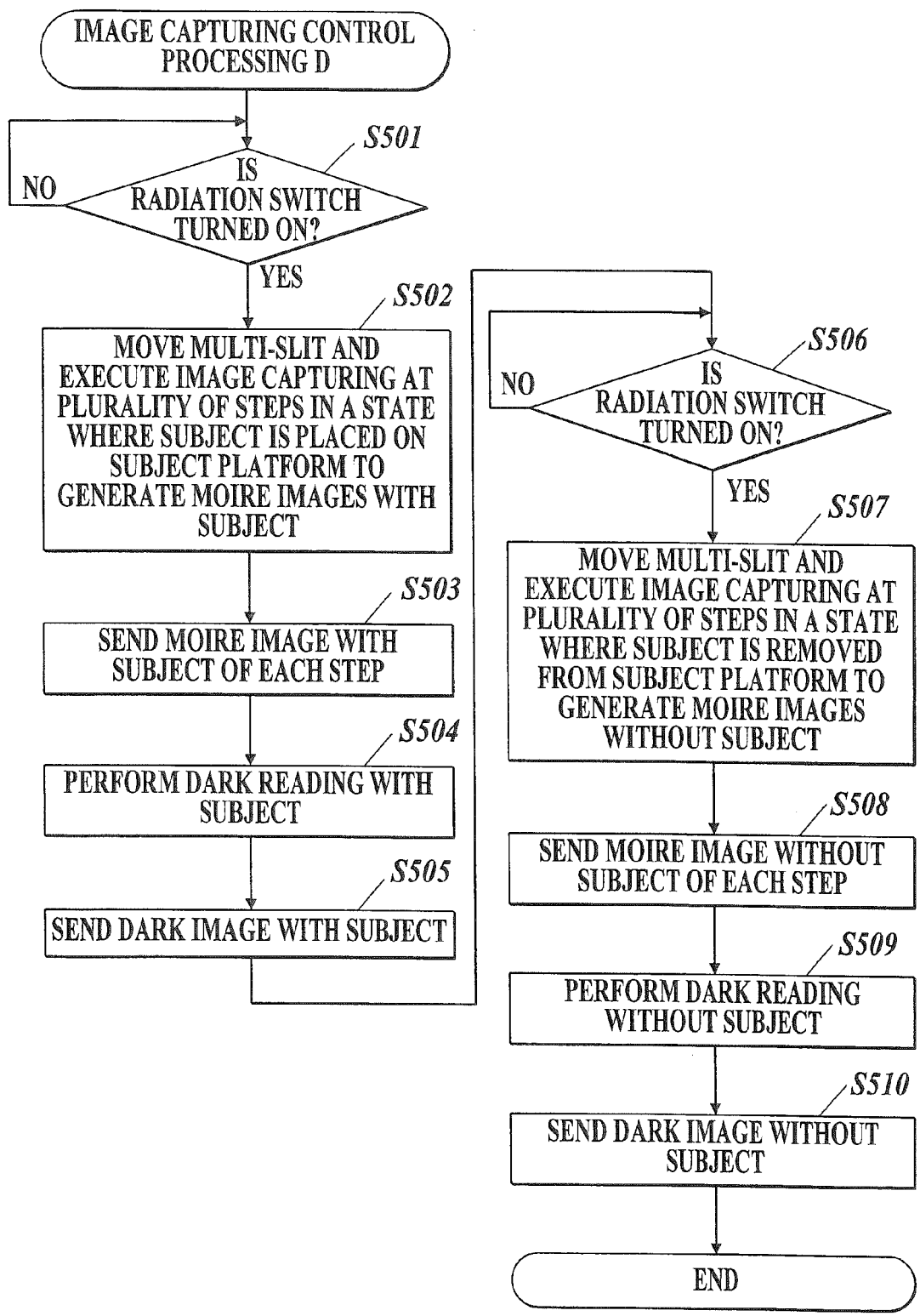
[FIG. 35] This is a flowchart showing image capturing control processing D executed by the control unit of the main body according to the fifth embodiment.

FIG. 35 is a flowchart showing the image capturing control processing D which is executed by the control unit 181 of the X-ray image capturing apparatus 2 in image capturing step of step S42 in FIG. 28. The image capturing control processing D is executed by the control unit 181 and the programs stored in the storage unit 185 cooperating with each other.

When a subject is placed on the subject platform 13 and an operator operated to turn ON the radiation switch (step S501; YES), the multi-slit 12 is moved in its slit aligning direction by the drive unit 122 and a plurality of moire images with subject are generated (step S502).

When image capturing of each step is completed, the moire image of each step is sent to the controller 5 from the communication unit 184 of the main body 18 (step S503). The moire images with subject are sent to the controller 5 from the main body 18 one by one every time the image capturing of each step is completed.

Next, dark reading is performed in the X-ray detector 16 and a dark image for correcting image data with subject is obtained (step S504). Dark reading is performed at least once. Alternatively, dark reading may be performed for a plurality of times and the average value thereof may be obtained as the dark image. The dark image is sent to the controller 5 from the communication unit 184 (step S505). Off-set correction data based on the dark reading is commonly used to correct each moire image signal.

Here, after obtaining of a moire image at a step is completed, dark reading for this step may be performed, and the off-set correction data exclusive for each step may be generated in the obtaining of dark image.

Next, the processing is to be in a waiting state for an operator to operate so as to turn ON the radiation switch (step S506). Here, an operator removes the subject from the subject platform 13 and makes to patent evacuate so that moire images without subject can be formed. When preparation for image capturing without subject is completed, the radiation switch is pressed.

When the radiation switch is pressed (step S506; YES), the multi-slit 12 is moved in its slit aligning direction by the drive unit 122 and image capturing without subject is executed at a plurality of steps and a plurality of moire images without subject are generated (step S507). When image capturing of each step is completed, moire image of each step is sent to the controller 5 from the communication unit 184 of the main body 18 (step S508). The moire images with subject are sent to the controller 5 from the main body 18 one by one every time the image capturing of each step is completed.

Next, dark reading is performed in the X-ray detector 16 and a dark image without subject is obtained (step S509). Dark reading is performed at least once. Alternatively, dark reading may be performed for a plurality of times and the average value thereof may be obtained as the dark image. The dark image is sent to the controller 5 from the communication unit 184 (step S510), and the series of image capturing with respect to one image capturing order is completed.

The processing to be executed by the control unit 51 of the controller 5 in the reconstruction image forming step of step S43 in FIG. 28 is similar to the diagnosis image forming processing A descried by using FIGS. 18 to 20 in the first embodiment, therefore, the description is applied here. In the correction of X-ray intensity variations among the plurality of moire images, a detection device such as a sensor for detection X-ray exposure dose can be provided on the back of the X-ray detector 16, and signal value differences caused by X-ray intensity variations during image capturing among the moire images can be corrected on the basis of the X-ray exposure dose during image capturing of each moire image output from the detection device.

As described above, according to the X-ray image capturing system of the first and the second embodiments, when a plurality of moire images with subject which are captured by placing a subject on the subject platform 13 are input, the control unit 51 of the controller 5 corrects the differences in signal values caused by variations in X-ray intensity during image capturing among the plurality of moire images and forms a reconstruction image with subject on the basis of the plurality of moire images which are corrected. Further, when a plurality of moire images without subject which are captured by not placing the subject in a state where the grating assembly rotation unit 210 and the multi-slit rotation unit 121 are set in the same condition as in the image capturing of the plurality of moire images with subject are input, the control unit 51 corrects the differences in signal values caused by variations in X-ray intensity during image capturing among the plurality of moire images and forms a reconstruction image without subject on the basis of the plurality of moire images which are corrected. Then, the control unit 51 corrects the image non-uniformity in the reconstruction image with subject ascribed to unevenness in X-ray distribution caused by rotation angles of the multi-slit 12 and the grating assembly 200 on the basis of the reconstruction image without subject, and forms a subject reconstruction image for diagnosis.

Therefore, influence of differences in signal values caused by variations in X-ray intensity during image capturing among the plurality of moire images on image quality (minute signal) and influence of image non-uniformity and the like due to unevenness of X-ray dose distribution caused by rotation angles of the multi-slit 12 and the grating assembly 200 can be removed and a reconstruction image good for diagnosis can be provided.

Moreover, by the signal value of each pixel of the reconstruction image with subject being subtracted by the signal value of the corresponding pixel of the reconstruction image without subject from or the signal value of each pixel in the reconstruction image with subject being divided by the signal value of the corresponding pixel in the reconstruction image without subject, influence caused by such case where the subject holder 130 has a shape or thickness in which X-ray transmissivity is not uniform on image quality of the reconstruction image (occurrence of artifacts caused by the subject holder 130) can be removed.

Moreover, by correcting variations in X-ray intensity between each image capturing in a predetermined direction, the X-ray intensity variations in one dimensional direction between each image capturing can be corrected. For example, by performing such correction in the reading line direction in the X-ray detector 16, the X-ray intensity variations or the like in reading line direction of the X-ray detector 16 caused by a time rag between the emission timing of the X-ray source 11 and the read timing of the X-ray detector 16 can be corrected.

Further, by performing the correction of X-ray intensity variations among image capturing in two dimensional directions, the X-ray intensity variations in two dimensional directions between each image capturing can be corrected.

Furthermore, according to the X-ray image capturing apparatus 1 in the first and the second embodiments, the grating assembly 200 in which relative positional relation between the first grating 14 and the second grating 15 is adjusted and fixed in advance so that either of sharpness of interference fringes in moire images and the number of interference fringes in moire images fulfills the present standard, the grating assembly rotation unit 210 for adjusting slit direction of the grating assembly 200 with respect to a subject and the multi-slit rotation unit 121 for rotating the multi-slit 12 are included, and when the grating assembly 200 is rotated according to the arrangement of a subject, by the control unit 181, the multi-slit 12 is rotated abound the X-ray emission axis by the multi-slit rotation unit 121 according to the rotation of the grating assembly and thereby the other of the sharpness of interference fringes in moire images and the number of interference fringes that is not adjusted in advance in the grating assembly 200 is adjusted.

Therefore, a large scale mechanism such as for rotating a subject with respect to the grating assembly 200 is not needed, and the slit directions of the first grating and the second grating can be changed with respect to a subject in a simple apparatus configuration. Further, when slit directions of the first grating and the second grating with respect to the subject are changed, adjustment for maintaining the sharpness of the reconstruction image can be carried out easily.

Moreover, by configuring the multi-slit rotation unit 121 so that the multi-slit 12 and the drive unit 122 rotate integrally, the multi-slit 12 can be moved stably in the slit aligning direction during image capturing even when the multi-slit 12 is rotated.

Further, by configuring so as to rotate the grating assembly 200 and the X-ray detector 16 integrally by the grating assembly rotation unit 210, there is no anisotropic influence on sharpness in horizontal and vertical directions of the X-ray detector 16. Therefore, horizontal and vertical sharpness of the reconstruction image can be approximately steady regardless of the rotation angle of the grating assembly 200.

Furthermore, by finely adjusting rotation angle of the multi-slit 12 by switching to micro step precision drive after rotating the motor unit 121a of the multi-slit rotation unit 121 by pulse drive, angle of the multi-slit 12 which is susceptible to heat by being near the X-ray source 11 can be adjusted accurately.

Moreover, according to the X-ray image capturing system of the above third to fifth embodiments, by covering the subject surface with a liquid substance having high adhesiveness to subject surface and its X-ray refractive index being approximately same as that of subject surface, image capturing is performed after adjusting so that the difference in X-ray refractive index between the subject surface and surrounding thereof be smaller than the difference in X-ray refractive index between the region of interest and surrounding thereof. Therefore, signal values indicating form variation in the subject surface are decreased and visibility of the region of interest in the subject in the reconstruction image of the subject can be improved.

Further, by including the subject holder 130 or the like for fixating the subject during image capturing, moving of the subject during image capturing can be prevented and a reconstruction image of the subject that leads to great accuracy in diagnosis with very little obscure parts due to moving of the subject can be obtained. Furthermore, by forming a reconstruction image with subject from a plurality of moire images with subject which are captured by placing the subject, by forming a reconstruction image without subject from a plurality of moire images without subject which are captured without placing the subject on the subject platform and by dividing the signal value of each pixel in the reconstruction image with subject by the signal value of its corresponding pixel in the reconstruction image without subject to form a subject reconstruction image for diagnosis, influence caused by the case where the subject holder 130 has a shape or thickness in which X-ray transmissivity is uneven from place to place on image quality (unexpected appearance of the subject holder 130 in the image) can be removed.

Here, the above described embodiments are preferred examples of the present invention, and the present invention is not limited to them.

For example, in the above embodiment, the X-ray source 11, the multi-slit 12, the subject platform 13, the first grating 14, the second grating 15 and the X-ray detector 16 are arranged in this order (hereinafter, called the first arrangement). However, even when the arrangement is in the order such as the X-ray source 11, the multi-slit 12, the first grating 14, the subject platform 13, the second grating 15 and the X-ray detector 16 (hereinafter, called the second arrangement), reconstruction image can be obtained by moving the multi-slit 12 while the first grating 14 and the second grating 15 remain fixed.

In the second arrangement, the center of subject and the first grating 14 are to be apart from each other for the distance corresponding to the thickness of the subject and sensitivity is degraded comparing to the above embodiments. However, on the other hand, in consideration of reducing exposure dose in the subject, X-rays are used effectively for the amount being absorbed by the first grating in this arrangement.

Moreover, effective space resolving power at the position of subject depends on focus diameter of X-rays, space resolving power of detector, enlargement ratio of subject, thickness of subject and the like. However, when the space resolving power of detector in the above embodiments is 120 μm (half width of Gaussian function) or less, the effective space resolving power becomes smaller in the second arrangement than in the first arrangement.

It is preferable that the arrangement order of the first grating 14 and the subject platform 13 is decided by taking sensitivity, space resolving power, X-ray absorption amount in the first grating 14 and the like into consideration.

Further, in the above embodiment, examples where the present invention is applied to the X-ray image capturing apparatus of Talbot-Lau interferometer which generates a plurality of moire images by fixing the positions of the first grating 14 and the second grating 15 and moving the multi-slit 12 are described. However, the present invention can also be applied to a conventional type X-ray image capturing apparatus using Talbot-Lau interferometer which generates a plurality of moire images by fixating the multi-slit 12 and moving the positions of the first grating 14 and the second grating 15.

Furthermore, the order of image capturing with subject and image capturing without subject is not limited to the order in the embodiments, and either can be performed first. The same can be said for the order for forming a reconstruction image with subject and forming a reconstruction image without subject.

Moreover, as for the X-ray detector 16, a cable-less cassette type FPD having a battery embedded therein which outputs image signals to the main body 18 in wireless manner may be used. According to such cassette type FPD, cables to connect with the main body 18 can be omitted and surrounding of the X-ray detector 16 can be smaller. By the surrounding being smaller in terms of space, the space around the subject's feel can be spacious and can have a configuration where the patient will not easily touch the X-ray detector 16.

Figure 36:
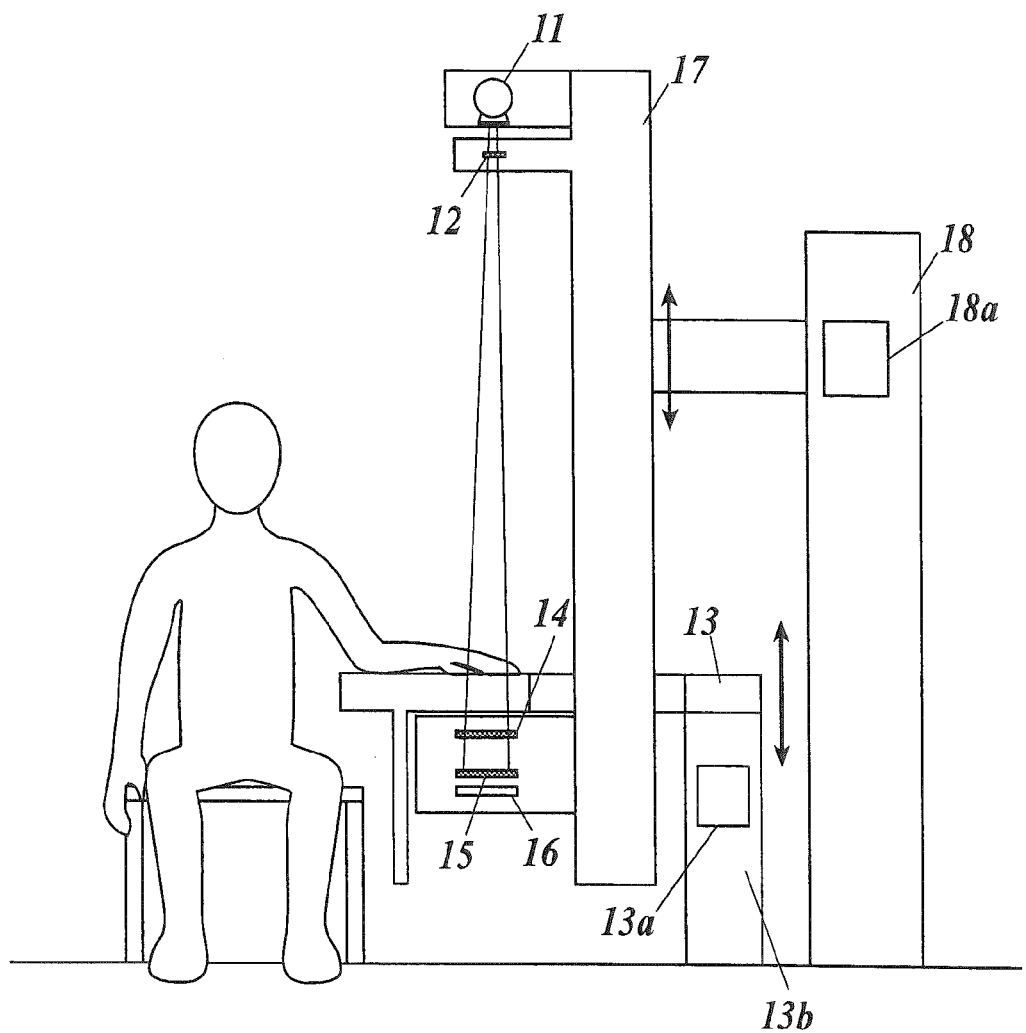
[FIG. 36] This is a side view showing a schematic configuration of a X-ray image capturing apparatus where the subject platform is held by a holding unit different from the holding unit of the first grating and the second grating.
Figure 37:
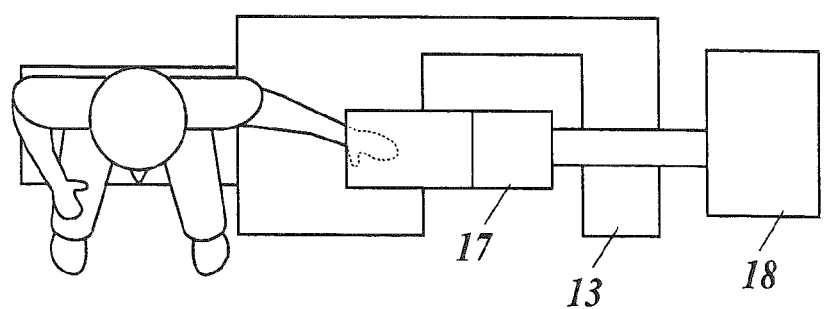
[FIG. 37] This is a plane view of the X-ray image capturing apparatus shown in FIG. 36.

Further, the subject platform 13 can easily transmit shaking by contacting with a patient. Therefore, the subject platform 13 may be separated from the holding unit 17 which includes the multi-slit, the first grating 14, the second grating 15 and the like which are required to have highly accurate positional relation and may be held by another holding unit. FIG. 36 shows a side view where the subject platform 13 is held by another holding unit 13b and FIG. 37 shows the plane view thereof. By structuring the subject platform 13 separately by separating the subject platform 13 from the first grating 14, the second grating 15 and the like in such way, influence on the positional relation of the multi-slit 12, the first gratin 14 and the second grating 15 can be reduced and the positional relation can be maintained.

When the subject platform 13 is structured separately, as shown in FIGS. 36 and 37, the drive unit 13a for moving the subject platform 13 in z direction is provided at the holding unit 13b. Thereby, position of the subject platform 13 can be adjusted according to the height of the subject. Although load such as the patient's weight is to be applied onto the subject platform 13, load to the holding unit 17 which rises and falls can be removed by the subject platform 13 and the holding unit 17 being separate structures. There is no need to reinforce the holding unit 17 to endure the load and the cost can be reduced.

Moreover, in the above embodiment, examples where moving and stopping of the multi-slit 12 is repeated for every image capturing at each of the steps is described. However, when it is expected that errors between the controlled amount and the actual moving amount accumulates and expands by repeating the moving and stopping depending on the configuration of the drive unit 122 and it is difficult to obtain moire images at constant intervals, it is preferred to perform image capturing in a continuous image capturing method where a plurality of times of image capturing are performed by moving the multi-slit 12 continuously. When the radiation switch in turned ON, moving of the multi-slit 12 is started, and when the multi-slit 12 reaches the stable moving region passing the unstable moving region at the time of activation, the multi-slit is further moved continuously to repeat pulse emission of X-rays and reading of image signal every time the multi-slit moves for a predetermined amount (for example, 4.56 (μm)).

It is preferred that the X-ray tube which enables pulse emission is used for the X-ray source 11 in the continuous image capturing method.

Further, as for the X-ray detector 16, it is preferred that FPD which can capture video and having a great supportable frame rate (the number of times of image capturing that can be performed per unit time) is used. When it is expected to perform 5 or more times of image capturing during several hundred m seconds to several seconds, frame rate of at least 10 frame/sec is required, more preferably, frame rate of 20 frame/sec or more is required.

In the case of continuous image capturing method, backup image capturing can be further performed before or after each step.

When the drive unit 122 is able to move the multi-slit 12 by a constant forwarding amount, that is, at a constant moving speed, by an ideal forwarding accuracy, a sine-curve can be formed by the moire images of the steps as shown in FIG. 22. However, when forwarding amount deviates due to deterioration with age, inertia effect at the time of activation of the drive unit 122, influence of viscosity of grease and the like, moire images at a constant cycle intervals cannot be obtained. For example, as shown in FIG. 22, although the moire image of step 3 originally corresponds to 0.4 cycle, a moire image slightly before or after 0.4 cycle is obtained when the forwarding amount of the drive unit 122 deviates at step 3.

When the cycle of moire image at each step varies, an accurate phase cannot be calculated and the subject image cannot be reproduced accurately in reconstruction image. Therefore, for example, total of 15 times of image capturing is to be performed by including backup image capturing in which images capturing is performed at ±0.1 second of each image capturing. In such way, three moire image are obtained at each step, and the moire image among the three which is closest to the sine-curve of relative intensity of X-ray is selected to be used. Thereby, even when error occurs in the forwarding amount of the drive unit 122, reproductively of reconstruction image can be improved.

The above described ±0.1 seconds as the adjustment time for backup image capturing is just an example, and adjustment time may be arbitrarily decided by test image capturing. For example, test image capturing may be performed by changing the adjustment time of backup image capturing, such as ±0.1 second and ±0.2 second, before and after image capturing of each step at the time of installing of the X-ray image capturing apparatus to obtain the adjustment time which seems to easily suite the sine-curve. In such way, the situation can be handled even when the required adjustment time differs according to device characteristic of the drive unit 122.

Figure 38:
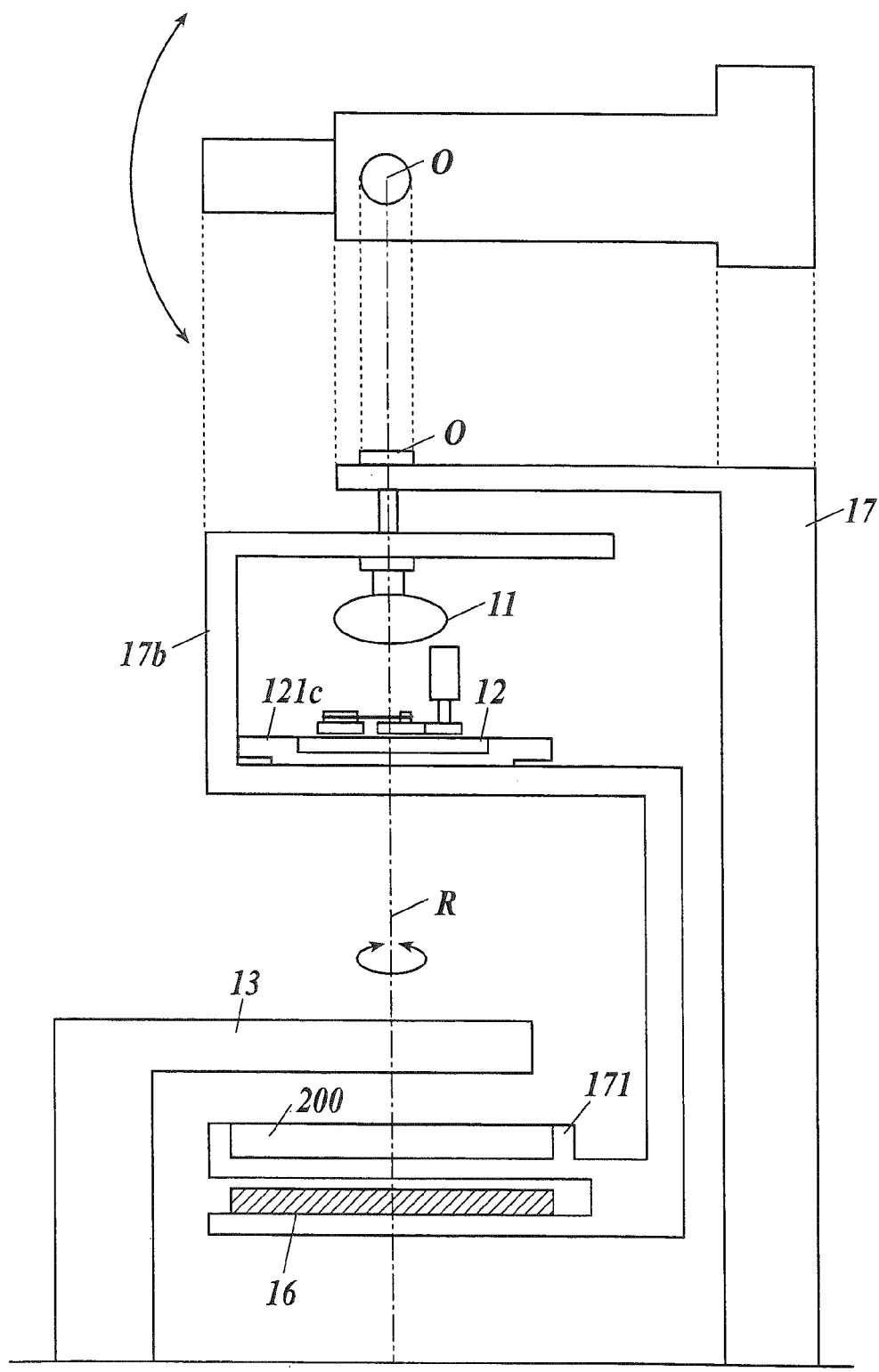
[FIG. 38] This is a diagram showing an example of a X-ray image capturing apparatus having a configuration where the X-ray source, the multi-slit and the grating assembly are rotated integrally.

Moreover, as another embodiment of the first and the second embodiments, as shown in FIG. 38, the X-ray source 11, the multi-slit 12 and the grating assembly 200 may be held by the holding unit 17 of the X-ray image capturing apparatus 1 and an arm 17b which is rotatable by setting the X-ray emission axis as the center thereof may be provided to the holding unit 17 so that the X-ray source 11, the multi-slit 12 and the grating assembly 200 are to rotate integrally around the X-ray emission axis when the arm 17b is rotated so that the slit direction of the grating assembly 200 be in a predetermined direction with respect to a subject. In the configuration shown in FIG. 38, by adjusting the relative positional relation of the first grating 14 and the second grating 15 and the relative positional relation of the grating assembly 200 and the multi-slit 12 so that the number of interference fringes and the sharpness of the interference fringes in moire images fulfill the predetermined standard at the time of shipment from a factory, there is no need to adjust the multi-slit 12 with respect to the grating assembly 200 at the time of image capturing. Here, the X-ray detector 16 may be held by the arm 17b so as to rotate integrally with the X-ray source 11, the multi-slit 12 and the grating assembly 200 or may be fixed and held by the holding unit 17 separately from the X-ray source 11, the multi-slit 12 and the grating assembly 200.

Moreover, when only a series of image capturing without subject (five steps) is performed regularly and when it is determined that an image is deviated from the sine-curve by determining whether each of the images matches the above described sine-curve, an announcement for informing that apparatus maintenance is needed is to be shown on the controller so that maintenances of such as precise decelerator system can be carried out, and thereby, highly accurate diagnosis reconstruction image can be maintained.

Further, in the above embodiment, the relative positional relation of the first grating 14 and the second grating 15 is pre-adjusted so that the number of interference fringes in moire image be minimum at the time of shipment from a factory and adjustment is carried out so that the interference fringes in the moire image be at their sharpest state by rotating the multi-slit 12 according to the rotation angle of the grating assembly 200 at the time of image capturing in order to make the reconstruction image be sharp. However, the relative positional relation of the first grating 14 and the second grating 15 may be pre-adjusted so that the interference fringes in moire image be at the sharpest state at the time of shipment from a factory and the number of interference fringes in moire image can be adjusted so as to be minimum number by rotating the multi-slit 12 according to the rotation angle of the grating assembly 200 at the time of image capturing.

Other than the above, with respect to detailed configuration and detailed operation of each devices that constitutes the X-ray image capturing system can be modified arbitrarily within the scope of the present invention.

The entire disclosure of Japanese Patent Applications No. 2010-061973, No. 2010-061983 and No. 2010-061993 filed on Mar. 18, 2010 including description, claims, drawings, and abstract are incorporated herein by reference in its entirety.

Industrial Applicability

Can be applied in image capturing of X-ray images in the medical field.

The invention claimed is:

1. A X-ray image capturing system, comprising:
   a X-ray source which emits X-rays;
   a first grating and a second grating;
   a subject platform;
   a X-ray detector in which conversion elements which generate electric signals according to the emitted X-rays are two dimensionally arranged and which reads the electric signals generated by the conversion elements as image signals, and
   a diagnosis image forming unit which is structured to capture both (a) one or more moire images with a subject placed on a subject platform (b) one or more moire images without the subject being placed on the subject platform, and the diagnosis image forming unit is further structured to form a subject reconstruction image for diagnosis on a basis of both (a) the one or more moire images with the subject, and (b) the one or more moire images without the subject,
   wherein every time the diagnosis image forming unit performs the image capturing with the subject, the diagnosis image forming unit performs the image capturing without the subject.

2. The X-ray image capturing system of claim 1, wherein the plurality of moire images without subject are captured before the plurality of moire images with subject.

3. The X-ray image capturing system of claim 1, further comprising a grating unit for radiation source for making the X-ray source be a multi-light source.

4. The X-ray image capturing system of claim 3, wherein the grating unit for radiation source is relatively displaced with respect to the first grating and the second grating.

5. The X-ray image capturing system of claim 1, wherein whether maintenance is needed or not is determined by using the one of more moire images without subject.

* * * * *